(12) United States Patent
Short et al.

(10) Patent No.: US 7,459,172 B2
(45) Date of Patent: Dec. 2, 2008

(54) METHOD OF MAKING A PROTEIN POLYMER AND USES OF THE POLYMER

(75) Inventors: Jay Short, Rancho Santa Fe, CA (US); Eric J. Mathur, Carlsbad, CA (US); W. Michael Lafferty, Encinitas, CA (US); Nelson Barton, San Diego, CA (US); Kevin Chow, San Diego, CA (US)

(73) Assignee: Verenium Corporation, San Diego, CA (US)

( * ) Notice: Subject to any disclaimer, the term of this patent is extended or adjusted under 35 U.S.C. 154(b) by 0 days.

(21) Appl. No.: 09/997,807

(22) Filed: Nov. 30, 2001

(65) Prior Publication Data

US 2003/0198681 A1    Oct. 23, 2003

(51) Int. Cl.
*A61K 31/74*   (2006.01)
*A61K 38/16*   (2006.01)

(52) U.S. Cl. .................. 424/486; 424/484; 530/333; 530/339; 530/350

(58) Field of Classification Search ................. 530/333, 530/339; 424/486, 484
See application file for complete search history.

(56) References Cited

U.S. PATENT DOCUMENTS

| 5,629,020 A | 5/1997 | Leone-Bay et al. |
| 5,712,366 A | 1/1998 | McGrath et al. |
| 5,851,536 A | 12/1998 | Yager et al. |
| 5,955,343 A | 9/1999 | Holmes et al. |
| 6,048,736 A | 4/2000 | Kosak |
| 6,083,902 A | 7/2000 | Cederhom-Williams |

FOREIGN PATENT DOCUMENTS

WO    WO-00/40962    7/2000

OTHER PUBLICATIONS

Jenekhe, S. et al Abstracts of Papers—American Chemical Society (2000), 220th, PMSE-268.*
Urry, D. et al. Materials Research Society Symposium Proceedings (1992), 255(Hierarchically Structured Materials), 411-22.*
Gyorog D.A. AIAA meeting, Jan. 19-21, New York, 1970.*
Stetter, "Ultrathin mycelia-forming organisms fro submarine volcanic areas having an optimum growth temperature of 105° C.", *Lehrstuhl für Mikrobiologie, Universität Regensburg*, Oct. 1, 1982.
Stetter et al., "Pyrodictium gen. nov., a New Genus of Submarine Disc-shaped Sulphur Reducing Archaebaceteria Growing Optimally at 105° C.", *Systemiatic and Applied Microbiology*, vol. 4, Aug. 8, 1983, pp. 535-551.
Konig et al., "The fine structure of the fibers of *Oyrodictium occultum*", *Federation of European Microbiological Societies*, 1988, pp. 207-212.
Rieger et al., "Ultrastucture of the hYperthermophilic Archaeon *Pyrodictium abyssi*", *Lehrstuhl für Mikrobiologie*, May 18, 1995, pp. 78-87.

Riegger et al., "Cultivation of Hyperthermophilic archaea in capillary tubes resulting in improved preservation of fine structures", *Arch Microbiol*, (1997) 268:373-379.
Pley et al., "*Pyrodictium abyssi* sp., nov. Represents a Novel Heterotrophic Marine Archaeal Hyperthermophile Growing at 110° C.", *System Appl. Microbiol.*, 14, 245-253 (1991).
Mai, Bianca, "In Vitro Untersuchungen zum extrazellulären Netzwerk von *Pyrodictium abyssi* TAG11" *Biologie und Medizin*, University of Regensburg, Naturwissenschaftlichen Fakultat III 1998 with English translation.
Mai et al., Journal of Bacteriology (1998) 180:4030-4035.
Mai, Genetic Characterization and Expression of the Large Thermosome Subunit from *Pyrodictium occultum* in *E. coli* and Molecular Biological Studies on the Extracellular Network from *Pyrodictium abyssi* Isolate TAG11. Thesis for the Department of Microbiology at the University of Regensburg (1995).
Rieger, Electron Microscope and Biochemical Studies on the Construction of the Network in *Pyrodictium*. Dissertation for the Department of Microbiology at the University of Regensburg (1998).
Schneider, Electron Microscope and Protein Chemical Studies on the Structure of the Fibers and the S-Layers from *Pyrodictium occultum*. Thesis for the Department of Microbiology at the University of Regensburg (1993).
Supplementary Partial European Search Report mailed on Sep. 6, 2005, for EP Patent Application No. 01996025.1, filed on Nov. 30, 2001, 4 pages.

* cited by examiner

*Primary Examiner*—Michael Borin
(74) *Attorney, Agent, or Firm*—Morrison & Foerster LLP

(57) ABSTRACT

A polymer is prepared by self-assembly of a plurality of monomeric polypeptide units. The polymer tends to form a nanotube and is capable of encapsulating a particular drug molecule. Once encapsulated in the polymer of the present invention, the drug molecule may be delivered to a particular location of human body to effectively cure a disease or treat a symptom.

Generally, the monomeric polypeptide unit of the present invention has a sequence found in *Pyrodictium abyssi*, a microorganism that produces an extracellular network having hollow protein tubes, or a sequence substantially identical thereto. The monomeric polypeptide may be mass produced using recombinant biotechnologies and be polymerized into the polymer of the present invention. One or more additional targeting vector may be attached to the monomeric polypeptide unit or the polymer to facilitate the targeting of the drug molecule that may be held there within. The sequence contained in the monomeric polypeptide unit may be further optimized using one or more technique selected from Gene Site Saturation Mutagenesis and GeneReasembly™.

32 Claims, 3 Drawing Sheets

METHOD OF MAKING A PROTEIN POLYMER AND USES OF THE POLYMER

BACKGROUND OF THE INVENTION

1. Field of the Invention

The present invention relates to the field of producing protein polymers through self-assembly of monomeric polypeptide units and to various uses of the self-assembled protein polymers.

2. Description of the Prior Art

Nanotechnology is taking center stage in efforts to build the next generation of computational tools and medical devices. The ability to rearrange molecular structures will have a profound effect on how products are manufactured. However, one drawback to synthetic nanostructures constructed from materials such as carbon and silicon has been the difficulty in attaining self-assembly of such components.

Nanobiotechnology relates to the development and use of biomolecular structures for applications such as biochips, drug delivery, data storage and nanomachinery. Nature produces molecular machinery that outperforms anything mankind currently knows how to construct with conventional manufacturing technology.

One application for nanobiotechnology is targeted drug delivery. The major goal of targeted drug delivery is the local accumulation and increased bioavailability of a therapeutic agent at its intended site of action, thereby reducing the drug dosage required to illicit the desired response. These sites of action include pathogenic bacteria and viruses, cancer cells, and areas of inflammation or other tissue damage. There are a variety of targeted drug delivery systems that are currently being developed and these include: liposomes, soluble polymer carriers, lipid and polymer gels, and various nanosuspensions (Torchilin, *Drug Targeting*. Eur. J. Pharmaceutical Sciences: v. 11, pp. S81-S91 (2000); Gerasimov, Boomer, Qualls, Thompson, *Cytosolic drug delivery using pH- and light-sensitive liposomes*, Adv. Drug Deliv. Reviews: v. 38, pp. 317-338 (1999); Hafez, Cullis, *Roles of lipid polymorphism in intracellular delivery*, Adv. Drug Deliv. Reviews: v. 47, pp. 139-148 (2001); Hashida, Akamatsu, Nishikawa, Fumiyoshi, Takakura, *Design of polymeric prodrugs of prostaglandin E1 having galactose residue for hepatocyte targeting*, J. Controlled Release: v. 62, pp. 253-262 (1999); Shah, Sadhale, Chilukuri, *Cubic phase gels as drug delivery systems*, Adv. Drug Deliv. Reviews: v. 47, pp.229-250 (2001); Müller, Jacobs, Kayser, *Nanosuspensions as particulate drug formulations in therapy: Rationale for development and what we can expect for the future*, Adv. Drug Delivery Reviews: v. 47, pp. 3-19 (2001)).

Targeted drug delivery systems that utilize encapsulation are attractive because 1) they require lower doses of therapeutic than non-targeted, even biodistribution approaches; 2) the therapeutic is less likely to cause unwanted side effects in healthy tissues because it remains concentrated, isolated, and therefore protected, until delivery; and 3) large numbers of therapeutic molecules can be delivered to a site of action using few targeting vectors attached to the encapsulation vessel.

One recent development in the area of nanotechnology employs eukaryotic microtube assemblies as a structural framework. Eukaryotic microtubules self-assemble into hollow rods and this property has made them attractive candidate structural components for a variety of nanotechnology applications (Jelinski, *Biologically related aspects of nanoparticles, nanostructured materials, and nanodevices*, In Nanostructure Science and Technology, A WTEC Panel Report prepared under the guidance of the Interagency Working Group on Nanoscience, Engineering and Technology (1999); Fritzsche, Kohler, Bohm, Unger, Wagner, Kirsch, Mertig, and Pompe, *Wiring of metalized microtubules by electron beam-induced structuring*, Nanotechnology: v. 10, pp. 331-335 (1999)).

However, the use of microtubules presents numerous challenges, including the lability of microtubule subunit proteins, the requirement for GTP for microtubule assembly and the need for microtubule stabilizing drugs like taxol to prevent the depolymerization of the tubules below 37° C. or in the presence of calcium. In addition, a major drawback of eukaryotic microtubules is the inability to overexpress microtubule subunits in *E. coli* in a functional form and therefore microtubule protein must be isolated from a native source, most commonly bovine brain (Lewis, Tian, Cowan, *The α- and β-tubulin folding pathways*, Trends in Cell Biology: v. 7, pp. 479-484(1997); Shah, Xu, Vickers, Williams, *Properties of microtubules assembled from mammalian tubulin synthesized in Escherichia coli*, Biochemistry: v. 40, pp. 4844-4852 (2001); Williams and Lee, *Preparation of Tubulin from Brain*, Methods in Enzymology (Academic Press): v. 85 pt. B, pp. 376-385 (1982)).

In addition, substrates for delivery of biocatalysts for synthesis reactions are needed. Such substrates may be three-dimensional to provide more catalytic sites and, as a result, it may be advantageous to develop such substrates from self-assembling polymers. Also, three-dimensional polymeric structures may be useful for other applications such as separation processes or screening methods.

Accordingly, it is an objective of certain embodiments of the present invention to provide a method of making a protein polymer, which employs self-assembly.

It is an objective of certain embodiments of the present invention to form a nanoscale drug delivery vehicle for targeted drug delivery.

It is an objective of certain embodiments of the present invention to provide fibers made from a self-assembled protein polymer.

It is a still further objective of certain embodiments of the present invention to provide three-dimensional arrays made from a self-assembled protein polymer.

It is a still further objective of certain embodiments of the present invention to provide a medium for biocatalysts based on a self-assembled protein polymer.

These and other objects of the present invention will be apparent from the summary and detailed descriptions, which follow.

SUMMARY OF THE INVENTION

In a first aspect, the present invention provides a method of producing a self-assembled protein polymer including the steps of: providing a plurality of polypeptides having a sequence selected from the group B amino acid sequences consisting of SEQ ID NOS: 2, 4, 6, 8 and 10 (hereafter "Group B amino acid sequences"), and sequences substantially identical thereto; and amino acid sequences encoded by a nucleic acid having a sequence selected from Group A nucleic acid sequences consisting of SEQ ID NOS: 1, 3, 5, 7, and 9 (hereafter "Group A nucleic acid sequences"), sequences substantially identical thereto and sequences complementary thereto; and inducing self-assembly of the plurality of polypeptides to form the polymer.

In a second aspect, the present invention provides a method of encapsulating a material including the steps of: dissolving a plurality of polypeptides having a sequence selected from the group consisting of SEQ ID NOS: 2, 4, 6, 8 and 10, and sequences substantially identical thereto; and amino acid sequences encoded by SEQ ID NOS: 1, 3, 5, 7, and 9, sequences substantially identical thereto and sequences complementary thereto; and the material in a solution; and polymerizing the plurality of polypeptides to form a polymer in the presence of the material in solution so as to encapsulate the material in the polymer.

In a third aspect, the present invention provides a drug delivery system including at least one drug encapsulated in a self-assembled protein polymer made from a plurality of polypeptides having a sequence selected from the group consisting of SEQ ID NOS: 2, 4, 6, 8 and 10, and sequences substantially identical thereto; and amino acid sequences encoded by SEQ ID NOS: 1, 3, 5, 7, and 9, sequences substantially identical thereto and sequences complementary thereto.

In a fourth aspect, the present invention provides a method of generating a variant including the steps of: obtaining a nucleic acid having a sequence selected from the group consisting of SEQ ID NOS: 1, 3, 5, 7,and 9, sequences substantially identical thereto, sequences complementary thereto, fragments having at least 30 consecutive nucleotides of SEQ ID NOS: 1, 3, 5, 7, and 9, and fragments having at least 30 consecutive nucleotides of the sequences complementary to SEQ ID NOS: 1, 3, 5, 7, 9; and modifying one or more nucleotides in the sequence to another nucleotide, deleting one or more nucleotides in the sequence, or adding one or more nucleotides to the sequence to generate a variant.

In a fifth aspect, the present invention provides an assay for identifying functional polypeptide fragments or variants encoded by fragments of SEQ ID NOS: 1, 3, 5, 7, and 9, and sequences substantially identical thereto, which retain the enzymatic function of the polypeptides of SEQ ID NOS: 2, 4, 6, 8 and 10, and sequences substantially identical thereto. The assay includes the steps of: dissolving a plurality of polypeptides of SEQ ID NOS: 2, 4, 6, 8 and 10, and sequences substantially identical thereto, or polypeptide fragments or variants encoded by SEQ ID NOS: 1, 3, 5, 7 and 9, sequences substantially identical thereto, and sequences substantially complementary thereto in a solution containing a template molecule and alkaline earth metal ion; and detecting the presence of a polymer in the solution by analyzing the solution using a method selected from High Performance Liquid Chromatography (HPLC), Gel Permeation Chromatography (GPC) and light scattering.

In a sixth aspect, the present invention provides a polypeptide including: a sequence selected from the group consisting of SEQ ID NOS: 2, 4, 6, 8 10, sequences substantially identical thereto, and amino acid sequences encoded by SEQ ID NOS: 1, 3, 5, 7, 9, sequences substantially identical thereto and sequences complementary thereto, and a functional group covalently attached to the sequence, wherein the side group comprises a structure selected from the group consisting of an antibody, an oligosaccharide, a polynucleotide, a polyethylene glycol and a charged group.

DETAILED DESCRIPTION OF THE PREFERRED EMBODIMENTS

Definitions

Figure 1:
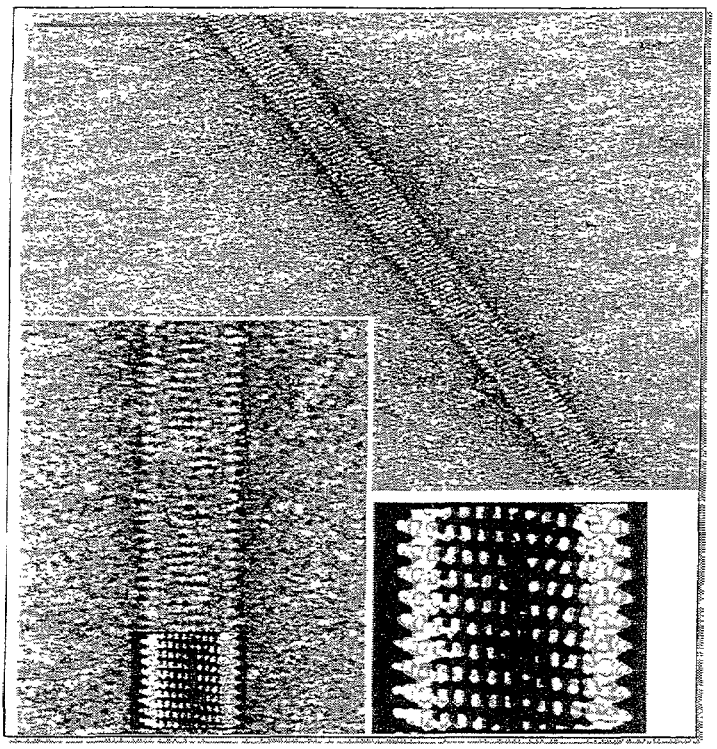
FIG. 1 shows a transmission electron micrograph of one embodiment of a self-assembled protein (SEQ ID NO:2) polymer useful in the present invention.
Figure 2:
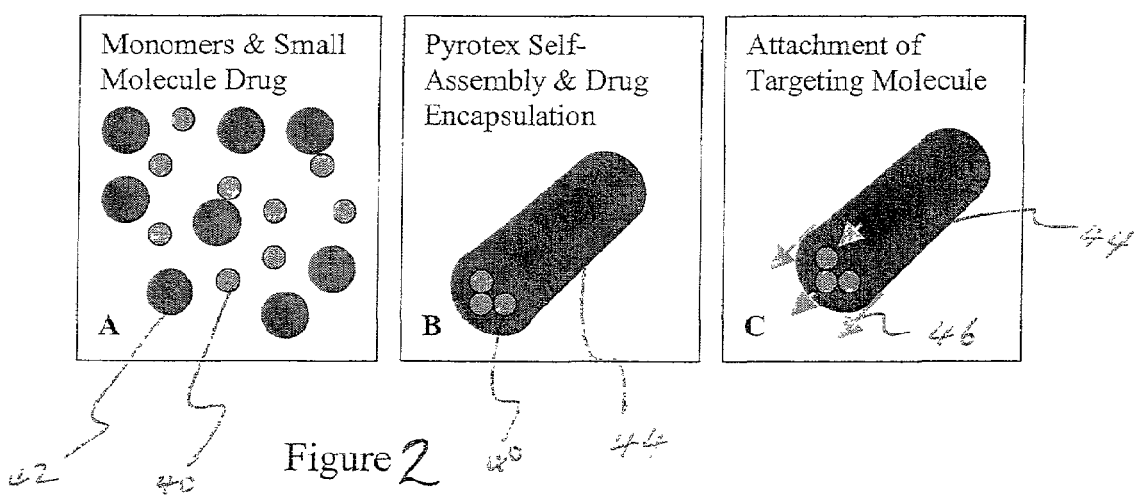
FIG. 2 diagrammatically illustrates one embodiment of a process for encapsulating a drug in a nanoscale delivery vehicle according to the present invention.

In the present application, the phrases "nucleic acid" or "nucleic acid sequence" as used herein refer to an oligonucleotide, nucleotide, polynucleotide, or to a fragment of any of these, to DNA or RNA of genomic or synthetic origin which may be single-stranded or double-stranded and may represent a sense or antisense strand, peptide nucleic acid (PNA), or to any DNA-like or RNA-like material, natural or synthetic in origin. In one embodiment, a "nucleic acid sequence" of the invention includes, for example, a sequence encoding a polypeptide as set forth in the Group B amino acid sequences, and variants thereof. In another embodiment, a "nucleic acid sequence" of the invention includes, for example, a sequence as set forth in the Group A nucleic acid sequences, sequences complementary thereto, fragments of the foregoing sequences and variants thereof.

A "coding sequence" or a "nucleotide sequence encoding" a particular polypeptide or protein, is a nucleic acid sequence which is transcribed and translated into a polypeptide or protein when placed under the control of appropriate regulatory sequences.

The term "gene" means the segment of DNA involved in producing a polypeptide chain; it includes regions preceding and following the coding region (leader and trailer) as well as, where applicable, intervening sequences (introns) between individual coding segments (exons).

"Amino acid" or "amino acid sequence" as used herein refer to an oligopeptide, peptide, polypeptide, or protein sequence, or to a fragment, portion, or subunit of any of these, and to naturally occurring or synthetic molecules. In one embodiment, an "amino acid sequence" or "polypeptide sequence" of the invention includes, for example, a sequence as set forth in the Group B amino acid sequences, fragments of the foregoing sequences and variants thereof. In another embodiment, an "amino acid sequence" of the invention includes, for example, a sequence encoded by a polynucleotide having a sequence as set forth in the Group A nucleic acid sequences, sequences complementary thereto, fragments of the foregoing sequences and variants thereof.

The term "polypeptide" as used herein, refers to amino acids joined to each other by peptide bonds or modified peptide bonds, i.e., peptide isosteres , and may contain modified amino acids other than the 20 gene-encoded amino acids. The polypeptides may be modified by either natural processes, such as post-translational processing, or by chemical modification techniques which are well known in the art. Modifications can occur anywhere in the polypeptide, including the peptide backbone, the amino acid side-chains and the amino or carboxyl termini. It will be appreciated that the same type of modification may be present in the same or varying degrees at several sites in a given polypeptide. Also a given polypeptide may have many types of modifications.

Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of a phosphytidylinositol, cross-linking cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristolyation, oxidation, pegylation, proteolytic processing, phosphorylation, prenylation, racemization, selenoylation, sulfation, and transfer-RNA mediated addition of amino acids to protein such as arginylation. (See Proteins —Structure and Molecular Properties 2nd Ed., T. E. Creighton, W. H. Freeman and Company, New York (1993); Posttranslational Covalent Modification of Proteins, B. C. Johnson, Ed., Academic Press, New York, pp. 1-12 (1983)).

As used herein, the term "isolated" means that the material is removed from its original environment (e.g., the natural environment if it is naturally occurring). For example, a naturally occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

As used herein, the term "purified" does not require absolute purity; rather, it is intended as a relative definition. Individual nucleic acids obtained from a library have been conventionally purified to electrophoretic homogeneity. The sequences obtained from these clones could not be obtained directly either from the library or from total human DNA. The purified nucleic acids of the invention have been purified from the remainder of the genomic DNA in the organism by at least 104-106 fold. However, the term "purified" also includes nucleic acids, which have been purified from the remainder of the genomic DNA or from other sequences in a library or other environment by at least one order of magnitude, typically two or three orders, and more typically four or five orders of magnitude.

As used herein, the term "recombinant" means that the nucleic acid is adjacent to "backbone" nucleic acid to which it is not adjacent in its natural environment. Additionally, to be "enriched" the nucleic acids will represent 5% or more of the number of nucleic acid inserts in a population of nucleic acid backbone molecules. Backbone molecules according to the invention include nucleic acids such as expression vectors, self-replicating nucleic acids, viruses, integrating nucleic acids, and other vectors or nucleic acids used to maintain or manipulate a nucleic acid insert of interest. Typically, the enriched nucleic acids represent 15% or more of the number of nucleic acid inserts in the population of recombinant backbone molecules. More typically, the enriched nucleic acids represent 50% or more of the number of nucleic acid inserts in the population of recombinant backbone molecules. In a one embodiment, the enriched nucleic acids represent 90% or more of the number of nucleic acid inserts in the population of recombinant backbone molecules.

"Recombinant" polypeptides or proteins refer to polypeptides or proteins produced by recombinant DNA techniques; i.e., produced from cells transformed by an exogenous DNA construct encoding the desired polypeptide or protein. "Synthetic" polypeptides or protein are those prepared by chemical synthesis. Solid-phase chemical peptide synthesis methods can also be used to synthesize the polypeptide or fragments of the invention. Such methods have been known in the art since the early 1960's (Merrifield, J. Am. Chem. Soc., 85:2149-2154, (1963)) (See also Stewart, and Young, Solid Phase Peptide Synthesis, 2 ed., Pierce Chemical Co., Rockford, Ill., pp. 11-12)) and have recently been employed in commercially available laboratory peptide design and synthesis kits (Cambridge Research Biochemicals). Such commercially available laboratory kits have generally utilized the teachings of Geysen et al, Proc. Natl. Acad. Sci., USA, 81:3998 (1984) and provide for synthesizing peptides upon the tips of a multitude of "rods" or "pins" all of which are connected to a single plate. When such a system is utilized, a plate of rods or pins is inverted and inserted into a second plate of corresponding wells or reservoirs, which contain solutions for attaching or anchoring an appropriate amino acid to the pin's or rod's tips. By repeating such a process step, i.e., inverting and inserting the rod's and pin's tips into appropriate solutions, amino acids are built into desired peptides. In addition, a number of available FMOC peptide synthesis systems are available. For example, assembly of a polypeptide or fragment can be carried out on a solid support using an Applied Biosystems, Inc. Model 431A automated peptide synthesizer. Such equipment provides ready access to the peptides of the invention, either by direct synthesis or by synthesis of a series of fragments that can be coupled using other known techniques.

A promoter sequence is "operably linked to" a coding sequence when RNA polymerase, which initiates transcription at the promoter will transcribe the coding sequence into mRNA.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described herein are known in the art or will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used in the manner known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. The manufacturer specifies appropriate buffers and substrate amounts for particular restriction enzymes. Incubation times of about 1 hour at 37° C. are ordinarily used, but may vary in accordance with the supplier's instructions. After digestion, gel electrophoresis may be performed to isolate the desired fragment.

"Oligonucleotide" refers to either a single stranded polydeoxynucleotide or two complementary polydeoxynucleotide strands, which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

The phrase "substantially identical" in the context of two nucleic acid sequences or polypeptides, refers to two or more sequences that have at least 50 nucleotide or amino acid residue identity over a region of at least about 100 residues, when compared and aligned for maximum correspondence, as measured using one of the known sequence comparison algorithms or by visual inspection. Substantially identical nucleic acid sequences may have at least 55%, 60%, 65%, 70%, 75%, 80%, 85%, 90% or 95% nucleotide or amino acid residue identity and this idetntied may also extend over at least about 150-200 residues, over the entire length of the coding regions of the nucleic acid sequences or polypeptides, or over the entire length of the nucleic acid sequences or polypeptides. Preferably, "substantially identical" in the context of a first nucleic acid sequence selected from Group A nucleic acid sequence and a second nucleic acid sequence refers to the first and second sequences having at least 50% nucleotide residue identity over at least about 100 residues, when compared and aligned for maximum correspondence, as measured using one of the known sequence comparison algorithms or by visual inspection. Preferably, "substantially identical" in the context of a first amino acid sequence selected from Group B nucleic acid sequence and a second amino acid sequence refers to the first and second amino acid sequences having at least 50% amino acid residue identity over at least about 100 residues, when compared and aligned for maximum correspondence, as measured using one of the known sequence comparison algorithms or by visual inspection.

Additionally a "substantially identical" amino acid sequence is a sequence that differs from a reference sequence by one or more conservative or non-conservative amino acid substitutions, deletions, or insertions, particularly when such a substitution occurs at a site that is not the active site of the molecule, and provided that the polypeptide essentially retains its functional properties. A conservative amino acid substitution, for example, substitutes one amino acid for another of the same class (e.g., substitution of one hydrophobic amino acid, such as isoleucine, valine, leucine, or methionine, for another, or substitution of one polar amino acid for another, such as substitution of arginine for lysine, glutamic acid for aspartic acid or glutamine for asparagine). One or more amino acids can be deleted, for example, from a haloalkane dehalogenase polypeptide, resulting in modification of the structure of the polypeptide, without significantly altering its biological activity or properties. For example, amino- or carboxyl-terminal amino acids that are not required for haloalkane dehalogenase biological activity can be removed. Modified polypeptide sequences of the invention can be assayed for haloalkane dehalogenase biological activity by any number of methods, including contacting the modified polypeptide sequence with an haloalkane dehalogenase substrate and determining whether the modified polypeptide decreases the amount of specific substrate in the assay or increases the byproducts of the enzymatic reaction of a functional haloalkane dehalogenase polypeptide with the substrate.

"Fragments" as used herein are a portion of a naturally occurring or recombinant protein, which can exist in at least two different conformations. Fragments can have the same or substantially the same amino acid sequence as the naturally occurring protein. "Substantially the same" means that an amino acid sequence is largely, but not entirely, the same, but retains at least one functional activity of the sequence to which it is related. In general two amino acid sequences are "substantially the same" or "substantially homologous" if they are at least about 70, but more typically about 85% or more identical. Fragments, which have different three-dimensional structures than the naturally occurring protein, are also included. An example of this is a "pro-form" molecule, such as a low activity proenzyme that can be modified by cleavage to produce a mature enzyme with significantly higher activity.

"Hybridization" refers to the process by which a nucleic acid strand joins with a complementary strand through base pairing. Hybridization reactions can be sensitive and selective so that a particular sequence of interest can be identified even in samples in which it is present at low concentrations. Suitably stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature.

For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5×SSPE, 0.3% SDS, and 200 ng/ml sheared and denatured salmon sperm DNA. Hybridization could occur under reduced stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

The term "variant" refers to polynucleotides or polypeptides of the invention modified at one or more base pairs, codons, introns, exons, or amino acid residues (respectively) yet still retain at least one beneficial property of the invention such as self-assembly. Variants can be produced by any number of means including methods such as, for example, error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, GSSM and any combination thereof.

The term "nanoscale" refers to a device, a material containing a structure, or other items having a size in the range of nanometers. More preferably, a device, material, or structure is referred to as "nanoscale" if the device, material, or structure has a dimensional size in the range of 1 nm to 1000 nm.

The term "nanoscale delivery vehicle" refers to a nanoscale supramolecular structure that is capable of encapsulating at least one molecule, traveling to a particular location in a human or animal body and releasing the molecule at the particular location. There are many examples of nanoscale delivery vehicles such as the hollow rod described in Jelinski, *Biologically related aspects of nanoparticles, nanostructured materials, and nanodevices*, In Nanostructure Science and Technology, A WTEC Panel Report prepared under the guidance of the Interagency Working Group on Nanoscience, Engineering and Technology (1999). Sometimes, this type of nanoscale delivery vehicle is also referred to as a "nanocapsule," "nanotube," "nanoparticle," "nanocage," "micelle," or by other similar names.

The term "polymer" refers to a large molecule that contains a plurality of repeating units or monomers. The linkages between these repeating units or monomers may be covalent bonds, hydrogen bonding, van der Waals force or other non-covalent interactions. The polymer may be formed by self-assembly of the monomers with or without a template molecule. Alternatively, the polymer may be formed by a chain polymerization reaction or a step polymerization reaction. Preferably, "polymer" refers to a molecule having a molecular weight of more than 5,000 Daltons. More preferably, "polymer" refers to a molecule having a molecular weight of more than 10,000 Daltons.

The term "polymerization" refers to the process of forming a polymer from monomers. The monomers may be polypeptides, lipids, or amphiphilic molecules that can self-assemble with or without the presence of a template molecule. In this particular case, "polymerization" essentially refers to the self-assembly process. Alternatively, the monomers may be unsaturated molecules that can undergo chain polymerization or copolymerization, or molecules with at least two reactive functional groups that can undergo step polymerization or copolymerization. The unsaturated molecules are exemplified as molecules with vinyl groups, molecules with methacrylate or acrylate groups, molecules with maleic moieties, and other similar unsaturated molecules. In this particular case, "polymerization" refers to the process of chain polymerization or copolymerization. The molecules with at least two reactive functional groups are exemplified as diacids, diamines, diols, dimercaptans, amino acids, monomeric nucleic acids, saccharides, and derivatives thereof.

The term "drug" or "drug molecule" refers to a therapeutic agent including a substance having a beneficial effect on a human or animal body when it is administered to the human or animal body. Preferably, the therapeutic agent includes a substance that can treat, cure or relieve one or more symptoms, illnesses, or abnormal conditions in a human or animal body or enhance the wellness of a human or animal body.

The term "deliver a drug to a particular location in a human or animal body" refers to the process that the drug, which may be encapsulated in a nanoscale delivery vehicle, travels through the organs, fluids or organ components of the human or animal body via the internal digestive system, blood circulation system, fluid circulation system, or external transfer means such as injection, transfusion. The drug reaches the particular location in the body based on a targeting means such as the affinity of the drug to the particular location, the affinity of the delivery vehicle to the particular location, the release tendency of the delivery vehicle at the particular location, controlled release of the drug by the delivery vehicle at the particular location by applying an external stimulus, combinations thereof, and equivalents thereof. The external stimulus may be radiation, chemical stimulation, thermal stimulation, or physical stimulation. Preferably, the external stimulus is targeted to a particular location in the body for maximum effect.

Preparation of the Polypeptide Monomer

In one embodiment, the process of preparing the polypeptide monomer begins with the step of attaching a nucleic acid encoding the polypeptide to a suitable vector. The nucleic acid may be obtained by isolating it from natural organisms such as *Pyrodictium abyssi*. Alternatively, the nucleic acid may be obtained by PCR, as a natural nucleic acid or by synthetic methods. The nucleic acid may also be produced by modifying a nucleic acid using one or more of the methods discussed below or other known methods for evolving or modifying sequences.

Preferably, the nucleic acid has a sequence as set forth in the Group A nucleic acid sequences or may be produced by modifying a nucleic acid having a sequence as set forth in the Group A nucleic acid sequences and sequences substantially identical thereto using the methods described below. Group A nucleic acid sequences and the Group B amino acid sequences, which are encoded by Group A nucleic acid sequences have substantial homology. The alignment for the corresponding Group A nucleic acid sequences and Group B amino acid sequences using a common bioinformatic algorithm or an algorithm discussed above is shown below. In the following alignment, CanA and CanA_pep stand for nucleic acid SEQ ID No. 1 and its corresponding amino acid SEQ ID No. 2, respectively; CanB and CanB_pep stand for nucleic acid SEQ ID No. 3 and its corresponding amino acid SEQ ID No. 4, respectively; CanC and CanC_pep stand for nucleic acid SEQ ID No. 5 and its corresponding amino acid SEQ ID No. 6, respectively; CanD_partial stands for nucleic acid SEQ ID No. 7 or its corresponding amino acid SEQ ID No. 8; and CanE_partial stands for nucleic acid SEQ ID No. 9 or its corresponding amino acid SEQ ID No. 10.

```
Nucleic acid alignment for SEQ ID NOS. 1, 3, 5, 7, and 9:

1                                                           50
     CanA      (1)  GTGAAGTACACAACCCTAGCTATAGCGGGTATTATTGCCTCGGCTGCCGC
     CanB      (1)  GTGAAGCCTACGGCTCTAGCCCTGGCTGGTATCATTGCCTCGGCTGCCGA
     CanC      (1)  ATGAGGTACACGACCCTAGCTCTGGCCGGCATAGTGGCCTCGGCTGCCGC
CanD_partial   (1)  --------------------------------------------------
CanE_partial   (1)  --------------------------------------------------
   Consensus   (1)   TGA G   AC  C CTAGC  T GC GG AT  T GCCTCGGCTGCCG
                   51                                                  100
     CanA     (51)  CCTCGCCCTCCTAGCAGGCTTCGCCACCACCCAGAGCCCCCTCAACAGCT
     CanB     (51)  CCTCGCCCTGCTAGCAGGCTTCGCCACCACCCAGAGCCCGCTCAACAGCT
     CanC     (51)  CCTCGCCCTGCTAGCAGGCTTCGCCACGACCCAGAGCCCGCTAAGCAGCT
CanD_partial   (1)  ---------------------------------------------AGCT
CanE_partial   (1)  ---------------------------------------------AGCT
   Consensus  (51)  CCTCGCCCT CTAGCAGGCTTCGCCAC ACCCAGACCCC CT A CAGCT
                   101                                                 150
```

-continued

```
          CanA  (101) TCTACGCCACCGGTACAGCACAGGCAGTAAGCGAGCCAATAGACGTAGAA
          CanB  (101) TCTACGCCACCGGCACAGCAGCCGCAACAAGCGAGCCAATAGACGTAGAG
          CanC  (101) TCTACGCCACCGGCACAGCACAAGCAGTAAGCGAGCCAATAGACGTAGAG
   CanD_partial    (5) TCTACGCCACCGGCACAGCACAGGCAGTAAGCGAGCCAATAGACGTGGTA
   CanE_partial    (5) TCTACGCCACCGGCACAGCAGAGGCAACAAGCGAGCCAATAGACGTTGTA
     Consensus  (101) TCTACGCCACCGGCACAGCACAGGCAGTAAGCGAGCCAATAGACGTAGAA
                      151                                              200
          CanA  (151) AGCCACCT---CGGCAGCATAACCCCCGCAGCCGGCGCACAGGGCAGTGA
          CanB  (151) AGCCACCT---CAGCAGCATAGCCCCTGCTGCTGGCGCACAGGGCAGCCA
          CanC  (151) AGCCACCTAGACAACACCATAGCCCCTGCTGCCGGTGCACAGGGCTACAA
   CanD_partial   (55) AGCAGCCTCGGTACG---CTAAATACTGCCGCTGGTGCACAGGGTAAGCA
   CanE_partial   (55) AGCAACCTTAACACGGCCATAGCCCCTGCTGCCGGCGCCCAGGGCAGCGT
     Consensus  (151) AGCCACCT   CA CA CATACCCCTGCTGCCGGCGCACAGGGCAGC A
                      201                                              250
          CanA  (198) CGACATAGGTTACGCAATAGTGTGGATAAAGGACCAGGTCAATGATGTAA
          CanB  (198) GGACATAGGCTACTTCAACGTGACCGCCAAGGATCAAGTGAACGTGACAA
          CanC  (201) GGACATGGGCTACATTAAGATAACTAACCAGTCAAAAGTTAATGTAATAA
   CanD_partial  (102) GACGCTAGGAGACATAACAATATATGCGCACAATGACGTGAACATAACAA
   CanE_partial  (105) GGGCATAGGCAGCATAACAATAGAGAACAAGACTGACGTGAACGTTGTGA
     Consensus  (201) GGACATAGGCTACATAA AATA   A CAAG AT A GTCAACGT ATAA
                      251                                              300
          CanA  (248) AGCTGAAGGTGACCCTGCGTAACGCTGAGCAGCTAAAGCCCTACTTCAAG
          CanB  (248) AGATAAAGGTGACCCTGGCTAACGCTGAGCAGCTAAAGCCCTACTTCAAG
          CanC  (251) AGCTGAAGGTGACTCTCGCTAACGCCGAGCAGCTAAAGCCCTACTTCGAC
   CanD_partial  (152) AGCTAAAGGTCACGCTTGCTAACGCTGCACAGCTAAGACCATACTTCAAG
   CanE_partial  (155) AGCTGAAGATAACCCTCGCCAACGCTGAGCAGCTAAAGCCCTACTTCGAC
     Consensus  (251) AGCTGAAGGTGACCCT GCTAACGCTGAGCAGCTAAAGCCCTACTTCAAG
                      301                                              350
          CanA  (298) TACCTACAGATACAGATAACAAGCGGCTATGAGACGAACAGCACAGCTCT
          CanB  (298) TACCTACAGATAGTGCTAAAGAGCG-------------------------
          CanC  (301) TACCTACAGCTAGTACTCACAAGCAAC------------------GCCAC
   CanD_partial  (202) TACCTGATAATAAAGCTAGTAAGCCT--------------GGACAGC-AA
   CanE_partial  (205) TACCTACAGATAGTGCTAAAGAGCGT--------------TGACAGC-AA
     Consensus  (301) TACCTACAGATAGTGCTAA AAGCG                ACAGC A
                      351                                              400
          CanA  (348) AGGCAACTTCAGCGAGACCAAGGCTGTGATAAGCCTCGACAACCCCAGCG
          CanB  (323) AGGTAGCTGA--CGAGATCAAGGCCGTAATAAGCATAGACAAGCCTAGCG
          CanC  (333) TGGCACCGACA---TGGTTAAGGCTGTGCTAAGCCTCGAGAAGCCTAGCG
   CanD_partial  (237) CGGCAACGAGTCCGAGGAAAGGGCATGATAACTCTATGGAAGCCTTACG
   CanE-partial  (240) CGAGATCAAGGCTG------------TGCTAAGCCTCGAGAAGCCCAGCG
     Consensus  (351)    GGCA C A    CGAG    AAGGC GTGATAAGCCTCGAGAAGCCTAGCG
                      401                                              450
```

-continued

```
        CanA  (398) CCGTGATAGTACTAGACAAGGAGGATATAGCAGTGCTCTATCCGGACAAG
        CanB  (371) CCGTCATAATACTAGACAGCCAGGA-------------------------
        CanC  (380) CAGTCATAATACTAGACAACGATGA-------------------------
 CanD_partial (287) CCGTGATAATACTAGACCATGAAGA-------------------------
 CanE_partial (278) CAGTCATAATACTGGACAACGAGGA-------------------------
   Consensus  (401) CCGTCATAATACTAGACAACGAGGA
                    451                                              500
        CanA  (448) ACCGGTTACACAAACACTTCGATATGGGTACCCGGTGAACCTGACAAGAT
        canB  (396) ----------------CTTCGACA--------------G-----------
        CanC  (405) ----------------CTACGATA--------------G-----------
 canD_partial (312) ----------------TTTCAACAACGACA--------------------
 canE_partial (303) ----------------CTTCCAGGGCGGC---------------------
   Consensus  (451)                 CTTCGA  A           G
                    501                                              550
        CanA  (498) AATTGTCTACAACGAGACAAAGCCAGTAGCTATACTGAACTTCAAGGCCT
        canB  (405) ------CAACAACAGAGCAAAG--ATAAGCGCCACTG----------CCT
        CanC  (414) ------CACTAACAAGATACAGCTA-AAGGTAGA---A-------G-CCT
 canD_partial (326) -----TCGACAATGACGGCAACAATGACGCCAAGATAAGGGTTGTAGCCT
 canE_partial (316) -------GACAACCAGTGCCAGATAGACGCCACC------------GCCT
   Consensus  (501)       C ACAAC AG  AAAG  AGAAGC A A T A           GCCT
                    551                                              600
        CanA  (548) TCTACGAGGCTAAGGAGGGTATGCTATTCGACAGCCTGCCAGTGATATTC
        canB  (437) ACTACGAGGCTAAGGAGGGCATGCTATTCGACAGCCTACCGCTAATATTC
        CanC  (446) ACTATGAGGCTAAGGAGGGCATGCTATTCGACAGCCTACCAGTAATACTG
 canD_partial (371) ACTATGAGGCTAAGGAGGGTATGCT-------------------------
 canE_partial (347) ACTACGAGGCTAAGGAGGGTATGCTA------------------------
   Consensus  (551) ACTACGAGGCTAAGGAGGGTATGCTATTCGACAGCCT CC  T ATA T
                    601                                 642
        CanA  (598) AACTTCCAGGTGCTACAAGTAGGCTAA---------------
        canB  (487) AACATACAGGTGCTAAGCGTCAGCTAA---------------
        CanC  (496) AACTTCCAGGTACTGAGCGCCGCTTGCAGTCCCTTGTGGTGA
 canD_partial (396) ------------------------------------------
 canE_partial (373) ------------------------------------------
   Consensus  (601) AAC T CAGGT CT    G     T
```

Amino Acid Alignment for SEQ ID NOS. 2, 4, 6, 8, and 10:

```
1                                                50
    CanA_pep  (1) VKYTTLAIAGIIASAAALALLAGFATTQSPLNSFYATGTAQAVSEPIDVE
    CanB_pep  (1) VKPTALALAGIIASAADLALLAGFATTQSPLNSFYATGTAAATSEPIDVE
    CanC_pep  (1) MRYTTLALAGIVASAAALALLAGFATTQSPLSSFYATGTAQAVSEPIDVE
```

```
CanD_partial    (1)  ------------------------------SFYATGTAQAVSEPIDVV

CanE_partial    (1)  ------------------------------SFYATGTAEATSEPIDVV

Consensus    (1)  VK T LALAGIIASAA LALLAGFATTQSPL SFYATGTAQAVSEPIDVE
                     51                                              100

CanA_pep   (51)  SHLG-SITPAAGAQGSDDIGYAIVWIKDQVNDVKLKVTLRNAEQLKPYFK

CanB_pep   (51)  SHLS-SIAPAAGAQGSQDIGYFNVTAKDQVNVTKIKVTLANAEQLKPYFK

CanC_pep   (51)  SHLDNTIAPAAGAQGYKDMGYIKITNQSKVNVIKLKVTLANAEQLKPYFD

CanD_partial   (19)  SSLGTLNT-AAGAQGKQTLGDITIYAHNDVNITKLKVTLANAAQLRPYGK

CanE_partial   (19)  SNLNTAIAPAAGAQGSVGIGSITIENKTDVNVVKLKITLANAEQLKPYFD

Consensus   (51)  SHL  SIAPAAGAQGS DIGYI I  K  VNVVKLKVTLANAEQLKPYFK
                     101                                             150

CanA_pep  (100)  YLQIQITSGYETNSTALGNFSETKAVISLDNPSAVIVLDKEDIAVLYPDK

CanB_pep  (100)  YLQIVLKSEVAD---------EIKAVISIDKPSAVIILDSQDFDSNNR--

CanC_pep  (101)  YLQLVLTSNATG-------TDMVKAVLSLEKPSAVIILDNDDYDSIN---

CanD_partial   (68)  YLIIKLVSLDSNG-----NESEEKGMITLWKPYAVIILDHEDFNNDID--

CanE_partial   (69)  YLQIVLKSVDSN---------EIKAVLSLEKPSAVIILDNEDFQG-----

Consensus  (101)  YLQIVL S  S           EIKAVISLDKPSAVIILD EDF
                     151                                             200

CanA_pep  (150)  TGYTNTSIWVPGEPDKIIVYNETKPVAILNFKAFYEAKEGMLFDSLPVIF

CanB_pep  (139)  -------------------------AKISATAYYEAKEGMLFDSLPLIF

CanC_pep  (141)  ----------------KIQ---------LKVEAYYEAKEGMLFDSLPVIL

CanD_partial  (111)  ------------------N--DGNNDAKIRVVAYYEAKEGM---------

CanE_partial  (105)  ----------------------GDNQCQIDATAYYEAKEGML--------

Consensus  (151)                            A I   AYYEAKEGMLFDSLPVI
                     201      214

CanA_pep  (200)  NFQVLQVG------

CanB_pep  (163)  NIQVLSVS------

CanC_pep  (166)  NFQVLSAACSPLW-

CanD_partial  (132)  --------------

CanE_partial  (125)  --------------

Consensus  (201)  N QYL
```

The vector used in this modification step may be selected from many known vectors such as the one contained in plasmid pEX-CAN-A, which is described in detail by B, Mai et al in Mai, Frey, Swanson, Mathur, Stetter, *Molecular Cloning and Functional Expression of a Protein-Serine/Threonine Phosphatase from the hyperthermophilic Archaeon Archaeon abyssi TAG*11. J. Bacterial. In press (1998), pBluescript® II phagemid KS(-), pET17b and a suitable virus. More preferably, the vector used in the present invention is selected from a vector listed in Table 1.

TABLE 1

Plasmids used for cloning and expression in *E. coli*.

| PLASMID | SIZE | PROPERTY |
|---|---|---|
| pBluescript ® II phagemid KS(-) | 2.96 kb | AmpR; MCS flanked by T3 and T7 promoter; replication vector |
| pET17b | 3.31 kb | AmpR; MCS flanked by T7 promoter and T7 terminator; expression vector |

In a second step of the process, the vector with the predetermined nucleic acid attached is inserted or implanted into a host cell using any method known to a skilled person in the art. The host cell may be an *E. coli* cell, a fungus cell, a cancer cell, a *Pyrodictium abyssi* cell, a hyperthermus butylicus cell, Pseudomonas or any other suitable prokaryotic or eukaryotic cells. More preferably, the host cell used in the present invention is selected from an organism listed in Table 2. Most preferably the host cell is *E. coli* BL21 (DE3).

TABLE 2

Organisms cultivated for DNA isolation or transformation

| Organism | Reference |
|---|---|
| *Pyrodictium abyssi* isolate TAG11 | Deininger W., 1994 |
| *Hyperthermus butylicus* | Zillig et al., 1990; DSMZ 5456 |
| *E. coli* DH5α | Woodcock et al., 1989; [Stratagene, Heidelberg] |
| *E. coli* Y1090 | Young and Davis, 1983; [Stratagene, Heidelberg] |
| *E. coli* BL 21 (DE3) | Phillips et al., 1984; [Stratagene, Heidelberg] |

Alternatively, the host cell used in the present invention may be a plant cell so that the plant may be able to over express the nucleic acid to produce the monomeric polypeptide of the present invention.

In a third step of the process, the gene represented by the predetermined nucleic acid is expressed in the host cell under suitable conditions such as by employing a suitable culture or medium. During this third step of the process, the host cell may replicate itself to produce additional host cells containing the same vectors therein. A suitable culture media and suitable conditions for expression of *Pyrodictium abyssi* are described below.

| Medium for *Pyrodictium abyssi* (pH 5.5-6.0) | |
|---|---|
| SME | 500.00 ml |
| $KH_2PO_4$ | 0.50 g |
| Yeast extract | 0.50 g |
| $Na_2S_2O_3$ | 1.00 g |

| -continued | |
|---|---|
| Medium for *Pyrodictium abyssi* (pH 5.5-6.0) | |
| Resazurin (1%) | 0.30 ml |
| $H_2O_{bidist}$ | up to 1,000.00 ml |

The medium was autoclaved. The cultivation temperature was 102° C. The host cell was incubated while standing. "SME" stands for Synthetic Sea Water, which is typically prepared using the procedure described in Example 1.

A suitable media and suitable conditions for expression of *Hyperthermus butylicus* are described below.

| Medium for *Hyperthermus butylicus* (pH 7.0) | |
|---|---|
| SME | 500.00 ml |
| $KH_2PO_4$ | 0.50 g |
| $NH_4Cl$ | 0.50 g |
| Sulfur | 5.00 g |
| KJ | 2.50 mg |
| $NiSO_4 \times 6 H_2O$ | 2.00 mg |
| Resazurin (1%) | 0.30 ml |
| $H_2O_{bidist}$ | up to 1,000.00 ml |

The medium was vaporized. Prior to inoculation, 6 g trypton per liter were added in the form of an autoclaved stock solution (10%, w/v). The cultivation temperature was 100° C. The host cell was incubated while standing.

Exemplary media for *E. Coli* are described as follows. *E. coli* strains were routinely cultivated aerobically on $LB_0$ medium (see below) at 37° C. with intensive shaking (250 rpm). Plasmid-carrying or vector-carrying strains with resistance to antibiotics were cultivated in the presence of the corresponding antibiotic (100 μg/ml) ampicillin, 34 μg/ml chloramphenicol).

| $LB_0$ Medium for *E. coli* DH5α and BL 21 (DE3), (pH 7.0) | |
|---|---|
| Trypton | 10.00 g |
| Yeast extract | 5.00 g |
| NaCl | 10.00 g |
| $H_2O_{bidist}$ | up to 1,000 ml |
| $LB_0$ Medium for *E. coli* Y1090 (pH 7.0) | |
| Trypton | 10.00 g |
| Yeast extract | 10.00 g |
| NaCl | 5.00 g |
| $H_2O_{bidist}$ | up to 1,000 ml |
| NZYM Medium for *E.coli* Y1090 (pH 7.0) | |
| NZ amines | 10.00 g |
| NaCl | 5.00 g |
| Yeast extract | 5.00 g |
| $MgSO_4 \times 7 H_2O$ | 2.00 g |
| $H_2O_{bidist}$ | up to 1,000 ml |

For the preparation of plates, 15 g agar per liter of medium was used. Added to the Top Agar were 7.5g agarose per liter medium. Exemplary conditions for expressing the gene encoded by the nucleic acid used in the present invention involve: keeping the medium at 37° C. under aeration in a fermentor, stirring the medium containing the *E. Coli* cells, and inducing the gene overexpression by adding IPTG.

In a preferred embodiment, the process of preparing monomeric polypeptides or polypeptide units of the present invention further includes a fourth step of isolating the produced polypeptide from the culture or medium. The step of isolating the monomeric polypeptide can be carried out by French pressing the *E. Coli* cell mass from a solution, removing particles from the solution by centrifugation, heat-treating the solution to precipitate the unwanted heat-sensitive proteins, centrifugating the heat-treated solution to obtain a clear solution, precipitating the monomeric polypeptides from the clear solution using ammonium sulfate and dialyzing the monomeric polypeptides to reduce the ionic strength of the solution.

In one embodiment, the prepared monomeric polypeptide has a molecular weight of 21 kDa. The monomeric polypeptide of this embodiment self-assembles in the presence of divalent cations into polymeric hollow rods with an outer diameter of approximately 25 nm and an inner diameter of approximately 20 nm, thus exhibiting molecular dimensions and an overall morphology similar to eukaryotic microtubules. In addition, the monomeric polypeptide is thermally stable up to 100° C. for a prolonged time.

The nucleic acids encoding the monomeric polypeptides of the present invention may be modified using one or more methods described below or any method known to a person skilled in the art so that the modified nucleic acid may be used to prepare modified polypeptide monomers. The nucleic acid used in the present invention may also be modified using one or more of the gene evolution technologies such as Gene Site Saturation Mutagenesis (GSSM™) and GeneReassembly™ which are respectively described in U.S. Pat. Nos. 6,171,820 and 5,965,408, which are hereby incorporated by reference for the purpose of describing these gene evolution technologies.

Methodology

Nucleic acid shuffling is a method for in vitro or in vivo homologous recombination of pools of shorter or smaller polynucleotides to produce a polynucleotide or polynucleotides. Mixtures of related nucleic acid sequences or polynucleotides are subjected to sexual PCR to provide random polynucleotides, and reassembled to yield a library or mixed population of recombinant hybrid nucleic acid molecules or polynucleotides.

CDRs from a pool of 100 different selected antibody sequences can be permutated in up to 1006 different ways. This large number of permutations cannot be represented in a single library of DNA sequences. Accordingly, it is contemplated that multiple cycles of DNA shuffling and selection may be required depending on the length of the sequence and the sequence diversity desired.

Error-prone PCR, may also be employed and, in some circumstances may be preferable since it keeps all the selected CDRs in the same relative sequence, generating a much smaller mutant cloud. The template polynucleotide, which may be used in the methods of this invention may be DNA or RNA. It may be of various lengths depending on the size of the gene or shorter or smaller polynucleotide to be recombined or reassembled. Preferably, the template polynucleotide is from 50 bp to 50 kb. It is contemplated that entire vectors containing the nucleic acid encoding the protein of interest can be used in the methods of this invention, and in fact have been successfully used.

The template polynucleotide may be obtained by amplification using the PCR reaction (U.S. Pat. Nos. 4,683,202 and 4,683,195) or other amplification or cloning methods. However, the removal of free primers from the PCR products before subjecting them to pooling of the PCR products and sexual PCR may provide more efficient results. Failure to adequately remove the primers from the original pool before sexual PCR can lead to a low frequency of crossover clones.

The template polynucleotide often should be double-stranded. A double-stranded nucleic acid molecule is recommended to ensure that regions of the resulting single-stranded polynucleotides are complementary to each other and thus can hybridize to form a double-stranded molecule.

It is contemplated that single-stranded or double-stranded nucleic acid polynucleotides having regions of identity to the template polynucleotide and regions of heterology to the template polynucleotide may be added to the template polynucleotide, at this step. It is also contemplated that two different but related polynucleotide templates can be mixed at this step.

The double-stranded polynucleotide template and any added double-or single-stranded polynucleotides are subjected to sexual PCR which includes slowing or halting to provide a mixture of from about 5 bp to 5 kb or more. Preferably the size of the random polynucleotides is from about 10 bp to 1000 bp, more preferably the size of the polynucleotides is from about 20 bp to 500 bp.

Alternatively, it is also contemplated that double-stranded nucleic acid having multiple nicks may be used in the methods of this invention. A nick is a break in one strand of the double-stranded nucleic acid. The distance between such nicks is preferably 5 bp to 5 kb, more preferably between 10 bp to 1000 bp. This can provide areas of self-priming to produce shorter or smaller polynucleotides to be included with the polynucleotides resulting from random primers, for example.

The concentration of any one specific polynucleotide will not be greater than 1% by weight of the total polynucleotides, more preferably the concentration of any one specific nucleic acid sequence will not be greater than 0.1% by weight of the total nucleic acid. The number of different specific polynucleotides in the mixture will be at least about 100, preferably at least about 500, and more preferably at least about 1000.

At this step single-stranded or double-stranded polynucleotides, either synthetic or natural, may be added to the random double-stranded shorter or smaller polynucleotides in order to increase the heterogeneity of the mixture of polynucleotides.

It is also contemplated that populations of double-stranded randomly broken polynucleotides may be mixed or combined at this step with the polynucleotides from the sexual PCR process and optionally subjected to one or more additional sexual PCR cycles.

Where insertion of mutations into the template polynucleotide is desired, single-stranded or double-stranded polynucleotides having a region of identity to the template polynucleotide and a region of heterology to the template polynucleotide may be added in a 20 fold excess by weight as compared to the total nucleic acid, more preferably the single-stranded polynucleotides may be added in a 10 fold excess by weight as compared to the total nucleic acid.

Where a mixture of different but related template polynucleotides is desired, populations of polynucleotides from each of the templates may be combined at a ratio of less than about 1:100, more preferably the ratio is less than about 1:40. For example, a backcross of the wild-type polynucleotide with a population of mutated polynucleotide may be desired to eliminate neutral mutations (e.g., mutations yielding an insubstantial alteration in the phenotypic property being selected for). In such an example, the ratio of randomly provided wild-type polynucleotides which may be added to the randomly provided sexual PCR cycle hybrid polynucleotides is approximately 1:1 to about 100:1, and more preferably from 1:1 to 40:1.

The mixed population of random polynucleotides are denatured to form single-stranded polynucleotides and then re-annealed. Only those single-stranded polynucleotides having regions of homology with other single-stranded polynucleotides will re-anneal.

The random polynucleotides may be denatured by heating. One skilled in the art could determine the conditions necessary to completely denature the double-stranded nucleic acid. Preferably the temperature is from 80° C. to 100° C., more preferably the temperature is from 90° C. to 96° C. other methods which may be used to denature the polynucleotides include pressure and pH.

The polynucleotides may be re-annealed by cooling. Preferably the temperature is from 20° C. to 75° C., more preferably the temperature is from 40° C. to 65° C. If a high frequency of crossovers is needed based on an average of only 4 consecutive bases of homology, recombination can be forced by using a low annealing temperature, although the process becomes more difficult. The degree of renaturation, which occurs will depend on the degree of homology between the populations of single-stranded polynucleotides.

Renaturation can be accelerated by the addition of polyethylene glycol ("PEG") or salt. The salt concentration is preferably from 0 mM to 200 mM, more preferably the salt concentration is from 10 mM to 100 mm. The salt may be KCl or NaCl. The concentration of PEG is preferably from 0% to 20%, more preferably from 5% to 10%.

The annealed polynucleotides are next incubated in the presence of a nucleic acid polymerase and dNTP's (i.e. dATP, dCTP, DGTP and dTTP). The nucleic acid polymerase may be the Klenow fragment, the Taq polymerase or any other DNA polymerase known in the art.

The approach to be used for the assembly depends on the minimum degree of homology that should still yield crossovers. If the areas of identity are large, Taq polymerase can be used with an annealing temperature of between 45-65° C. If the areas of identity are small, Klenow polymerase can be used with an annealing temperature of between 20-30° C. One skilled in the art could vary the temperature of annealing to increase the number of cross-overs achieved.

The polymerase may be added to the random polynucleotides prior to annealing, simultaneously with annealing or after annealing.

The cycle of denaturation, renaturation and incubation in the presence of polymerase is referred to herein as shuffling or reassembly of the nucleic acid. This cycle is repeated for a desired number of times. Preferably the cycle is repeated from 2 to 50 times, more preferably the sequence is repeated from 10 to 40 times.

The resulting nucleic acid is a larger double-stranded polynucleotide of from about 50 bp to about 100 kb, preferably the larger polynucleotide is from 500 bp to 50 kb.

This larger polynucleotides may contain a number of copies of a polynucleotide having the same size as the template polynucleotide in tandem. This concatemeric polynucleotide is then denatured into single copies of the template polynucleotide. The result will be a population of polynucleotides of approximately the same size as the template polynucleotide. The population will be a mixed population where single or double-stranded polynucleotides having an area of identity and an area of heterology have been added to the template polynucleotide prior to shuffling.

These polynucleotides are then cloned into the appropriate vector and the ligation mixture used to transform bacteria.

It is contemplated that the single polynucleotides may be obtained from the larger concatemeric polynucleotide by amplification of the single polynucleotide prior to cloning by a variety of methods including PCR (U.S. Pat. Nos. 4,683,195 and 4,683,202), rather than by digestion of the concatemer.

The vector used for cloning is not critical provided that it will accept a polynucleotide of the desired size. If expression of the particular polynucleotide is desired, the cloning vehicle should further comprise transcription and translation signals next to the site of insertion of the polynucleotide to allow expression of the polynucleotide in the host cell. Preferred vectors include the pUC series and the pBR series of plasmids.

The resulting bacterial population will include a number of recombinant polynucleotides having random mutations. This mixed population may be tested to identify the desired recombinant polynucleotides. The method of selection will depend on the polynucleotide desired.

For example, if a polynucleotide, which encodes a protein with increased binding efficiency to a ligand is desired, the proteins expressed by each of the portions of the polynucleotides in the population or library may be tested for their ability to bind to the ligand by methods known in the art (i.e. panning, affinity chromatography). If a polynucleotide, which encodes for a protein with increased drug resistance is desired, the proteins expressed by each of the polynucleotides in the population or library may be tested for their ability to confer drug resistance to the host organism. One skilled in the art, given knowledge of the desired protein, could readily test the population to identify polynucleotides, which confer the desired properties onto the protein.

It is contemplated that one skilled in the art could use a phage display system in which fragments of the protein are expressed as fusion proteins on the phage surface (Pharmacia, Milwaukee Wis.). The recombinant DNA molecules are cloned into the phage DNA at a site, which results in the transcription of a fusion protein a portion of which is encoded by the recombinant DNA molecule. The phage containing the recombinant nucleic acid molecule undergoes replication and transcription in the cell. The leader sequence of the fusion protein directs the transport of the fusion protein to the tip of the phage particle. Thus the fusion protein, which is partially encoded by the recombinant DNA molecule is displayed on the phage particle for detection and selection by the methods described above.

It is further contemplated that a number of cycles of nucleic acid shuffling may be conducted with polynucleotides from a sub-population of the first population, which sub-population contains DNA encoding the desired recombinant protein. In this manner, proteins with even higher binding affinities or enzymatic activity could be achieved.

It is also contemplated that a number of cycles of nucleic acid shuffling may be conducted with a mixture of wild-type polynucleotides and a sub-population of nucleic acid from the first or subsequent rounds of nucleic acid shuffling in order to remove any silent mutations from the sub-population.

Any source of nucleic acid, in purified form can be utilized as the starting nucleic acid. Thus the process may employ DNA or RNA including messenger RNA, which DNA or RNA may be single or double stranded. In addition, a DNA-RNA hybrid, which contains one strand of each may be utilized. The nucleic acid sequence may be of various lengths depending on the size of the nucleic acid sequence to be mutated. Preferably the specific nucleic acid sequence is from 50 to 50000 base pairs. It is contemplated that entire vectors containing the nucleic acid encoding the protein of interest may be used in the methods of this invention.

The nucleic acid may be obtained from any source, for example, from plasmids such a pBR322, from cloned DNA or RNA or from natural DNA or RNA from any source including bacteria, yeast, viruses and higher organisms such as plants or animals. DNA or RNA may be extracted from blood or tissue material. The template polynucleotide may be obtained by amplification using the polynucleotide chain reaction (PCR, see U.S. Pat. Nos. 4,683,202 and 4,683,195). Alternatively, the polynucleotide may be present in a vector present in a cell and sufficient nucleic acid may be obtained by culturing the cell and extracting the nucleic acid from the cell by methods known in the art.

Any specific nucleic acid sequence can be used to produce the population of hybrids by the present process. It is only necessary that a small population of hybrid sequences of the specific nucleic acid sequence exist or be created prior to the present process.

The initial small population of the specific nucleic acid sequences having mutations may be created by a number of different methods. Mutations may be created by error-prone PCR. Error-prone PCR uses low-fidelity polymerization conditions to introduce a low level of point mutations randomly over a long sequence. Alternatively, mutations can be introduced into the template polynucleotide by oligonucleotide-directed mutagenesis. In oligonucleotide-directed mutagenesis, a short sequence of the polynucleotide is removed from the polynucleotide using restriction enzyme digestion and is replaced with a synthetic polynucleotide in which various bases have been altered from the original sequence. The polynucleotide sequence can also be altered by chemical mutagenesis. Chemical mutagens include, for example, sodium bisulfite, nitrous acid, hydroxylamine, hydrazine or formic acid. other agents which are analogues of nucleotide precursors include nitrosoguanidine, 5-bromouracil, 2-aminopurine, or acridine. Generally, these agents are added to the PCR reaction in place of the nucleotide precursor thereby mutating the sequence. Intercalating agents such as proflavine, acriflavine, quinacrine and the like can also be used. Random mutagenesis of the polynucleotide sequence can also be achieved by irradiation with X-rays or ultraviolet light. Generally, plasmid polynucleotides so mutagenized are introduced into *E. coli* and propagated as a pool or library of hybrid plasmids.

Alternatively the small mixed population of specific nucleic acids may be found in nature in that they may consist of different alleles of the same gene or the same gene from different related species (i.e., cognate genes). Alternatively, they may be related DNA sequences found within one species, for example, the immunoglobulin genes.

Once the mixed population of the specific nucleic acid sequences is generated, the polynucleotides can be used directly or inserted into an appropriate cloning vector, using techniques well-known in the art.

The choice of vector depends on the size of the polynucleotide sequence and the host cell to be employed in the methods of this invention. The templates of this invention may be plasmids, phages, cosmids, phagemids, viruses (e.g., retroviruses, parainfluenzavirus, herpesviruses, reoviruses, paramyxoviruses, and the like), or selected portions thereof (e.g., coat protein, spike glycoprotein, capsid protein). For example, cosmids and phagemids are preferred where the specific nucleic acid sequence to be mutated is larger because these vectors are able to stably propagate large polynucleotides.

If the mixed population of the specific nucleic acid sequence is cloned into a vector it can be clonally amplified by inserting each vector into a host cell and allowing the host cell to amplify the vector. This is referred to as clonal amplification because while the absolute number of nucleic acid sequences increases, the number of hybrids does not increase. Utility can be readily determined by screening expressed polypeptides.

The DNA shuffling method of this invention can be performed blindly on a pool of unknown sequences. By adding to the reassembly mixture oligonucleotides (with ends that are homologous to the sequences being reassembled) any sequence mixture can be incorporated at any specific position into another sequence mixture. Thus, it is contemplated that mixtures of synthetic oligonucleotides, PCR polynucleotides or even whole genes can be mixed into another sequence library at defined positions. The insertion of one sequence (mixture) is independent from the insertion of a sequence in another part of the template. Thus, the degree of recombination, the homology required, and the diversity of the library can be independently and simultaneously varied along the length of the reassembled DNA.

This approach of mixing two genes may be useful for the humanization of antibodies from murine hybridomas. The approach of mixing two genes or inserting alternative sequences into genes may be useful for any therapeutically used protein, for example, interleukin I, antibodies, tPA and growth hormone. The approach may also be useful in any nucleic acid for example, promoters or introns or untranslated region or untranslated regions of genes to increase expression or alter specificity of expression of proteins. The approach may also be used to mutate ribozymes or aptamers.

Shuffling requires the presence of homologous regions separating regions of diversity. Scaffold-like protein structures may be particularly suitable for shuffling. The conserved scaffold determines the overall folding by self-association, while displaying relatively unrestricted loops that mediate the specific binding. Examples of such scaffolds are the immunoglobulin beta-barrel, and the four-helix bundle which are well-known in the art. This shuffling can be used to create scaffold-like proteins with various combinations of mutated sequences for binding.

Saturation Mutagenesis

In one aspect, this invention provides for the use of proprietary codon primers (containing a degenerate N,N,G/T sequence) to introduce point mutations into a polynucleotide, so as to generate a set of progeny polypeptides in which a full range of single amino acid substitutions is represented at each amino acid position. The oligos used are comprised contiguously of a first homologous sequence, a degenerate N,N,G/T sequence, and preferably but not necessarily a second homologous sequence. The downstream progeny translational products from the use of such oligos include all possible amino acid changes at each amino acid site along the polypeptide, because the degeneracy of the N,N,G/T sequence includes codons for all 20 amino acids.

In one aspect, one such degenerate oligo (comprised of one degenerate N,N,G/T cassette) is used for subjecting each original codon in a parental polynucleotide template to a full range of codon substitutions. In another aspect, at least two degenerate N,N,G/T cassettes are used—either in the same oligo or not, for subjecting at least two original codons in a parental polynucleotide template to a full range of codon substitutions. Thus, more than one N,N,G/T sequence can be contained in one oligo to introduce amino acid mutations at more than one site. This plurality of N,N,G/T sequences can be directly contiguous, or separated by one or more additional nucleotide sequence(s). In another aspect, oligos serviceable for introducing additions and deletions can be used either alone or in combination with the codons containing an N,N, G/T sequence, to introduce any combination or permutation of amino acid additions, deletions, and/or substitutions.

In a particular exemplification, it is possible to simultaneously mutagenize two or more contiguous amino acid positions using an oligo that contains contiguous N,N,G/T triplets, i.e. a degenerate (N,N,G/T)n sequence.

In another aspect, the present invention provides for the use of degenerate cassettes having less degeneracy than the N,N, G/T sequence. For example, it may be desirable in some instances to use (e.g. in an oligo) a degenerate triplet sequence comprised of only one N, where said N can be in the first second or third position of the triplet. Any other bases including any combinations and permutations thereof can be used in the remaining two positions of the triplet. Alternatively, it may be desirable in some instances to use (e.g. in an oligo) a degenerate N,N,N triplet sequence, or an N,N, G/C triplet sequence.

It is appreciated, however, that the use of a degenerate triplet (such as N,N,G/T or an N,N, G/C triplet sequence) as disclosed in the instant invention is advantageous for several reasons. In one aspect, this invention provides a means to systematically and fairly easily generate the substitution of the full range of possible amino acids (for a total of 20 amino acids) into each and every amino acid position in a polypeptide. Thus, for a 100 amino acid polypeptide, the instant invention provides a way to systematically and fairly easily generate 2000 distinct species (i.e. 20 possible amino acids per position×100 amino acid positions). It is appreciated that there is provided, through the use of an oligo containing a degenerate N,N,G/T or an N,N, G/C triplet sequence, 32 individual sequences that code for 20 possible amino acids. Thus, in a reaction vessel in which a parental polynucleotide sequence is subjected to saturation mutagenesis using one such oligo, there are generated 32 distinct progeny polynucleotides encoding 20 distinct polypeptides. In contrast, the use of a non-degenerate oligo in site-directed mutagenesis leads to only one progeny polypeptide product per reaction vessel.

This invention also provides for the use of nondegenerate oligos, which can optionally be used in combination with degenerate primers disclosed. It is appreciated that in some situations, it is advantageous to use nondegenerate oligos to generate specific point mutations in a working polynucleotide. This provides a means to generate specific silent point mutations, point mutations leading to corresponding amino acid changes, and point mutations that cause the generation of stop codons and the corresponding expression of polypeptide fragments.

Thus, in a preferred embodiment of this invention, each saturation mutagenesis reaction vessel contains polynucleotides encoding at least 20 progeny polypeptide molecules such that all 20 amino acids are represented at the one specific amino acid position corresponding to the codon position mutagenized in the parental polynucleotide. The 32-fold degenerate progeny polypeptides generated from each saturation mutagenesis reaction vessel can be subjected to clonal amplification (e.g. cloned into a suitable *E. coli* host using an expression vector) and subjected to expression screening. When an individual progeny polypeptide is identified by screening to display a favorable change in property (when compared to the parental polypeptide), it can be sequenced to identify the correspondingly favorable amino acid substitution contained therein.

It is appreciated that upon mutagenizing each and every amino acid position in a parental polypeptide using saturation mutagenesis as disclosed herein, favorable amino acid changes may be identified at more than one amino acid position. One or more new progeny molecules can be generated that contain a combination of all or part of these favorable amino acid substitutions. For example, if 2 specific favorable amino acid changes are identified in each of 3 amino acid positions in a polypeptide, the permutations include 3 possibilities at each position (no change from the original amino acid, and each of two favorable changes) and 3 positions. Thus, there are 3×3×3 or 27 total possibilities, including 7 that were previously examined—6 single point mutations (i.e. 2 at each of three positions) and no change at any position.

In yet another aspect, site-saturation mutagenesis can be used together with shuffling, chimerization, recombination and other mutagenizing processes, along with screening. This invention provides for the use of any mutagenizing process(es), including saturation mutagenesis, in an iterative manner. In one exemplification, the iterative use of any mutagenizing process(es) is used in combination with screening.

Thus, in a non-limiting exemplification, this invention provides for the use of saturation mutagenesis in combination with additional mutagenization processes, such as process where two or more related polynucleotides are introduced into a suitable host cell such that a hybrid polynucleotide is generated by recombination and reductive reassortment.

In addition to performing mutagenesis along the entire sequence of a gene, the instant invention provides that mutagenesis can be use to replace each of any number of bases in a polynucleotide sequence, wherein the number of bases to be mutagenized is preferably every integer from 15 to 100,000. Thus, instead of mutagenizing every position along a molecule, one can subject a discrete number of bases (preferably a subset totaling from 15 to 100,000) to mutagenesis. Preferably, a separate nucleotide is used for mutagenizing each position or group of positions along a polynucleotide sequence. A group of 3 positions to be mutagenized may be a codon. The mutations are preferably introduced using a mutagenic primer, containing a heterologous cassette, also referred to as a mutagenic cassette. Preferred cassettes can have from 1 to 500 bases. Each nucleotide position in such heterologous cassettes be N, A, C, G, T, A/C, A/G, A/T, C/G, C/T, G/T, C/G/T, A/G/T, A/C/T, A/C/G, or E, where E is any base that is not A, C, G, or T (E can be referred to as a designer oligo). The tables below show exemplary tri-nucleotide cassettes (there are over 3000 possibilities in addition to N,N, G/T and N,N,N and N,N,A/C).

In a general sense, saturation mutagenesis is comprised of mutagenizing a complete set of mutagenic cassettes (wherein each cassette is preferably 1-500 bases in length) in defined polynucleotide sequence to be mutagenized (wherein the sequence to be mutagenized is preferably from 15 to 100,000 bases in length). Thusly, a group of mutations (ranging from 1 to 100 mutations) is introduced into each cassette to be mutagenized. A grouping of mutations to be introduced into one cassette can be different or the same from a second grouping of mutations to be introduced into a second cassette during the application of one round of saturation mutagenesis. Such groupings are exemplified by deletions, additions, groupings of particular codons, and groupings of particular nucleotide cassettes.

Defined sequences to be mutagenized include preferably a whole gene, pathway, cDNA, an entire open reading frame (ORF), and entire promoter, enhancer, repressor/transactivator, origin of replication, intron, operator, or any polynucleotide functional group. Generally, preferred "defined sequences" for this purpose may be any polynucleotide that is a 15 base-polynucleotide sequence, and polynucleotide sequences of lengths between 15 bases and 15,000 bases (this invention specifically names every integer in between). Considerations in choosing groupings of codons include types of amino acids encoded by a degenerate mutagenic cassette.

In a particularly preferred exemplification a grouping of mutations that can be introduced into a mutagenic cassette, this invention specifically provides for degenerate codon substitutions (using degenerate oligos) that code for 2, 3, 4, 5, 6, 7, 8, 9, 10, 11, 12, 13, 14, 15, 16, 17, 18, 19, and 20 amino acids at each position, and a library of polypeptides encoded thereby.

Chimerizations

In vitro Shuffling

The equivalents of some standard genetic matings may also be performed by shuffling in vitro. For example, a "molecular backcross" can be performed by repeatedly mixing the hybrid's nucleic acid with the wild-type nucleic acid while selecting for the mutations of interest. As in traditional breeding, this approach can be used to combine phenotypes from different sources into a background of choice. It is useful, for example, for the removal of neutral mutations that affect unselected characteristics (i.e. immunogenicity). Thus it can be useful to determine which mutations in a protein are involved in the enhanced biological activity and which are not, an advantage which cannot be achieved by error-prone mutagenesis or cassette mutagenesis methods.

Large, functional genes can be assembled correctly from a mixture of small random polynucleotides. This reaction may be of use for the reassembly of genes from the highly fragmented DNA of fossils. In addition random nucleic acid fragments from fossils may be combined with polynucleotides from similar genes from related species.

It is also contemplated that the method of this invention can be used for the in vitro amplification of a whole genome from a single cell as is needed for a variety of research and diagnostic applications. DNA amplification by PCR is in practice limited to a length of about 40 kb. Amplification of a whole genome such as that of E. coli (5,000 kb) by PCR would require about 250 primers yielding 125 forty kb polynucleotides. This approach is not practical due to the unavailability of sufficient sequence data. On the other hand, random production of polynucleotides of the genome with sexual PCR cycles, followed by gel purification of small polynucleotides will provide a multitude of possible primers. Use of this mix of random small polynucleotides as primers in a PCR reaction alone or with the whole genome as the template should result in an inverse chain reaction with the theoretical endpoint of a single concatamer containing many copies of the genome.

100 fold amplification in the copy number and an average polynucleotide size of greater than 50 kb may be obtained when only random polynucleotides are used. It is thought that the larger concatamer is generated by overlap of many smaller polynucleotides. The quality of specific PCR products obtained using synthetic primers will be indistinguishable from the product obtained from unamplified DNA. It is expected that this approach will be useful for the mapping of genomes.

The polynucleotide to be shuffled can be produced as random or non-random polynucleotides, at the discretion of the practitioner. Moreover, this invention provides a method of shuffling that is applicable to a wide range of polynucleotide sizes and types, including the step of generating polynucleotide monomers to be used as building blocks in the reassembly of a larger polynucleotide. For example, the building blocks can be fragments of genes or they can be comprised of entire genes or gene pathways, or any combination thereof.

Exonuclease-Mediated Shuffling

In a particular embodiment, this invention provides for a method for shuffling, assembling, reassembling, recombining, &/or concatenating at least two polynucleotides to form a progeny polynucleotide (e.g. a chimeric progeny polynucleotide that can be expressed to produce a polypeptide or a gene pathway). In a particular embodiment, a double stranded polynucleotide end (e.g. two single stranded sequences hybridized to each other as hybridization partners) is treated with an exonuclease to liberate nucleotides from one of the two strands, leaving the remaining strand free of its original partner so that, if desired, the remaining strand may be used to achieve hybridization to another partner.

In a particular aspect, a double stranded polynucleotide end (that may be part of—or connected to—a polynucleotide or a nonpolynucleotide sequence) is subjected to a source of exonuclease activity. Serviceable sources of exonuclease activity may be an enzyme with 3' exonuclease activity, an enzyme with 5' exonuclease activity, an enzyme with both 3' exonuclease activity and 5' exonuclease activity, and any combination thereof. An exonuclease can be used to liberate nucleotides from one or both ends of a linear double stranded polynucleotide, and from one to all ends of a branched polynucleotide having more than two ends. The mechanism of action of this liberation is believed to be comprised of an enzymatically-catalyzed hydrolysis of terminal nucleotides, and can be allowed to proceed in a time-dependent fashion, allowing experimental control of the progression of the enzymatic process.

By contrast, a non-enzymatic step may be used to shuffle, assemble, reassemble, recombine, and/or concatenate polynucleotide building blocks that is comprised of subjecting a working sample to denaturing (or "melting") conditions (for example, by changing temperature, pH, and /or salinity conditions) so as to melt a working set of double stranded polynucleotides into single polynucleotide strands. For shuffling, it is desirable that the single polynucleotide strands participate to some extent in annealment with different hybridization partners (i.e. and not merely revert to exclusive reannealment between what were former partners before the denaturation step). The presence of the former hybridization partners in the reaction vessel, however, does not preclude, and may sometimes even favor, reannealment of a single stranded polynucleotide with its former partner, to recreate an original double stranded polynucleotide.

In contrast to this non-enzymatic shuffling step comprised of subjecting double stranded polynucleotide building blocks to denaturation, followed by annealment, the instant invention further provides an exonuclease-based approach requiring no denaturation—rather, the avoidance of denaturing conditions and the maintenance of double stranded polynucleotide substrates in annealed (i.e. non-denatured) state are necessary conditions for the action of exonucleases (e.g., exonuclease III and red alpha gene product). Additionally in contrast, the generation of single stranded polynucleotide sequences capable of hybridizing to other single stranded polynucleotide sequences is the result of covalent cleavage—and hence sequence destruction—in one of the hybridization partners. For example, an exonuclease III enzyme may be used to enzymatically liberate 3' terminal nucleotides in one hybridization strand (to achieve covalent hydrolysis in that polynucleotide strand); and this favors hybridization of the remaining single strand to a new partner (since its former partner was subjected to covalent cleavage).

By way of further illustration, a specific exonuclease, namely exonuclease III is provided herein as an example of a 3' exonuclease; however, other exonucleases may also be used, including enzymes with 5' exonuclease activity and enzymes with 3' exonuclease activity, and including enzymes not yet discovered and enzymes not yet developed. It is particularly appreciated that enzymes can be discovered, optimized (e.g. engineered by directed evolution), or both discovered and optimized specifically for the instantly disclosed approach that have more optimal rates &/or more highly specific activities &/or greater lack of unwanted activities. In fact it is expected that the instant invention may encourage the discovery &/or development of such designer enzymes. In sum, this invention may be practiced with a variety of currently available exonuclease enzymes, as well enzymes not yet discovered and enzymes not yet developed.

The exonuclease action of exonuclease III requires a working double stranded polynucleotide end that is either blunt or has a 5' overhang, and the exonuclease action is comprised of enzymatically liberating 3' terminal nucleotides, leaving a single stranded 5' end that becomes longer and longer as the exonuclease action proceeds. Any 5' overhangs produced by this approach may be used to hybridize to another single stranded polynucleotide sequence (which may also be a single stranded polynucleotide or a terminal overhang of a partially double stranded polynucleotide) that shares enough homology to allow hybridization. The ability of these exonuclease III-generated single stranded sequences (e.g. in 5' overhangs) to hybridize to other single stranded sequences allows two or more polynucleotides to be shuffled, assembled, reassembled, &/or concatenated.

Furthermore, it is appreciated that one can protect the end of a double stranded polynucleotide or render it susceptible to a desired enzymatic action of a serviceable exonuclease as necessary. For example, a double stranded polynucleotide end having a 3' overhang is not susceptible to the exonuclease action of exonuclease III. However, it may be rendered susceptible to the exonuclease action of exonuclease III by a variety of means; for example, it may be blunted by treatment with a polymerase, cleaved to provide a blunt end or a 5' overhang, joined (ligated or hybridized) to another double stranded polynucleotide to provide a blunt end or a 5' overhang, hybridized to a single stranded polynucleotide to provide a blunt end or a 5' overhang, or modified by any of a variety of means).

According to one aspect, an exonuclease may be allowed to act on one or on both ends of a linear double stranded polynucleotide and proceed to completion, to near completion, or to partial completion. When the exonuclease action is allowed to go to completion, the result will be that the length of each 5' overhang will be extend far towards the middle region of the polynucleotide in the direction of what might be considered a "rendezvous point" (which may be somewhere near the polynucleotide midpoint). Ultimately, this results in the production of single stranded polynucleotides (that can become dissociated) that are each about half the length of the original double stranded polynucleotide. Alternatively, an exonuclease-mediated reaction can be terminated before proceeding to completion.

Thus this exonuclease-mediated approach is serviceable for shuffling, assembling &/or reassembling, recombining, and concatenating polynucleotide building blocks, which polynucleotide building blocks can be up to ten bases long or tens of bases long or hundreds of bases long or thousands of bases long or tens of thousands of bases long or hundreds of thousands of bases long or millions of bases long or even longer.

This exonuclease-mediated approach is based on the action of double stranded DNA specific exodeoxyribonuclease activity of E. coli exonuclease III. Substrates for exonuclease III may be generated by subjecting a double stranded polynucleotide to fragmentation. Fragmentation may be achieved by mechanical means (e.g., shearing, sonication, etc.), by enzymatic means (e.g. using restriction enzymes), and by any combination thereof. Fragments of a larger polynucleotide may also be generated by polymerase-mediated synthesis.

Exonuclease III is a 28K monomeric enzyme, product of the xthA gene of E. coli with four known activities: exodeoxyribonuclease (alternatively referred to as exonuclease herein), RNaseH, DNA-3'-phosphatase, and AP endonuclease. The exodeoxyribonuclease activity is specific for double stranded DNA. The mechanism of action is thought to involve enzymatic hydrolysis of DNA from a 3' end progressively towards a 5' direction, with formation of nucleoside 5'-phosphates and a residual single strand. The enzyme does not display efficient hydrolysis of single stranded DNA, single-stranded RNA, or double-stranded RNA; however it degrades RNA in an DNA-RNA hybrid releasing nucleoside 5'-phosphates. The enzyme also releases inorganic phosphate specifically from 3'phosphomonoester groups on DNA, but not from RNA or short oligonucleotides. Removal of these groups converts the terminus into a primer for DNA polymerase action.

Additional examples of enzymes with exonuclease activity include red-alpha and venom phosphodiesterases. Red alpha (redα) gene product (also referred to as lambda exonuclease) is of bacteriophage λ origin. The redα gene is transcribed from the leftward promoter and its product is involved (24 kD) in recombination. Red alpha gene product acts processively from 5'-phosphorylated termini to liberate mononucleotides from duplex DNA (Takahashi & Kobayashi, 1990). Venom phosphodiesterases (Laskowski, 1980) are capable of rapidly opening supercoiled DNA.

Synthetic Ligation Reassembly

In one aspect, the present invention provides a non-stochastic method termed synthetic ligation reassembly (SLR), that is somewhat related to stochastic shuffling, save that the nucleic acid building blocks are not shuffled or concatenated or chimerized randomly, but rather are assembled non-stochastically.

A particularly glaring difference is that the instant SLR method does not depend on the presence of a high level of homology between polynucleotides to be shuffled. In contrast, prior methods, particularly prior stochastic shuffling methods require that presence of a high level of homology, particularly at coupling sites, between polynucleotides to be shuffled. Accordingly these prior methods favor the regeneration of the original progenitor molecules, and are suboptimal for generating large numbers of novel progeny chimeras, particularly full-length progenies. The instant invention, on the other hand, can be used to non-stochastically generate libraries (or sets) of progeny molecules comprised of over $10^{100}$ different chimeras. Conceivably, SLR can even be used to generate libraries comprised of over $10^{1000}$ different progeny chimeras with (no upper limit in sight).

Thus, in one aspect, the present invention provides a method, which method is non-stochastic, of producing a set of finalized chimeric nucleic acid molecules having an overall assembly order that is chosen by design, which method is comprised of the steps of generating by design a plurality of specific nucleic acid building blocks having serviceable mutually compatible ligatable ends, and assembling these nucleic acid building blocks, such that a designed overall assembly order is achieved.

The mutually compatible ligatable ends of the nucleic acid building blocks to be assembled are considered to be "serviceable" for this type of ordered assembly if they enable the building blocks to be coupled in predetermined orders. Thus, in one aspect, the overall assembly order in which the nucleic acid building blocks can be coupled is specified by the design of the ligatable ends and, if more than one assembly step is to be used, then the overall assembly order in which the nucleic acid building blocks can be coupled is also specified by the sequential order of the assembly step(s). An exemplary assembly process is comprised of 2 sequential steps to achieve a designed (non-stochastic) overall assembly order for five nucleic acid building blocks. In a preferred embodiment of this invention, the annealed building pieces are treated with an enzyme, such as a ligase (e.g. T4 DNA ligase), achieve covalent bonding of the building pieces.

In a preferred embodiment, the design of nucleic acid building blocks is obtained upon analysis of the sequences of a set of progenitor nucleic acid templates that serve as a basis for producing a progeny set of finalized chimeric nucleic acid molecules. These progenitor nucleic acid templates thus serve as a source of sequence information that aids in the design of the nucleic acid building blocks that are to be mutagenized, i.e. chimerized or shuffled.

In one exemplification, this invention provides for the chimerization of a family of related genes and their encoded family of related products.

Thus according to one aspect of this invention, the sequences of a plurality of progenitor nucleic acid templates are aligned in order to select one or more demarcation points, which demarcation points can be located at an area of homology, and are comprised of one or more nucleotides, and which demarcation points are shared by at least two of the progenitor templates. The demarcation points can be used to delineate the boundaries of nucleic acid building blocks to be generated. Thus, the demarcation points identified and selected in the progenitor molecules serve as potential chimerization points in the assembly of the progeny molecules.

Preferably a serviceable demarcation point is an area of homology (comprised of at least one homologous nucleotide base) shared by at least two progenitor templates. More preferably a serviceable demarcation point is an area of homology that is shared by at least half of the progenitor templates. More preferably still a serviceable demarcation point is an area of homology that is shared by at least two thirds of the progenitor templates. Even more preferably a serviceable demarcation points is an area of homology that is shared by at least three fourths of the progenitor templates. Even more preferably still a serviceable demarcation points is an area of homology that is shared by at almost all of the progenitor templates. Even more preferably still a serviceable demarcation point is an area of homology that is shared by all of the progenitor templates.

The process of designing nucleic acid building blocks and of designing the mutually compatible ligatable ends of the nucleic acid building blocks to be assembled involves the alignment of a set of progenitor templates revealing several naturally occurring demarcation points, and the identification of demarcation points shared by these templates helping to non-stochastically determine the building blocks to be generated and used for the generation of the progeny chimeric molecules.

In a preferred embodiment, this invention provides that the ligation reassembly process is performed exhaustively in order to generate an exhaustive library. In other words, all possible ordered combinations of the nucleic acid building blocks are represented in the set of finalized chimeric nucleic acid molecules. At the same time, in a particularly preferred embodiment, the assembly order (i.e. the order of assembly of each building block in the 5' to 3 sequence of each finalized chimeric nucleic acid) in each combination is by design (or non-stochastic). Because of the non-stochastic nature of this invention, the possibility of unwanted side products is greatly reduced.

In another preferred embodiment, this invention provides that, the ligation reassembly process is performed systematically, for example in order to generate a systematically compartmentalized library, with compartments that can be screened systematically, e.g. one by one. In other words this invention provides that, through the selective and judicious use of specific nucleic acid building blocks, coupled with the selective and judicious use of sequentially stepped assembly reactions, an experimental design can be achieved where specific sets of progeny products are made in each of several reaction vessels. This allows a systematic examination and screening procedure to be performed. Thus, it allows a potentially very large number of progeny molecules to be examined systematically in smaller groups.

Because of its ability to perform chimerizations in a manner that is highly flexible yet exhaustive and systematic as well, particularly when there is a low level of homology among the progenitor molecules, the instant invention provides for the generation of a library (or set) comprised of a large number of progeny molecules. Because of the non-stochastic nature of the instant ligation reassembly invention, the progeny molecules generated preferably comprise a library of finalized chimeric nucleic acid molecules having an overall assembly order that is chosen by design. In a particularly preferred embodiment of this invention, such a generated library is comprised of preferably greater than $10^3$ different progeny molecular species, more preferably greater than $10^5$ different progeny molecular species, more preferably still greater than $10^{10}$ different progeny molecular species, more preferably still greater than $10^{15}$ different progeny molecular species, more preferably still greater than $10^{20}$ different progeny molecular species, more preferably still greater than $10^{30}$ different progeny molecular species, more preferably still greater than $10^{40}$ different progeny molecular species, more preferably still greater than $10^{50}$ different progeny molecular species, more preferably still greater than $10^{60}$ different progeny molecular species, more preferably still greater than $10^{70}$ different progeny molecular species, more preferably still greater than $10^{80}$ different progeny molecular species, more preferably still greater than $10^{100}$ different progeny molecular species, more preferably still greater than $10^{110}$ different progeny molecular species, more preferably still greater than $10^{120}$ different progeny molecular species, more preferably still greater than $10^{130}$ different progeny molecular species, more preferably still greater than $10^{140}$ different progeny molecular species, more preferably still greater than $10^{150}$ different progeny molecular species, more preferably still greater than $10^{175}$ different progeny molecular species, more preferably still greater than $10^{200}$ different progeny molecular species, more preferably still greater than $10^{300}$ different progeny molecular species, more preferably still greater than $10^{400}$ different progeny molecular species, more referably still greater than $10^{500}$ different progeny molecular species, and even more preferably still greater than $10^{1000}$ different progeny molecular species.

In one aspect, a set of finalized chimeric nucleic acid molecules, produced as described is comprised of a polynucleotide encoding a polypeptide. According to one preferred embodiment, this polynucleotide is a gene, which may be a man-made gene. According to another preferred embodiment, this polynucleotide is a gene pathway, which may be a man-made gene pathway. This invention provides that one or more man-made genes generated by this invention may be incorporated into a man-made gene pathway, such as pathway operable in a eukaryotic organism (including a plant).

It is appreciated that the power of this invention is exceptional, as there is much freedom of choice and control regarding the selection of demarcation points, the size and number of the nucleic acid building blocks, and the size and design of the couplings. It is appreciated, furthermore, that the requirement for intermolecular homology is highly relaxed for the operability of this invention. In fact, demarcation points can even be chosen in areas of little or no intermolecular homology. For example, because of codon wobble, i.e. the degeneracy of codons, nucleotide substitutions can be introduced into nucleic acid building blocks without altering the amino acid originally encoded in the corresponding progenitor template. Alternatively, a codon can be altered such that the coding for an originally amino acid is altered. This invention provides that such substitutions can be introduced into the nucleic acid building block in order to increase the incidence of intermolecularly homologous demarcation points and thus to allow an increased number of couplings to be achieved among the building blocks, which in turn allows a greater number of progeny chimeric molecules to be generated.

In another exemplification, the synthetic nature of the step in which the building blocks are generated allows the design and introduction of nucleotides (e.g. one or more nucleotides, which may be, for example, codons or introns or regulatory sequences) that can later be optionally removed in an in vitro process (e.g. by mutagenesis) or in an in vivo process (e.g. by utilizing the gene splicing ability of a host organism). It is appreciated that in many instances the introduction of these nucleotides may also be desirable for many other reasons in addition to the potential benefit of creating a serviceable demarcation point.

Thus, according to another embodiment, this invention provides that a nucleic acid building block can be used to introduce an intron. Thus, this invention provides that functional introns may be introduced into a man-made gene of this invention. This invention also provides that functional introns may be introduced into a man-made gene pathway of this invention. Accordingly, this invention provides for the generation of a chimeric polynucleotide that is a man-made gene containing one (or more) artificially introduced intron(s).

Accordingly, this invention also provides for the generation of a chimeric polynucleotide that is a man-made gene pathway containing one (or more) artificially introduced intron(s). Preferably, the artificially introduced intron(s) are functional in one or more host cells for gene splicing much in the way that naturally-occurring introns serve functionally in gene splicing. This invention provides a process of producing man-made intron-containing polynucleotides to be introduced into host organisms for recombination and/or splicing.

The ability to achieve chimerizations, using couplings as described herein, in areas of little or no homology among the progenitor molecules, is particularly useful, and in fact critical, for the assembly of novel gene pathways. This invention thus provides for the generation of novel man-made gene pathways using synthetic ligation reassembly. In a particular aspect, this is achieved by the introduction of regulatory sequences, such as promoters, that are operable in an intended host, to confer operability to a novel gene pathway when it is introduced into the intended host. In a particular exemplification, this invention provides for the generation of novel man-made gene pathways that is operable in a plurality of intended hosts (e.g. in a microbial organism as well as in a plant cell).

This can be achieved, for example, by the introduction of a plurality of regulatory sequences, comprised of a regulatory sequence that is operable in a first intended host and a regulatory sequence that is operable in a second intended host. A similar process can be performed to achieve operability of a gene pathway in a third intended host species, etc. The number of intended host species can be each integer from 1 to 10 or alternatively over 10. Alternatively, for example, operability of a gene pathway in a plurality of intended hosts can be achieved by the introduction of a regulatory sequence having intrinsic operability in a plurality of intended hosts.

Thus, according to a particular embodiment, this invention provides that a nucleic acid building block can be used to introduce a regulatory sequence, particularly a regulatory sequence for gene expression. Preferred regulatory sequences include, but are not limited to, those that are man-made, and those found in archeal, bacterial, eukaryotic (including mitochondrial), viral, and prionic or prion-like organisms. Preferred regulatory sequences include but are not limited to, promoters, operators, and activator binding sites. Thus, this invention provides that functional regulatory sequences may be introduced into a man-made gene of this invention. This invention also provides that functional regulatory sequences may be introduced into a man-made gene pathway of this invention.

Accordingly, this invention provides for the generation of a chimeric polynucleotide that is a man-made gene containing one (or more) artificially introduced regulatory sequence(s). Accordingly, this invention also provides for the generation of a chimeric polynucleotide that is a man-made gene pathway containing one (or more) artificially introduced regulatory sequence(s). Preferably, an artificially introduced regulatory sequence(s) is operatively linked to one or more genes in the man-made polynucleotide, and are functional in one or more host cells.

Preferred bacterial promoters that are serviceable for this invention include lacI, lacZ, T3, T7, gpt, lambda $P_R$, $P_L$ and trp. Serviceable eukaryotic promoters include CMV immediate early, HSV thymidine kinase, early and late SV40, LTRs from retrovirus, and mouse metallothionein-I. Particular plant regulatory sequences include promoters active in directing transcription in plants, either constitutively or stage and/or tissue specific, depending on the use of the plant or parts thereof. These promoters include, but are not limited to promoters showing constitutive expression, such as the 35S promoter of Cauliflower Mosaic Virus (CaMV) (Guilley et al., 1982), those for leaf-specific expression, such as the promoter of the ribulose bisphosphate carboxylase small subunit gene (Coruzzi et al., 1984), those for root-specific expression, such as the promoter from the glutamine synthase gene (Tingey et al., 1987), those for seed-specific expression, such as the cruciferin A promoter from *Brassica napus* (Ryan et al., 1989), those for tuber-specific expression, such as the class-I patatin promoter from potato (Rocha-Sasa et al., 1989; Wenzler et al., 1989) or those for fruit-specific expression, such as the polygalacturonase (PG) promoter from tomato (Bird et al., 1988).

Other regulatory sequences that are preferred for this invention include terminator sequences and polyadenylation signals and any such sequence functioning as such in plants, the choice of which is within the level of the skilled artisan. An example of such sequences is the 3' flanking region of the nopaline synthase (nos) gene of *Agrobacterium tumefaciens* (Bevan, 1984). The regulatory sequences may also include enhancer sequences, such as found in the 35S promoter of CaMV, and mRNA stabilizing sequences such as the leader sequence of Alfalfa Mosaic Cirus (A1MV) RNA4 (Brederode et al., 1980) or any other sequences functioning in a like manner.

A man-made genes produced using this invention can also serve as a substrate for recombination with another nucleic acid. Likewise, a man-made gene pathway produced using this invention can also serve as a substrate for recombination with another nucleic acid. In a preferred instance, the recombination is facilitated by, or occurs at, areas of homology between the man-made intron-containing gene and a nucleic acid with serves as a recombination partner. In a particularly preferred instance, the recombination partner may also be a nucleic acid generated by this invention, including a man-made gene or a man-made gene pathway. Recombination may be facilitated by or may occur at areas of homology that exist at the one (or more) artificially introduced intron(s) in the man-made gene.

The synthetic ligation reassembly method of this invention utilizes a plurality of nucleic acid building blocks, each of which preferably has two ligatable ends. The two ligatable ends on each nucleic acid building block may be two blunt ends (i.e. each having an overhang of zero nucleotides), or preferably one blunt end and one overhang, or more preferably still two overhangs.

A serviceable overhang for this purpose may be a 3' overhang or a 5' overhang. Thus, a nucleic acid building block may have a 3' overhang or alternatively a 5' overhang or alternatively two 3' overhangs or alternatively two 5' overhangs. The overall order in which the nucleic acid building blocks are assembled to form a finalized chimeric nucleic acid molecule is determined by purposeful experimental design and is not random.

According to one preferred embodiment, a nucleic acid building block is generated by chemical synthesis of two single-stranded nucleic acids (also referred to as single-stranded oligos) and contacting them so as to allow them to anneal to form a double-stranded nucleic acid building block.

A double-stranded nucleic acid building block can be of variable size. The sizes of these building blocks can be small or large depending on the choice of the experimenter. Preferred sizes for building block range from 1 base pair (not including any overhangs) to 100,000 base pairs (not including any overhangs). Other preferred size ranges are also provided, which have lower limits of from 1 bp to 10,000 bp (including every integer value in between) and upper limits of from 2 bp to 100,000 bp (including every integer value in between).

It is appreciated that current methods of polymerase-based amplification can be used to generate double-stranded nucleic acids of up to thousands of base pairs, if not tens of thousands of base pairs, in length with high fidelity. Chemical synthesis (e.g. phosphoramidite-based) can be used to generate nucleic acids of up to hundreds of nucleotides in length with high fidelity; however, these can be assembled, e.g. using overhangs or sticky ends, to form double-stranded nucleic acids of up to thousands of base pairs, if not tens of thousands of base pairs, in length if so desired.

A combination of methods (e.g. phosphoramidite-based chemical synthesis and PCR) can also be used according to this invention. Thus, nucleic acid building block made by different methods can also be used in combination to generate a progeny molecule of this invention.

The use of chemical synthesis to generate nucleic acid building blocks is particularly preferred in this invention & is advantageous for other reasons as well, including procedural safety and ease. No cloning or harvesting or actual handling of any biological samples is required. The design of the nucleic acid building blocks can be accomplished on paper. Accordingly, this invention teaches an advance in procedural safety in recombinant technologies.

Nonetheless, according to one preferred embodiment, a double-stranded nucleic acid building block according to this invention may also be generated by polymerase-based amplification of a polynucleotide template. In a non-limiting exemplification, a first polymerase-based amplification reaction using a first set of primers, $F_2$ and $R_1$, is used to generate a blunt-ended product (Reaction 1, Product 1), which is essentially identical to Product A. A second polymerase-based amplification reaction using a second set of primers, $F_1$ and $R_2$, is used to generate a blunt-ended product (Reaction 2, Product 2), which is essentially identical to Product B. These two products are mixed and allowed to melt and anneal, generating potentially useful double-stranded nucleic acid building blocks with two overhangs. In the example, the product with the 3' overhangs (Product C) is selected by nuclease-based degradation of the other 3 products using a 3' acting exonuclease, such as exonuclease III. It is appreciated that a 5' acting exonuclease (e.g. red alpha) may be also be used, for example to select Product D instead. It is also appreciated that other selection means can also be used, including hybridization-based means, and that these means can incorporate a further means, such as a magnetic bead-based means, to facilitate separation of the desired product.

Many other methods exist by which a double-stranded nucleic acid building block can be generated that is serviceable for this invention; and these are known in the art and can be readily performed by the skilled artisan.

According to particularly preferred embodiment, a double-stranded nucleic acid building block that is serviceable for this invention is generated by first generating two single stranded nucleic acids and allowing them to anneal to form a double-stranded nucleic acid building block. The two strands of a double-stranded nucleic acid building block may be complementary at every nucleotide apart from any that form an overhang; thus containing no mismatches, apart from any overhang(s). According to another embodiment, the two strands of a double-stranded nucleic acid building block are complementary at fewer than every nucleotide apart from any that form an overhang. Thus, according to this embodiment, a double-stranded nucleic acid building block can be used to introduce codon degeneracy. Preferably the codon degeneracy is introduced using the site-saturation mutagenesis described herein, using one or more N,N,G/T cassettes or alternatively using one or more N,N,N cassettes.

Contained within an exemplary experimental design for achieving an ordered assembly according to this invention are:

1) The design of specific nucleic acid building blocks.
2) The design of specific ligatable ends on each nucleic acid building block.
3) The design of a particular order of assembly of the nucleic acid building blocks.

An overhang may be a 3' overhang or a 5' overhang. An overhang may also have a terminal phosphate group or alternatively may be devoid of a terminal phosphate group (having, e.g., a hydroxyl group instead). An overhang may be comprised of any number of nucleotides. Preferably an overhang is comprised of 0 nucleotides (as in a blunt end) to 10,000 nucleotides. Thus, a wide range of overhang sizes may be serviceable. Accordingly, the lower limit may be each integer from 1-200 and the upper limit may be each integer from 2-10,000. According to a particular exemplification, an overhang may consist of anywhere from 1 nucleotide to 200 nucleotides (including every integer value in between).

The final chimeric nucleic acid molecule may be generated by sequentially assembling 2 or more building blocks at a time until all the designated building blocks have been assembled. A working sample may optionally be subjected to a process for size selection or purification or other selection or enrichment process between the performance of two assembly steps. Alternatively, the final chimeric nucleic acid molecule may be generated by assembling all the designated building blocks at once in one step.

In vivo Shuffling

In an embodiment of in vivo shuffling, the mixed population of the specific nucleic acid sequence is introduced into bacterial or eukaryotic cells under conditions such that at least two different nucleic acid sequences are present in each host cell. The polynucleotides can be introduced into the host cells by a variety of different methods. The host cells can be transformed with the smaller polynucleotides using methods known in the art, for example treatment with calcium chloride. If the polynucleotides are inserted into a phage genome, the host cell can be transfected with the recombinant phage genome having the specific nucleic acid sequences. Alternatively, the nucleic acid sequences can be introduced into the host cell using electroporation, transfection, lipofection, biolistics, conjugation, and the like.

In general, in this embodiment, the specific nucleic acids sequences will be present in vectors, which are capable of stably replicating the sequence in the host cell. In addition, it is contemplated that the vectors will encode a marker gene such that host cells having the vector can be selected. This ensures that the mutated specific nucleic acid sequence can be recovered after introduction into the host cell. However, it is contemplated that the entire mixed population of the specific nucleic acid sequences need not be present on a vector sequence. Rather only a sufficient number of sequences need be cloned into vectors to ensure that after introduction of the polynucleotides into the host cells each host cell contains one vector having at least one specific nucleic acid sequence present therein. It is also contemplated that rather than having a subset of the population of the specific nucleic acids sequences cloned into vectors, this subset may be already stably integrated into the host cell.

It has been found that when two polynucleotides, which have regions of identity are inserted into the host cells homologous recombination occurs between the two polynucleotides. Such recombination between the two mutated specific nucleic acid sequences will result in the production of double or triple hybrids in some situations.

It has also been found that the frequency of recombination is increased if some of the mutated specific nucleic acid sequences are present on linear nucleic acid molecules. Therefore, in a preferred embodiment, some of the specific nucleic acid sequences are present on linear polynucleotides.

After transformation, the host cell transformants are placed under selection to identify those host cell transformants, which contain mutated specific nucleic acid sequences having the qualities desired. For example, if increased resistance to a particular drug is desired then the transformed host cells may be subjected to increased concentrations of the particular drug and those transformants producing mutated proteins able to confer increased drug resistance will be selected. If the enhanced ability of a particular protein to bind to a receptor is desired, then expression of the protein can be induced from the transformants and the resulting protein assayed in a ligand binding assay by methods known in the art to identify that subset of the mutated population which shows enhanced binding to the ligand. Alternatively, the protein can be expressed in another system to ensure proper processing.

Once a subset of the first recombined specific nucleic acid sequences (daughter sequences) having the desired characteristics are identified, they are then subject to a second round of recombination. In the second cycle of recombination, the recombined specific nucleic acid sequences may be mixed with the original mutated specific nucleic acid sequences (parent sequences) and the cycle repeated as described above. In this way a set of second recombined specific nucleic acids sequences can be identified which have enhanced characteristics or encode for proteins having enhanced properties. This cycle can be repeated a number of times as desired.

It is also contemplated that in the second or subsequent recombination cycle, a backcross can be performed. A molecular backcross can be performed by mixing the desired specific nucleic acid sequences with a large number of the wild-type sequence, such that at least one wild-type nucleic acid sequence and a mutated nucleic acid sequence are present in the same host cell after transformation. Recombination with the wild-type specific nucleic acid sequence will eliminate those neutral mutations that may affect unselected characteristics such as immunogenicity but not the selected characteristics.

In another embodiment of this invention, it is contemplated that during the first round a subset of the specific nucleic acid sequences can be generated as smaller polynucleotides by slowing or halting their PCR amplification prior to introduction into the host cell. The size of the polynucleotides must be large enough to contain some regions of identity with the other sequences so as to homologously recombine with the other sequences. The size of the polynucleotides will range from 0.03 kb to 100 kb more preferably from 0.2 kb to 10 kb. It is also contemplated that in subsequent rounds, all of the specific nucleic acid sequences other than the sequences selected from the previous round may be utilized to generate PCR polynucleotides prior to introduction into the host cells.

The shorter polynucleotide sequences can be single-stranded or double-stranded. If the sequences were originally single-stranded and have become double-stranded they can be denatured with heat, chemicals or enzymes prior to insertion into the host cell. The reaction conditions suitable for separating the strands of nucleic acid are well known in the art.

The steps of this process can be repeated indefinitely, being limited only by the number of possible hybrids which can be achieved. After a certain number of cycles, all possible hybrids will have been achieved and further cycles are redundant.

In an embodiment the same mutated template nucleic acid is repeatedly recombined and the resulting recombinants selected for the desired characteristic. Therefore, the initial pool or population of mutated template nucleic acid is cloned into a vector capable of replicating in a bacteria such as *E. coli*. The particular vector is not essential, so long as it is capable of autonomous replication in *E. coli*. In a preferred embodiment, the vector is designed to allow the expression and production of any protein encoded by the mutated specific nucleic acid linked to the vector. It is also preferred that the vector contain a gene encoding for a selectable marker.

The population of vectors containing the pool of mutated nucleic acid sequences is introduced into the *E. coli* host cells. The vector nucleic acid sequences may be introduced by transformation, transfection or infection in the case of phage. The concentration of vectors used to transform the bacteria is such that a number of vectors is introduced into each cell. Once present in the cell, the efficiency of homologous recombination is such that homologous recombination occurs between the various vectors. This results in the generation of hybrids (daughters) having a combination of mutations, which differ from the original parent mutated sequences.

The host cells are then clonally replicated and selected for the marker gene present on the vector. Only those cells having a plasmid will grow under the selection.

The host cells, which contain a vector are then tested for the presence of favorable mutations. Such testing may consist of placing the cells under selective pressure, for example, if the gene to be selected is an improved drug resistance gene. If the vector allows expression of the protein encoded by the mutated nucleic acid sequence, then such selection may include allowing expression of the protein so encoded, isolation of the protein and testing of the protein to determine whether, for example, it binds with increased efficiency to the ligand of interest.

Once a particular daughter mutated nucleic acid sequence has been identified which confers the desired characteristics, the nucleic acid is isolated either already linked to the vector or separated from the vector. This nucleic acid is then mixed with the first or parent population of nucleic acids and the cycle is repeated. It has been shown that by this method nucleic acid sequences having enhanced desired properties could be selected.

In an alternate embodiment, the first generation of hybrids is retained in the cells and the parental mutated sequences are added again to the cells. Accordingly, the first cycle of Embodiment I is conducted as described above. However, after the daughter nucleic acid sequences are identified, the host cells containing these sequences are retained.

The parent mutated specific nucleic acid population, either as polynucleotides or cloned into the same vector is introduced into the host cells already containing the daughter nucleic acids. Recombination is allowed to occur in the cells and the next generation of recombinants, or granddaughters are selected by the methods described above.

This cycle can be repeated a number of times until the nucleic acid or peptide having the desired characteristics is obtained. It is contemplated that in subsequent cycles, the population of mutated sequences, which are added to the preferred hybrids may come from the parental hybrids or any subsequent generation.

In an alternative embodiment, the invention provides a method of conducting a "molecular" backcross of the obtained recombinant specific nucleic acid in order to eliminate any neutral mutations. Neutral mutations are those mutations, which do not confer onto the nucleic acid or peptide the desired properties. Such mutations may however confer on the nucleic acid or peptide undesirable characteristics. Accordingly, it is desirable to eliminate such neutral mutations. The method of this invention provides a means of doing so. In this embodiment, after the hybrid nucleic acid, having the desired characteristics, is obtained by the methods of the embodiments, the nucleic acid, the vector having the nucleic acid or the host cell containing the vector and nucleic acid is isolated.

The nucleic acid or vector is then introduced into the host cell with a large excess of the wild-type nucleic acid. The nucleic acid of the hybrid and the nucleic acid of the wild-type sequence are allowed to recombine. The resulting recombinants are placed under the same selection as the hybrid nucleic acid. Only those recombinants, which retained the desired characteristics, will be selected. Any silent mutations, which do not provide the desired characteristics, will be lost through recombination with the wild-type DNA. This cycle can be repeated a number of times until all of the silent mutations are eliminated. Thus the methods of this invention can be used in a molecular backcross to eliminate unnecessary or silent mutations.

Utility

The in vivo recombination method of this invention can be performed blindly on a pool of unknown hybrids or alleles of a specific polynucleotide or sequence. However, it is not necessary to know the actual DNA or RNA sequence of the specific polynucleotide.

The approach of using recombination within a mixed population of genes can be useful for the generation of useful proteins. This approach may be used to generate proteins having altered specificity or activity. The approach may also be useful for the generation of hybrid nucleic acid sequences, for example, promoter regions, introns, exons, enhancer sequences, untranslated regions or untranslated regions of genes. Thus this approach may be used to generate genes having increased rates of expression. This approach may also be useful in the study of repetitive DNA sequences. Finally, this approach may be useful to mutate ribozymes or aptamers.

Scaffold-like regions separating regions of diversity in proteins may be particularly suitable for the methods of this invention. The conserved scaffold determines the overall folding by self-association, while displaying relatively unrestricted loops that mediate the specific binding. Examples of such scaffolds are the immunoglobulin beta barrel, and the four-helix bundle. The methods of this invention can be used to create scaffold-like proteins with various combinations of mutated sequences for binding.

The equivalents of some standard genetic matings may also be performed by the methods of this invention. For example, a "molecular" backcross can be performed by repeated mixing of the hybrid's nucleic acid with the wild-type nucleic acid while selecting for the mutations of interest. As in traditional breeding, this approach can be used to combine phenotypes from different sources into a background of choice. It is useful, for example, for the removal of neutral mutations that affect unselected characteristics (i.e. immunogenicity). Thus it can be useful to determine which mutations in a protein are involved in the enhanced biological activity and which are not.

Peptide Display Methods

The present method can be used to shuffle, by in vitro and/or in vivo recombination by any of the disclosed methods, and in any combination, polynucleotide sequences selected by peptide display methods, wherein an associated polynucleotide encodes a displayed peptide which is screened for a phenotype (e.g., for affinity for a predetermined receptor (ligand).

An increasingly important aspect of molecular biology is the identification of peptide structures, including the primary amino acid sequences, of peptides or peptidomimetics that interact with biological macromolecules. One method of identifying peptides that possess a desired structure or functional property, such as binding to a predetermined biological macromolecule (e.g., a receptor), involves the screening of a large library or peptides for individual library members which possess the desired structure or functional property conferred by the amino acid sequence of the peptide.

In addition to direct chemical synthesis methods for generating peptide libraries, several recombinant DNA methods also have been reported. One type involves the display of a peptide sequence, antibody, or other protein on the surface of a bacteriophage particle or cell. Generally, in these methods each bacteriophage particle or cell serves as an individual library member displaying a single species of displayed peptide in addition to the natural bacteriophage or cell protein sequences. Each bacteriophage or cell contains the nucleotide sequence information encoding the particular displayed peptide sequence; thus, the displayed peptide sequence can be ascertained by nucleotide sequence determination of an isolated library member.

A well-known peptide display method involves the presentation of a peptide sequence on the surface of a filamentous bacteriophage, typically as a fusion with a bacteriophage coat protein. The bacteriophage library can be incubated with an immobilized, predetermined macromolecule or small molecule (e.g., a receptor) so that bacteriophage particles which present a peptide sequence that binds to the immobilized macromolecule can be differentially partitioned from those that do not present peptide sequences that bind to the predetermined macromolecule. The bacteriophage particles (i.e., library members), which are bound to the immobilized macromolecule are then recovered and replicated to amplify the selected bacteriophage sub-population for a subsequent round of affinity enrichment and phage replication. After several rounds of affinity enrichment and phage replication, the bacteriophage library members that are thus selected are isolated and the nucleotide sequence encoding the displayed peptide sequence is determined, thereby identifying the sequence(s) of peptides that bind to the predetermined macromolecule (e.g., receptor). Such methods are further described in PCT patent publications WO 91/17271, WO 91/18980, WO 91/19818 and WO 93/08278.

The latter PCT publication describes a recombinant DNA method for the display of peptide ligands that involves the production of a library of fusion proteins with each fusion protein composed of a first polypeptide portion, typically comprising a variable sequence, that is available for potential binding to a predetermined macromolecule, and a second polypeptide portion that binds to DNA, such as the DNA vector encoding the individual fusion protein. When transformed host cells are cultured under conditions that allow for expression of the fusion protein, the fusion protein binds to the DNA vector encoding it. Upon lysis of the host cell, the fusion protein/vector DNA complexes can be screened against a predetermined macromolecule in much the same way as bacteriophage particles are screened in the phage-based display system, with the replication and sequencing of the DNA vectors in the selected fusion protein/vector DNA complexes serving as the basis for identification of the selected library peptide sequence(s).

Other systems for generating libraries of peptides and like polymers have aspects of both the recombinant and in vitro chemical synthesis methods. In these hybrid methods, cell-free enzymatic machinery is employed to accomplish the in vitro synthesis of the library members (i.e., peptides or polynucleotides). In one type of method, RNA molecules with the ability to bind a predetermined protein or a predetermined dye molecule were selected by alternate rounds of selection and PCR amplification (Tuerk and Gold, 1990; Ellington and Szostak, 1990). A similar technique was used to identify DNA sequences, which bind a predetermined human transcription factor (Thiesen and Bach, 1990; Beaudry and Joyce, 1992; PCT patent publications WO 92/05258 and WO 92/14843). In a similar fashion, the technique of in vitro translation has been used to synthesize proteins of interest and has been proposed as a method for generating large libraries of peptides. These methods which rely upon in vitro translation, generally comprising stabilized polysome complexes, are described further in PCT patent publications WO 88/08453, WO 90/05785, WO 90/07003, WO 91/02076, WO 91/05058, and WO 92/02536. Applicants have described methods in which library members comprise a fusion protein having a first polypeptide portion with DNA binding activity and a second polypeptide portion having the library member unique peptide sequence; such methods are suitable for use in cell-free in vitro selection formats, among others.

The displayed peptide sequences can be of varying lengths, typically from 3-5000 amino acids long or longer, frequently from 5-100 amino acids long, and often from about 8-15 amino acids long. A library can comprise library members having varying lengths of displayed peptide sequence, or may comprise library members having a fixed length of displayed peptide sequence. Portions or all of the displayed peptide sequence(s) can be random, pseudorandom, defined set kernal, fixed, or the like. The present display methods include methods for in vitro and in vivo display of single-chain antibodies, such as nascent scFv on polysomes or scfv displayed on phage, which enable large-scale screening of scfv libraries having broad diversity of variable region sequences and binding specificities.

The present invention also provides random, pseudorandom, and defined sequence framework peptide libraries and methods for generating and screening those libraries to identify useful compounds (e.g., peptides, including single-chain antibodies) that bind to receptor molecules or epitopes of interest or gene products that modify peptides or RNA in a desired fashion. The random, pseudorandom, and defined sequence framework peptides are produced from libraries of peptide library members that comprise displayed peptides or displayed single-chain antibodies attached to a polynucleotide template from which the displayed peptide was synthesized. The mode of attachment may vary according to the specific embodiment of the invention selected, and can include encapsulation in a phage particle or incorporation in a cell.

A method of affinity enrichment allows a very large library of peptides and single-chain antibodies to be screened and the polynucleotide sequence encoding the desired peptide(s) or single-chain antibodies to be selected. The polynucleotide can then be isolated and shuffled to recombine combinatorially the amino acid sequence of the selected peptide(s) (or predetermined portions thereof) or single-chain antibodies (or just VHI, VLI or CDR portions thereof). Using these methods, one can identify a peptide or single-chain antibody as having a desired binding affinity for a molecule and can exploit the process of shuffling to converge rapidly to a desired high-affinity peptide or scfv. The peptide or antibody can then be synthesized in bulk by conventional means for any suitable use (e.g., as a therapeutic or diagnostic agent).

A significant advantage of the present invention is that no prior information regarding an expected ligand structure is required to isolate peptide ligands or antibodies of interest. The peptide identified can have biological activity, which is meant to include at least specific binding affinity for a selected receptor molecule and, in some instances, will further include the ability to block the binding of other compounds, to stimulate or inhibit metabolic pathways, to act as a signal or messenger, to stimulate or inhibit cellular activity, and the like.

The present invention also provides a method for shuffling a pool of polynucleotide sequences selected by affinity screening a library of polysomes displaying nascent peptides (including single-chain antibodies) for library members which bind to a predetermined receptor (e.g., a mammalian proteinaceous receptor such as, for example, a peptidergic hormone receptor, a cell surface receptor, an intracellular protein which binds to other protein(s) to form intracellular protein complexes such as hetero-dimers and the like) or epitope (e.g., an immobilized protein, glycoprotein, oligosaccharide, and the like).

Polynucleotide sequences selected in a first selection round (typically by affinity selection for binding to a receptor (e.g., a ligand)) by any of these methods are pooled and the pool(s) is/are shuffled by in vitro and/or in vivo recombination to produce a shuffled pool comprising a population of recombined selected polynucleotide sequences. The recombined selected polynucleotide sequences are subjected to at least one subsequent selection round. The polynucleotide sequences selected in the subsequent selection round(s) can be used directly, sequenced, and/or subjected to one or more additional rounds of shuffling and subsequent selection. Selected sequences can also be back-crossed with polynucleotide sequences encoding neutral sequences (i.e., having insubstantial functional effect on binding), such as for example by back-crossing with a wild-type or naturally-occurring sequence substantially identical to a selected sequence to produce native-like functional peptides, which may be less immunogenic. Generally, during back-crossing subsequent selection is applied to retain the property of binding to the predetermined receptor (ligand).

Prior to or concomitant with the shuffling of selected sequences, the sequences can be mutagenized. In one embodiment, selected library members are cloned in a prokaryotic vector (e.g., plasmid, phagemid, or bacteriophage) wherein a collection of individual colonies (or plaques) representing discrete library members is produced. Individual selected library members can then be manipulated (e.g., by site-directed mutagenesis, cassette mutagenesis, chemical mutagenesis, PCR mutagenesis, and the like) to generate a collection of library members representing a kernal of sequence diversity based on the sequence of the selected library member. The sequence of an individual selected library member or pool can be manipulated to incorporate random mutation, pseudorandom mutation, defined kernal mutation (i.e., comprising variant and invariant residue positions and/or comprising variant residue positions which can comprise a residue selected from a defined subset of amino acid residues), codon-based mutation, and the like, either segmentally or over the entire length of the individual selected library member sequence. The mutagenized selected library members are then shuffled by in vitro and/or in vivo recombinatorial shuffling as disclosed herein.

The invention also provides peptide libraries comprising a plurality of individual library members of the invention, wherein (1) each individual library member of said plurality comprises a sequence produced by shuffling of a pool of selected sequences, and (2) each individual library member comprises a variable peptide segment sequence or single-chain antibody segment sequence which is distinct from the variable peptide segment sequences or single-chain antibody sequences of other individual library members in said plurality (although some library members may be present in more than one copy per library due to uneven amplification, stochastic probability, or the like).

The invention also provides a product-by-process, wherein selected polynucleotide sequences having (or encoding a peptide having) a predetermined binding specificity are formed by the process of: (1) screening a displayed peptide or displayed single-chain antibody library against a predetermined receptor (e.g., ligand) or epitope (e.g., antigen macromolecule) and identifying and/or enriching library members which bind to the predetermined receptor or epitope to produce a pool of selected library members, (2) shuffling by recombination the selected library members (or amplified or cloned copies thereof) which binds the predetermined epitope and has been thereby isolated and/or enriched from the library to generate a shuffled library, and (3) screening the shuffled library against the predetermined receptor (e.g., ligand) or epitope (e.g., antigen macromolecule) and identifying and/or enriching shuffled library members which bind to the predetermined receptor or epitope to produce a pool of selected shuffled library members.

Antibody Display and Screening Methods

The present method can be used to shuffle, by in vitro and/or in vivo recombination by any of the disclosed methods, and in any combination, polynucleotide sequences selected by antibody display methods, wherein an associated polynucleotide encodes a displayed antibody which is screened for a phenotype (e.g., for affinity for binding a predetermined antigen (ligand).

Various molecular genetic approaches have been devised to capture the vast immunological repertoire represented by the extremely large number of distinct variable regions, which can be present in immunoglobulin chains. The naturally-occurring germ line immunoglobulin heavy chain locus is composed of separate tandem arrays of variable segment genes located upstream of a tandem array of diversity segment genes, which are themselves located upstream of a tandem array of joining (i) region genes, which are located upstream of the constant region genes. During B lymphocyte development, V-D-J rearrangement occurs wherein a heavy chain variable region gene (VH) is formed by rearrangement to form a fused D segment followed by rearrangement with a V segment to form a V-D-J joined product gene which, if productively rearranged, encodes a functional variable region (VH) of a heavy chain. Similarly, light chain loci rearrange one of several V segments with one of several J segments to form a gene encoding the variable region (VL) of a light chain.

The vast repertoire of variable regions possible in immunoglobulins derives in part from the numerous combinatorial possibilities of joining V and i segments (and, in the case of heavy chain loci, D segments) during rearrangement in B cell development. Additional sequence diversity in the heavy chain variable regions arises from non-uniform rearrangements of the D segments during V-D-J joining and from N region addition. Further, antigen-selection of specific B cell clones selects for higher affinity variants having non-germline mutations in one or both of the heavy and light chain variable regions; a phenomenon referred to as "affinity maturation" or "affinity sharpening". Typically, these "affinity sharpening" mutations cluster in specific areas of the variable region, most commonly in the complementarity-determining regions (CDRs).

In order to overcome many of the limitations in producing and identifying high-affinity immunoglobulins through antigen-stimulated β cell development (i.e., immunization), various prokaryotic expression systems have been developed that can be manipulated to produce combinatorial antibody libraries which may be screened for high-affinity antibodies to specific antigens. Recent advances in the expression of antibodies in Escherichia coli and bacteriophage systems (see "alternative peptide display methods", infra) have raised the possibility that virtually any specificity can be obtained by either cloning antibody genes from characterized hybridomas or by de novo selection using antibody gene libraries (e.g., from Ig cDNA).

Combinatorial libraries of antibodies have been generated in bacteriophage lambda expression systems which may be screened as bacteriophage plaques or as colonies of lysogens (Huse et al, 1989; Caton and Koprowski, 1990; Mullinax et al, 1990; Persson et al, 1991). Various embodiments of bacteriophage antibody display libraries and lambda phage expression libraries have been described (Kang et al, 1991; Clackson et al, 1991; McCafferty et al, 1990; Burton et al, 1991; Hoogenboom et al, 1991; Chang et al, 1991; Breitling et al, 1991; Marks et al, 1991, p. 581; Barbas et al, 1992; Hawkins and Winter, 1992; Marks et al, 1992, p. 779; Marks et al, 1992, p. 16007; and Lowman et al, 1991; Lerner et al, 1992; all incorporated herein by reference). Typically, a bacteriophage antibody display library is screened with a receptor (e.g., polypeptide, carbohydrate, glycoprotein, nucleic acid) that is immobilized (e.g., by covalent linkage to a chromatography resin to enrich for reactive phage by affinity chromatography) and/or labeled (e.g., to screen plaque or colony lifts).

One particularly advantageous approach has been the use of so-called single-chain fragment variable (scfv) libraries (Marks et al, 1992, p. 779; Winter and Milstein, 1991; Clackson et al, 1991; Marks et al, 1991, p. 581; Chaudhary et al, 1990; Chiswell et al, 1992; McCafferty et al, 1990; and Huston et al, 1988). Various embodiments of scfv libraries displayed on bacteriophage coat proteins have been described.

Beginning in 1988, single-chain analogues of Fv fragments and their fusion proteins have been reliably generated by antibody engineering methods. The first step generally involves obtaining the genes encoding VH and VL domains with desired binding properties; these V genes may be isolated from a specific hybridoma cell line, selected from a combinatorial V-gene library, or made by V gene synthesis. The single-chain Fv is formed by connecting the component V genes with an oligonucleotide that encodes an appropriately designed linker peptide, such as (Gly-Gly-Gly-Gly-Ser)3 or equivalent linker peptide(s). The linker bridges the C-terminus of the first V region and N-terminus of the second, ordered as either VH-linker-VL or VL-linker-VH' In principle, the scfv binding site can faithfully replicate both the affinity and specificity of its parent antibody combining site.

Thus, scfv fragments are comprised of VH and VL domains linked into a single polypeptide chain by a flexible linker peptide. After the scfv genes are assembled, they are cloned into a phagemid and expressed at the tip of the M13 phage (or similar filamentous bacteriophage) as fusion proteins with the bacteriophage PIII (gene 3) coat protein. Enriching for phage expressing an antibody of interest is accomplished by panning the recombinant phage displaying a population scfv for binding to a predetermined epitope (e.g., target antigen, receptor).

The linked polynucleotide of a library member provides the basis for replication of the library member after a screening or selection procedure, and also provides the basis for the determination, by nucleotide sequencing, of the identity of the displayed peptide sequence or VH and VL amino acid sequence. The displayed peptide (s) or single-chain antibody (e.g., scfv) and/or its VH and VL domains or their CDRs can be cloned and expressed in a suitable expression system. Often polynucleotides encoding the isolated VH and VL domains will be ligated to polynucleotides encoding constant regions (CH and CL) to form polynucleotides encoding complete antibodies (e.g., chimeric or fully-human), antibody fragments, and the like. Often polynucleotides encoding the isolated CDRs will be grafted into polynucleotides encoding a suitable variable region framework (and optionally constant regions) to form polynucleotides encoding complete antibodies (e.g., humanized or fully-human), antibody fragments, and the like. Antibodies can be used to isolate preparative quantities of the antigen by immunoaffinity chromatography. Various other uses of such antibodies are to diagnose and/or stage disease (e.g., neoplasia) and for therapeutic application to treat disease, such as for example: neoplasia, autoimmune disease, AIDS, cardiovascular disease, infections, and the like.

Various methods have been reported for increasing the combinatorial diversity of a scfv library to broaden the repertoire of binding species (idiotype spectrum) The use of PCR has permitted the variable regions to be rapidly cloned either from a specific hybridoma source or as a gene library from non-immunized cells, affording combinatorial diversity in the assortment of VH and VL cassettes which can be combined. Furthermore, the VH and VL cassettes can themselves be diversified, such as by random, pseudorandom, or directed mutagenesis. Typically, VH and VL cassettes are diversified in or near the complementarity-determining regions (CDRS), often the third CDR, CDR3. Enzymatic inverse PCR mutagenesis has been shown to be a simple and reliable method for constructing relatively large libraries of scfv site-directed hybrids (Stemmer et al, 1993), as has error-prone PCR and chemical mutagenesis (Deng et al, 1994). Riechmann (Riechmann et al, 1993) showed semi-rational design of an antibody scfv fragment using site-directed randomization by degenerate oligonucleotide PCR and subsequent phage display of the resultant scfv hybrids. Barbas (Barbas et al, 1992) attempted to circumvent the problem of limited repertoire sizes resulting from using biased variable region sequences by randomizing the sequence in a synthetic CDR region of a human tetanus toxoid-binding Fab.

CDR randomization has the potential to create approximately $1 \times 10^{20}$ CDRs for the heavy chain CDR3 alone, and a roughly similar number of variants of the heavy chain CDR1 and CDR2, and light chain CDR1-3 variants. Taken individually or together, the combination possibilities of CDR randomization of heavy and/or light chains requires generating a prohibitive number of bacteriophage clones to produce a clone library representing all possible combinations, the vast majority of which will be non-binding. Generation of such large numbers of primary transformants is not feasible with current transformation technology and bacteriophage display systems. For example, Barbas (Barbas et al, 1992) only generated $5 \times 10^7$ transformants, which represents only a tiny fraction of the potential diversity of a library of thoroughly randomized CDRS.

If it were possible to generate scfv libraries having broader antibody diversity and overcoming many of the limitations of conventional CDR mutagenesis and randomization methods, which can cover only a very tiny fraction of the potential sequence combinations, the number and quality of scfv antibodies suitable for therapeutic and diagnostic use could be vastly improved. To address this, the in vitro and in vivo shuffling methods of the invention are used to recombine CDRs, which have been obtained (typically via PCR amplification or cloning) from nucleic acids obtained from selected displayed antibodies. Such displayed antibodies can be displayed on cells, on bacteriophage particles, on polysomes, or any suitable antibody display system wherein the antibody is associated with its encoding nucleic acid(s). In a variation, the CDRs are initially obtained from mRNA (or cDNA) from antibody-producing cells (e.g., plasma cells/splenocytes from an immunized wild-type mouse, a human, or a transgenic mouse capable of making a human antibody as in WO 92/03918, WO 93/12227, and WO 94/25585), including hybridomas derived therefrom. Polynucleotide sequences selected in a first selection round (typically by affinity selection for displayed antibody binding to an antigen (e.g., a ligand) by any of these methods are pooled and the pool(s) is/are shuffled by in vitro and/or in vivo recombination, especially shuffling of CDRs (typically shuffling heavy chain CDRs with other heavy chain CDRs and light chain CDRs with other light chain CDRs) to produce a shuffled pool comprising a population of recombined selected polynucleotide sequences. The recombined selected polynucleotide sequences are expressed in a selection format as a displayed antibody and subjected to at least one subsequent selection round. The polynucleotide sequences selected in the subsequent selection round(s) can be used directly, sequenced, and/or subjected to one or more additional rounds of shuffling and subsequent selection until an antibody of the desired binding affinity is obtained. Selected sequences can also be back-crossed with polynucleotide sequences encoding neutral antibody framework sequences (i.e., having insubstantial functional effect on antigen binding), such as for example by back-crossing with a human variable region framework to produce human-like sequence antibodies. Generally, during back-crossing subsequent selection is applied to retain the property of binding to the predetermined antigen.

Alternatively, or in combination with the noted variations, the valency of the target epitope may be varied to control the average binding affinity of selected scfv library members. The target epitope can be bound to a surface or substrate at varying densities, such as by including a competitor epitope, by dilution, or by other method known to those in the art. A high density (valency) of predetermined epitope can be used to enrich for scfv library members who have relatively low affinity, whereas a low density (valency) can preferentially enrich for higher affinity scfv library members.

For generating diverse variable segments, a collection of synthetic oligonucleotides encoding random, pseudorandom, or a defined sequence kernal set of peptide sequences can be inserted by ligation into a predetermined site (e.g., a CDR). Similarly, the sequence diversity of one or more CDRs of the single-chain antibody cassette(s) can be expanded by mutating the CDR(s) with site-directed mutagenesis, CDR-replacement, and the like. The resultant DNA molecules can be propagated in a host for cloning and amplification prior to shuffling, or can be used directly (i.e., may avoid loss of diversity which may occur upon propagation in a host cell) and the selected library members subsequently shuffled.

Displayed peptide/polynucleotide complexes (library members), which encode a variable segment peptide sequence of interest or a single-chain antibody of interest are selected from the library by an affinity enrichment technique. This is accomplished by means of an immobilized macromolecule or epitope specific for the peptide sequence of interest, such as a receptor, other macromolecule, or other epitope species. Repeating the affinity selection procedure provides an enrichment of library members encoding the desired sequences, which may then be isolated for pooling and shuffling, for sequencing, and/or for further propagation and affinity enrichment.

The library members without the desired specificity are removed by washing. The degree and stringency of washing required will be determined for each peptide sequence or single-chain antibody of interest and the immobilized predetermined macromolecule or epitope. A certain degree of control can be exerted over the binding characteristics of the nascent peptide/DNA complexes recovered by adjusting the conditions of the binding incubation and the subsequent washing. The temperature, pH, ionic strength, divalent cations concentration, and the volume and duration of the washing will select for nascent peptide/DNA complexes within particular ranges of affinity for the immobilized macromolecule. Selection based on slow dissociation rate, which is usually predictive of high affinity, is often the most practical route. This may be done either by continued incubation in the presence of a saturating amount of free predetermined macromolecule, or by increasing the volume, number, and length of the washes. In each case, the rebinding of dissociated nascent peptide/DNA or peptide/RNA complex is prevented, and with increasing time, nascent peptide/DNA or peptide/RNA complexes of higher and higher affinity are recovered.

Additional modifications of the binding and washing procedures may be applied to find peptides with special characteristics. The affinities of some peptides are dependent on ionic strength or cation concentration. This is a useful characteristic for peptides that will be used in affinity purification of various proteins when gentle conditions for removing the protein from the peptides are required.

One variation involves the use of multiple binding targets (multiple epitope species, multiple receptor species), such that a scfv library can be simultaneously screened for a multiplicity of scfv which have different binding specificities. Given that the size of a scfv library often limits the diversity of potential scfv sequences, it is typically desirable to us scfv libraries of as large a size as possible. The time and economic considerations of generating a number of very large polysome scFv-display libraries can become prohibitive. To avoid this substantial problem, multiple predetermined epitope species (receptor species) can be concomitantly screened in a single library, or sequential screening against a number of epitope species can be used. In one variation, multiple target epitope species, each encoded on a separate bead (or subset of beads), can be mixed and incubated with a polysome-display scfv library under suitable binding conditions. The collection of beads, comprising multiple epitope species, can then be used to isolate, by affinity selection, scfv library members. Generally, subsequent affinity screening rounds can include the same mixture of beads, subsets thereof, or beads containing only one or two individual epitope species. This approach affords efficient screening, and is compatible with laboratory automation, batch processing, and high throughput screening methods.

A variety of techniques can be used in the present invention to diversify a peptide library or single-chain antibody library, or to diversify, prior to or concomitant with shuffling, around variable segment peptides found in early rounds of panning to have sufficient binding activity to the predetermined macromolecule or epitope. In one approach, the positive selected peptide/polynucleotide complexes (those identified in an early round of affinity enrichment) are sequenced to determine the identity of the active peptides. Oligonucleotides are then synthesized based on these active peptide sequences, employing a low level of all bases incorporated at each step to produce slight variations of the primary oligonucleotide sequences. This mixture of (slightly) degenerate oligonucleotides is then cloned into the variable segment sequences at the appropriate locations. This method produces systematic, controlled variations of the starting peptide sequences, which can then be shuffled. It requires, however, that individual positive nascent peptide/polynucleotide complexes be sequenced before mutagenesis, and thus is useful for expanding the diversity of small numbers of recovered complexes and selecting variants having higher binding affinity and/or higher binding specificity. In a variation, mutagenic PCR amplification of positive selected peptide/polynucleotide complexes (especially of the variable region sequences, the amplification products of which are shuffled in vitro and/or in vivo and one or more additional rounds of screening is done prior to sequencing. The same general approach can be employed with single-chain antibodies in order to expand the diversity and enhance the binding affinity/specificity, typically by diversifying CDRs or adjacent framework regions prior to or concomitant with shuffling. If desired, shuffling reactions can be spiked with mutagenic oligonucleotides capable of in vitro recombination with the selected library members can be included. Thus, mixtures of synthetic oligonucleotides and PCR produced polynucleotides (synthesized by error-prone or high-fidelity methods) can be added to the in vitro shuffling mix and be incorporated into resulting shuffled library members (shufflants).

The present invention of shuffling enables the generation of a vast library of CDR-variant single-chain antibodies. One way to generate such antibodies is to insert synthetic CDRs into the single-chain antibody and/or CDR randomization prior to or concomitant with shuffling. The sequences of the synthetic CDR cassettes are selected by referring to known sequence data of human CDR and are selected in the discretion of the practitioner according to the following guidelines: synthetic CDRs will have at least 40 percent positional sequence identity to known CDR sequences, and preferably will have at least 50 to 70 percent positional sequence identity to known CDR sequences. For example, a collection of synthetic CDR sequences can be generated by synthesizing a collection of oligonucleotide sequences on the basis of naturally-occurring human CDR sequences listed in Kabat (Kabat et al, 1991); the pool (s) of synthetic CDR sequences are calculated to encode CDR peptide sequences having at least 40 percent sequence identity to at least one known naturally-occurring human CDR sequence. Alternatively, a collection of naturally-occurring CDR sequences may be compared to generate consensus sequences so that amino acids used at a residue position frequently (i.e., in at least 5 percent of known CDR sequences) are incorporated into the synthetic CDRs at the corresponding position(s). Typically, several (e.g., 3 to about 50) known CDR sequences are compared and observed natural sequence variations between the known CDRs are tabulated, and a collection of oligonucleotides encoding CDR peptide sequences encompassing all or most permutations of the observed natural sequence variations is synthesized. For example but not for limitation, if a collection of human VH CDR sequences have carboxy-terminal amino acids which are either Tyr, Val, Phe, or Asp, then the pool(s) of synthetic CDR oligonucleotide sequences are designed to allow the carboxy-terminal CDR residue to be any of these amino acids. In some embodiments, residues other than those which naturally-occur at a residue position in the collection of CDR sequences are incorporated: conservative amino acid substitutions are frequently incorporated and up to 5 residue positions may be varied to incorporate non-conservative amino acid substitutions as compared to known naturally-occurring CDR sequences. Such CDR sequences can be used in primary library members (prior to first round screening) and/or can be used to spike in vitro shuffling reactions of selected library member sequences. Construction of such pools of defined and/or degenerate sequences will be readily accomplished by those of ordinary skill in the art.

The collection of synthetic CDR sequences comprises at least one member that is not known to be a naturally-occurring CDR sequence. It is within the discretion of the practitioner to include or not include a portion of random or pseudorandom sequence corresponding to N region addition in the heavy chain CDR; the N region sequence ranges from 1 nucleotide to about 4 nucleotides occurring at V-D and D-J junctions. A collection of synthetic heavy chain CDR sequences comprises at least about 100 unique CDR sequences, typically at least about 1,000 unique CDR sequences, preferably at least about 10,000 unique CDR sequences, frequently more than 50,000 unique CDR sequences; however, usually not more than about $1\times10^6$ unique CDR sequences are included in the collection, although occasionally $1\times10^7$ to $1\times10^8$ unique CDR sequences are present, especially if conservative amino acid substitutions are permitted at positions where the conservative amino acid substituent is not present or is rare (i.e., less than 0.1 percent) in that position in naturally-occurring human CDRS. In general, the number of unique CDR sequences included in a library should not exceed the expected number of primary transformants in the library by more than a factor of 10. Such single-chain antibodies generally bind of about at least $1\times10^6$ $M^{-1}$, preferably with an affinity of about at least $5\times10^7$ $M^{-1}$, more preferably with an affinity of at least $1\times10^8$ $M^{-1}$ to $1\times10^9$ $M^{-1}$ or more, sometimes up to $1\times10^{10}$ $M^{-1}$ or more. Frequently, the predetermined antigen is a human protein, such as for example a human cell surface antigen (e.g., CD4, CD8, IL-2 receptor, EGF receptor, PDGF receptor), other human biological macromolecule (e.g., thrombomodulin, protein C, carbohydrate antigen, sialyl Lewis antigen, Lse-lectin), or nonhuman disease associated macromolecule (e.g., bacterial LPS, virion capsid protein or envelope glycoprotein) and the like.

High affinity single-chain antibodies of the desired specificity can be engineered and expressed in a variety of systems. Furthermore, the single-chain antibodies can be used as a basis for constructing whole antibodies or various fragments thereof (Kettleborough et al, 1994). The variable region encoding sequence may be isolated (e.g., by PCR amplification or subcloning) and spliced to a sequence encoding a desired human constant region to encode a human sequence antibody more suitable for human therapeutic uses where immunogenicity is preferably minimized. The polynucleotide(s) having the resultant fully human encoding sequence(s) can be expressed in a host cell (e.g., from an expression vector in a mammalian cell) and purified for pharmaceutical formulation.

The DNA expression constructs will typically include an expression control DNA sequence operably linked to the coding sequences, including naturally-associated or heterologous promoter regions. Preferably, the expression control sequences will be eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the mutant "engineered" antibodies.

As stated previously, the DNA sequences will be expressed in hosts after the sequences have been operably linked to an expression control sequence (i.e., positioned to ensure the transcription and translation of the structural gene). These expression vectors are typically replicable in the host organisms either as episomes or as an integral part of the host chromosomal DNA. Commonly, expression vectors will contain selection markers, e.g., tetracycline or neomycin, to permit detection of those cells transformed with the desired DNA sequences (see, e.g., U.S. Pat. No. 4,704,362, which is incorporated herein by reference).

In addition to eukaryotic microorganisms such as yeast, mammalian tissue cell culture may also be used to produce the polypeptides of the present invention (see Winnacker, 1987), which is incorporated herein by reference). Eukaryotic cells are actually preferred, because a number of suitable host cell lines capable of secreting intact immunoglobulins have been developed in the art, and include the CHO cell lines, various COS cell lines, HeLa cells, and myeloma cell lines, but preferably transformed Bcells or hybridomas. Expression vectors for these cells can include expression control sequences, such as an origin of replication, a promoter, an enhancer (Queen et al, 1986), and necessary processing information sites, such as ribosome binding sites, RNA splice sites, polyadenylation sites, and transcriptional terminator sequences. Preferred expression control sequences are promoters derived from immunoglobulin genes, cytomegalovirus, SV40, Adenovirus, Bovine Papilloma Virus, and the like.

Inserting an enhancer sequence into the vector can increase eukaryotic DNA transcription. Enhancers are cis-acting sequences of between 10 to 300 bp that increase transcription by a promoter. Enhancers can effectively increase transcription when either 51 or 31 to the transcription unit. They are also effective if located within an intron or within the coding sequence itself. Typically, viral enhancers are used, including SV40 enhancers, cytomegalovirus enhancers, polyoma enhancers, and adenovirus enhancers. Enhancer sequences from mammalian systems are also commonly used, such as the mouse immunoglobulin heavy chain enhancer.

Mammalian expression vector systems will also typically include a selectable marker gene. Examples of suitable markers include, the dihydrofolate reductase gene (DHFR), the thymidine kinase gene (TK), or prokaryotic genes conferring drug resistance. The first two marker genes prefer the use of mutant cell lines that lack the ability to grow without the addition of thymidine to the growth medium. Transformed cells can then be identified by their ability to grow on non-supplemented media. Examples of prokaryotic drug resistance genes useful as markers include genes conferring resistance to G418, mycophenolic acid and hygromycin.

The vectors containing the DNA segments of interest can be transferred into the host cell by well-known methods, depending on the type of cellular host. For example, calcium chloride transfection is commonly utilized for prokaryotic cells, whereas calcium phosphate treatment. lipofection, or electroporation may be used for other cellular hosts. Other methods used to transform mammalian cells include the use of Polybrene, protoplast fusion, liposomes, electroporation, and microinjection (see, generally, Sambrook et al, 1982 and 1989).

Once expressed, the antibodies, individual mutated immunoglobulin chains, mutated antibody fragments, and other immunoglobulin polypeptides of the invention can be purified according to standard procedures of the art, including ammonium sulfate precipitation, fraction column chromatography, gel electrophoresis and the like (see, generally, Scopes, 1982). Once purified, partially or to homogeneity as desired, the polypeptides may then be used therapeutically or in developing and performing assay procedures, immunofluorescent stainings, and the like (see, generally, Lefkovits and Pernis, 1979 and 1981; Lefkovits, 1997).

The antibodies generated by the method of the present invention can be used for diagnosis and therapy. By way of illustration and not limitation, they can be used to treat cancer, autoimmune diseases, or viral infections. For treatment of cancer, the antibodies will typically bind to an antigen expressed preferentially on cancer cells, such as erbB-2, CEA, CD33, and many other antigens and binding members well known to those skilled in the art.

End-Selection

This invention provides a method for selecting a subset of polynucleotides from a starting set of polynucleotides, which method is based on the ability to discriminate one or more selectable features (or selection markers) present anywhere in a working polynucleotide, so as to allow one to perform selection for (positive selection) &/or against (negative selection) each selectable polynucleotide. In a preferred aspect, a method is provided termed end-selection, which method is based on the use of a selection marker located in part or entirely in a terminal region of a selectable polynucleotide, and such a selection marker may be termed an "end-selection marker".

End-selection may be based on detection of naturally occurring sequences or on detection of sequences introduced experimentally (including by any mutagenesis procedure mentioned herein and not mentioned herein) or on both, even within the same polynucleotide. An end-selection marker can be a structural selection marker or a functional selection marker or both a structural and a functional selection marker. An end-selection marker may be comprised of a polynucleotide sequence or of a polypeptide sequence or of any chemical structure or of any biological or biochemical tag, including markers that can be selected using methods based on the detection of radioactivity, of enzymatic activity, of fluorescence, of any optical feature, of a magnetic property (e.g. using magnetic beads), of immunoreactivity, and of hybridization.

End-selection may be applied in combination with any method serviceable for performing mutagenesis. Such mutagenesis methods include, but are not limited to, methods described herein (supra and infra). Such methods include, by way of non-limiting exemplification, any method that may be referred herein or by others in the art by any of the following terms: "saturation mutagenesis", "shuffling", "recombination", "re-assembly", "error-prone PCR", "assembly PCR", "sexual PCR", "crossover PCR", "oligonucleotide primer-directed mutagenesis", "recursive (&/or exponential) ensemble mutagenesis (see Arkin and Youvan, 1992)", "cassette mutagenesis", "in vivo mutagenesis", and "in vitro mutagenesis". Moreover, end-selection may be performed on molecules produced by any mutagenesis &/or amplification method (see, e.g., Arnold, 1993; Caldwell and Joyce, 1992; Stemmer, 1994; following which method it is desirable to select for (including to screen for the presence of) desirable progeny molecules.

In addition, end-selection may be applied to a polynucleotide apart from any mutagenesis method. In a preferred embodiment, end-selection, as provided herein, can be used in order to facilitate a cloning step, such as a step of ligation to another polynucleotide (including ligation to a vector). This invention thus provides for end-selection as a serviceable means to facilitate library construction, selection &/or enrichment for desirable polynucleotides, and cloning in general.

In a particularly preferred embodiment, end-selection can be based on (positive) selection for a polynucleotide; alternatively end-selection can be based on (negative) selection against a polynucleotide; and alternatively still, end-selection can be based on both (positive) selection for, and on (negative) selection against, a polynucleotide. End-selection, along with other methods of selection &/or screening, can be performed in an iterative fashion, with any combination of like or unlike selection &/or screening methods and serviceable mutagenesis methods, all of which can be performed in an iterative fashion and in any order, combination, and permutation.

It is also appreciated that, according to one embodiment of this invention, end-selection may also be used to select a polynucleotide is at least in part: circular (e.g. a plasmid or any other circular vector or any other polynucleotide that is partly circular), &/or branched, &/or modified or substituted with any chemical group or moiety. In accord with this embodiment, a polynucleotide may be a circular molecule comprised of an intermediate or central region, which region is flanked on a 5' side by a 5' flanking region (which, for the purpose of end-selection, serves in like manner to a 5' terminal region of a non-circular polynucleotide) and on a 3' side by a 3' terminal region (which, for the purpose of end-selection, serves in like manner to a 3' terminal region of a non-circular polynucleotide). As used in this non-limiting exemplification, there may be sequence overlap between any two regions or even among all three regions.

In one non-limiting aspect of this invention, end-selection of a linear polynucleotide is performed using a general approach based on the presence of at least one end-selection marker located at or near a polynucleotide end or terminus (that can be either a 5' end or a 3' end). In one particular non-limiting exemplification, end-selection is based on selection for a specific sequence at or near a terminus such as, but not limited to, a sequence recognized by an enzyme that recognizes a polynucleotide sequence. An enzyme that recognizes and catalyzes a chemical modification of a polynucleotide is referred to herein as a polynucleotide-acting enzyme. In a preferred embodiment, serviceable polynucleotide-acting enzymes are exemplified non-exclusively by enzymes with polynucleotide-cleaving activity, enzymes with polynucleotide-methylating activity, enzymes with polynucleotide-ligating activity, and enzymes with a plurality of distinguishable enzymatic activities (including non-exclusively, e.g., both polynucleotide-cleaving activity and polynucleotide-ligating activity).

Relevant polynucleotide-acting enzymes thus also include any commercially available or non-commercially available polynucleotide endonucleases and their companion methylases including those mentioned in the following cited reference (Roberts and Macelis, 1996). Preferred polynucleotide endonucleases include—but are not limited to—type II restriction enzymes (including type IIS), and include enzymes that cleave both strands of a double stranded polynucleotide (e.g. Not I, which cleaves both strands at 5' . . . GC/GGCCGC . . .3') and enzymes that cleave only one strand of a double stranded polynucleotide, i.e. enzymes that have polynucleotide-nicking activity, (e.g. N. BstNB I, which cleaves only one strand at 5' . . . GAGTCNNNN/N . . . 3'). Relevant polynucleotide-acting enzymes also include type III restriction enzymes. It is appreciated that relevant polynucleotide-acting enzymes also include any enzymes that may be developed in the future, though currently unavailable, that are serviceable for generating a ligation compatible end, preferably a sticky end, in a polynucleotide.

In one preferred exemplification, a serviceable selection marker is a restriction site in a polynucleotide that allows a corresponding type II (or type IIS) restriction enzyme to cleave an end of the polynucleotide so as to provide a ligatable end (including a blunt end or alternatively a sticky end with at least a one base overhang) that is serviceable for a desirable ligation reaction without cleaving the polynucleotide internally in a manner that destroys a desired internal sequence in the polynucleotide. Thus it is provided that, among relevant restriction sites, those sites that do not occur internally (i.e. that do not occur apart from the termini) in a specific working polynucleotide are preferred when the use of a corresponding restriction enzyme(s) is not intended to cut the working polynucleotide internally. This allows one to perform restriction digestion reactions to completion or to near completion without incurring unwanted internal cleavage in a working polynucleotide.

According to a preferred aspect, it is thus preferable to use restriction sites that are not contained, or alternatively that are not expected to be contained, or alternatively that unlikely to be contained (e.g. when sequence information regarding a working polynucleotide is incomplete) internally in a polynucleotide to be subjected to end-selection. In accordance with this aspect, it is appreciated that restriction sites that occur relatively infrequently are usually preferred over those that occur more frequently. On the other hand it is also appreciated that there are occasions where internal cleavage of a polypeptide is desired, e.g. to achieve recombination or other mutagenic procedures along with end-selection.

In accord with this invention, it is also appreciated that methods (e.g. mutagenesis methods) can be used to remove unwanted internal restriction sites. It is also appreciated that a partial digestion reaction (i.e. a digestion reaction that proceeds to partial completion) can be used to achieve digestion at a recognition site in a terminal region while sparing a susceptible restriction site that occurs internally in a polynucleotide and that is recognized by the same enzyme. In one aspect, partial digest are useful because it is appreciated that certain enzymes show preferential cleavage of the same recognition sequence depending on the location and environment in which the recognition sequence occurs. For example, it is appreciated that, while lambda DNA has 5 EcoR I sites, cleavage of the site nearest to the right terminus has been reported to occur 10 times faster than the sites in the middle of the molecule. Also, for example, it has been reported that, while Sac II has four sites on lambda DNA, the three clustered centrally in lambda are cleaved 50 times faster than the remaining site near the terminus (at nucleotide 40,386). Summarily, site preferences have been reported for various enzymes by many investigators (e.g., Thomas and Davis, 1975; Forsblum et al, 1976; Nath and Azzolina, 1981; Brown and Smith, 1977; Gingeras and Brooks, 1983; Krüger et al, 1988; Conrad and Topal, 1989; Oiler et al, 1991; Topal, 1991; and Pein, 1991; to name but a few). It is appreciated that any empirical observations as well as any mechanistic understandings of site preferences by any serviceable polynucleotide-acting enzymes, whether currently available or to be procured in the future, may be serviceable in end-selection according to this invention.

It is also appreciated that protection methods can be used to selectively protect specified restriction sites (e.g. internal sites) against unwanted digestion by enzymes that would otherwise cut a working polypeptide in response to the presence of those sites; and that such protection methods include modifications such as methylations and base substitutions (e.g. U instead of T) that inhibit an unwanted enzyme activity. It is appreciated that there are limited numbers of available restriction enzymes that are rare enough (e.g. having very long recognition sequences) to create large (e.g. megabase-long) restriction fragments, and that protection approaches (e.g. by methylation) are serviceable for increasing the rarity of enzyme cleavage sites. The use of M.Fnu II (mCGCG) to increase the apparent rarity of Not I approximately twofold is but one example among many (Qiang et al, 1990; Nelson et al, 1984; Maxam and Gilbert, 1980; Raleigh and Wilson, 1986).

According to a preferred aspect of this invention, it is provided that, in general, the use of rare restriction sites is preferred. It is appreciated that, in general, the frequency of occurrence of a restriction site is determined by the number of nucleotides contained therein, as well as by the ambiguity of the base requirements contained therein. Thus, in a non-limiting exemplification, it is appreciated that, in general, a restriction site composed of, for example, 8 specific nucleotides (e.g. the Not I site or GC/GGCCGC, with an estimated relative occurrence of 1 in $4^8$, i.e. 1 in 65,536, random 8-mers) is relatively more infrequent than one composed of, for example, 6 nucleotides (e.g. the Sma I site or CCC/GGG, having an estimated relative occurrence of 1 in $4^6$, i.e. 1 in 4,096, random 6-mers), which in turn is relatively more infrequent than one composed of, for example, 4 nucleotides (e.g. the Msp I site or C/CGG, having an estimated relative occurrence of 1 in $4^4$, i.e. 1 in 256, random 4-mers). Moreover, in another non-limiting exemplification, it is appreciated that, in general, a restriction site having no ambiguous (but only specific) base requirements (e.g. the Fin I site or GTCCC, having an estimated relative occurrence of 1 in $4^5$, i.e. 1 in 1024, random 5-mers) is relatively more infrequent than one having an ambiguous W (where W=A or T) base requirement (e.g. the Ava II site or G/GWCC, having an estimated relative occurrence of 1 in 4×4×2×4×4—i.e. 1 in 512—random 5-mers), which in turn is relatively more infrequent than one having an ambiguous N (where N=A or C or G or T) base requirement (e.g. the Asu I site or G/GNCC, having an estimated relative occurrence of 1 in 4×4×1×4×4, i.e. 1 in 256—random 5-mers). These relative occurrences are considered general estimates for actual polynucleotides, because it is appreciated that specific nucleotide bases (not to mention specific nucleotide sequences) occur with dissimilar frequencies in specific polynucleotides, in specific species of organisms, and in specific groupings of organisms. For example, it is appreciated that the % G+C contents of different species of organisms are often very different and wide ranging.

The use of relatively more infrequent restriction sites as a selection marker include—in a non-limiting fashion—preferably those sites composed at least a 4 nucleotide sequence, more preferably those composed at least a 5 nucleotide sequence, more preferably still those composed at least a 6 nucleotide sequence (e.g. the BamH I site or G/GATCC, the Bgl II site or A/GATCT, the Pst I site or CTGCA/G, and the Xba I site or T/CTAGA), more preferably still those composed at least a 7 nucleotide sequence, more preferably still those composed of an 8 nucleotide sequence nucleotide sequence (e.g. the Asc I site or GG/CGCGCC, the Not I site or GC/GGCCGC, the Pac I site or TTAAT/TAA, the Pme I site or GTTT/AAAC, the Srf I site or GCCC/GGGC, the Sse838 I site or CCTGCA/GG, and the Swa I site or ATTT/AAAT), more preferably still those composed of a 9 nucleotide sequence, and even more preferably still those composed of at least a 10 nucleotide sequence (e.g. the BspG I site or CG/CGCTGGAC). It is further appreciated that some restriction sites (e.g. for class IIS enzymes) are comprised of a portion of relatively high specificity (i.e. a portion containing a principal determinant of the frequency of occurrence of the restriction site) and a portion of relatively low specificity; and that a site of cleavage may or may not be contained within a portion of relatively low specificity. For example, in the Eco57 I site or CTGAAG(16/14), there is a portion of relatively high specificity (i.e. the CTGAAG portion) and a portion of relatively low specificity (i.e. the N16 sequence) that contains a site of cleavage.

In another preferred embodiment of this invention, a serviceable end-selection marker is a terminal sequence that is recognized by a polynucleotide-acting enzyme that recognizes a specific polynucleotide sequence. In a preferred aspect of this invention, serviceable polynucleotide-acting enzymes also include other enzymes in addition to classic type II restriction enzymes. According to this preferred aspect of this invention, serviceable polynucleotide-acting enzymes also include gyrases, helicases, recombinases, relaxases, and any enzymes related thereto.

Among preferred examples are topoisomerases (which have been categorized by some as a subset of the gyrases) and any other enzymes that have polynucleotide-cleaving activity (including preferably polynucleotide-nicking activity) &/or polynucleotide-ligating activity. Among preferred topoisomerase enzymes are topoisomerase I enzymes, which is available from many commercial sources (Epicentre Technologies, Madison, Wis.; Invitrogen, Carlsbad, Calif.; Life Technologies, Gathesburg, Md.) and conceivably even more private sources. It is appreciated that similar enzymes may be developed in the future that are serviceable for end-selection as provided herein. A particularly preferred topoisomerase I enzyme is a topoisomerase I enzyme of vaccinia virus origin, that has a specific recognition sequence (e.g. 5' . . . AAGGG . . . 3') and has both polynucleotide-nicking activity and polynucleotide-ligating activity. Due to the specific nicking-activity of this enzyme (cleavage of one strand), internal recognition sites are not prone to polynucleotide destruction resulting from the nicking activity (but rather remain annealed) at a temperature that causes denaturation of a terminal site that has been nicked. Thus for use in end-selection, it is preferable that a nicking site for topoisomerase-based end-selection be no more than 100 nucleotides from a terminus, more preferably no more than 50 nucleotides from a terminus, more preferably still no more than 25 nucleotides from a terminus, even more preferably still no more than 20 nucleotides from a terminus, even more preferably still no more than 15 nucleotides from a terminus, even more preferably still no more than 10 nucleotides from a terminus, even more preferably still no more than 8 nucleotides from a terminus, even more preferably still no more than 6 nucleotides from a terminus, and even more preferably still no more than 4 nucleotides from a terminus.

In a particularly preferred exemplification that is non-limiting yet clearly illustrative, it is appreciated that when a nicking site for topoisomerase-based end-selection is 4 nucleotides from a terminus, nicking produces a single stranded oligo of 4 bases (in a terminal region) that can be denatured from its complementary strand in an end-selectable polynucleotide; this provides a sticky end (comprised of 4 bases) in a polynucleotide that is serviceable for an ensuing ligation reaction. To accomplish ligation to a cloning vector (preferably an expression vector), compatible sticky ends can be generated in a cloning vector by any means including by restriction enzyme-based means. The terminal nucleotides (comprised of 4 terminal bases in this specific example) in an end-selectable polynucleotide terminus are thus wisely chosen to provide compatibility with a sticky end generated in a cloning vector to which the polynucleotide is to be ligated.

On the other hand, internal nicking of an end-selectable polynucleotide, e.g. 500 bases from a terminus, produces a single stranded oligo of 500 bases that is not easily denatured from its complementary strand, but rather is serviceable for repair (e.g. by the same topoisomerase enzyme that produced the nick).

This invention thus provides a method—e.g. that is vaccinia topoisomerase-based &/or type II (or IIS) restriction endonuclease-based &/or type III restriction endonuclease-based &/or nicking enzyme-based (e.g. using N. BstNB I)—for producing a sticky end in a working polynucleotide, which end is ligation compatible, and which end can be comprised of at least a 1 base overhang. Preferably such a sticky end is comprised of at least a 2-base overhang, more preferably such a sticky end is comprised of at least a 3-base overhang, more preferably still such a sticky end is comprised of at least a 4-base overhang, even more preferably still such a sticky end is comprised of at least a 5-base overhang, even more preferably still such a sticky end is comprised of at least a 6-base overhang. Such a sticky end may also be comprised of at least a 7-base overhang, or at least an 8-base overhang, or at least a 9-base overhang, or at least a 10-base overhang, or at least 15-base overhang, or at least a 20-base overhang, or at least a 25-base overhang, or at least a 30-base overhang. These overhangs can be comprised of any bases, including A, C, G, or T.

It is appreciated that sticky end overhangs introduced using topoisomerase or a nicking enzyme (e.g. using N. BstNB I) can be designed to be unique in a ligation environment, so as to prevent unwanted fragment reassemblies, such as self-dimerizations and other unwanted concatamerizations.

According to one aspect of this invention, a plurality of sequences (which may but do not necessarily overlap) can be introduced into a terminal region of an end-selectable polynucleotide by the use of an oligo in a polymerase-based reaction. In a relevant, but by no means limiting example, such an oligo can be used to provide a preferred 5' terminal region that is serviceable for topoisomerase I-based end-selection, which oligo is comprised of: a 1-10 base sequence that is convertible into a sticky end (preferably by a vaccinia topoisomerase I), a ribosome binding site (i.e. and "RBS", that is preferably serviceable for expression cloning), and optional linker sequence followed by an ATG start site and a template-specific sequence of 0-100 bases (to facilitate annealment to the template in the a polymerase-based reaction). Thus, according to this example, a serviceable oligo (which may be termed a forward primer) can have the sequence: 5'[terminal sequence=$(N)_{1-10}$][topoisomerase I site & RBS=AAGGGAGGAG][linker=$(N)_{1-100}$][start codon and template-specific sequence=ATG$(N)_{0-100}$]3'.

Analogously, in a relevant, but by no means limiting example, an oligo can be used to provide a preferred 3' terminal region that is serviceable for topoisomerase I-based end-selection, which oligo is comprised of: a 1-10 base sequence that is convertible into a sticky end (preferably by a vaccinia topoisomerase I), and optional linker sequence followed by a template-specific sequence of 0-100 bases (to facilitate annealment to the template in the a polymerase-based reaction). Thus, according to this example, a serviceable oligo (which may be termed a reverse primer) can have the sequence: 5'[terminal sequence=$(N)_{1-10}$][topoisomerase I site=AAGGG][linker=$(N)_{1-100}$][template-specific sequence=$(N)_{0-100}$]3'.

It is appreciated that, end-selection can be used to distinguish and separate parental template molecules (e.g. to be subjected to mutagenesis) from progeny molecules (e.g. generated by mutagenesis). For example, a first set of primers, lacking in a topoisomerase I recognition site, can be used to modify the terminal regions of the parental molecules (e.g. in polymerase-based amplification). A different second set of primers (e.g. having a topoisomerase I recognition site) can then be used to generate mutated progeny molecules (e.g. using any polynucleotide chimerization method, such as interrupted synthesis, template-switching polymerase-based amplification, or interrupted synthesis; or using saturation mutagenesis; or using any other method for introducing a topoisomerase I recognition site into a mutagenized progeny molecule as disclosed herein) from the amplified template molecules. The use of topoisomerase I-based end-selection can then facilitate, not only discernment, but selective topoisomerase I-based ligation of the desired progeny molecules.

Annealment of a second set of primers to thusly amplified parental molecules can be facilitated by including sequences in a first set of primers (i.e. primers used for amplifying a set parental molecules) that are similar to a topoisomerase I recognition site, yet different enough to prevent functional topoisomerase I enzyme recognition. For example, sequences that diverge from the AAGGG site by anywhere from 1 base to all 5 bases can be incorporated into a first set of primers (to be used for amplifying the parental templates prior to subjection to mutagenesis). In a specific, but non-limiting aspect, it is thus provided that a parental molecule can be amplified using the following exemplary—but by no means limiting— set of forward and reverse primers:

```
Forward Primer:
5'  CTAGAAGAGAGGAGAAAACCATG(N)₁₀₋₁₀₀ 3', and

Reverse Primer:
5'  GATCAAAGGCGCGCCTGCAGG(N)₁₀₋₁₀₀ 3'
```

According to this specific example of a first set of primers, $(N)_{10-100}$ represents preferably a 10 to 100 nucleotide-long template-specific sequence, more preferably a 10 to 50 nucleotide-long template-specific sequence, more preferably still a 10 to 30 nucleotide-long template-specific sequence, and even more preferably still a 15 to 25 nucleotide-long template-specific sequence.

According to a specific, but non-limiting aspect, it is thus provided that, after this amplification (using a disclosed first set of primers lacking in a true topoisomerase I recognition site), amplified parental molecules can then be subjected to mutagenesis using one or more sets of forward and reverse primers that do have a true topoisomerase I recognition site. In a specific, but non-limiting aspect, it is thus provided that a parental molecule can be used as templates for the generation of a mutagenized progeny molecule using the following exemplary—but by no means limiting—second set of forward and reverse primers:

```
Forward Primer:     5'  CTAGAAGGGAGGAGAAAACCATG 3'

Reverse Primer:     5'  GATCAAAGGCGCGCCTGCAGG 3'
(contains Asc I recognition sequence)
```

It is appreciated that any number of different primers sets not specifically mentioned can be used as first, second, or subsequent sets of primers for end-selection consistent with this invention. Notice that type II restriction enzyme sites can be incorporated (e.g. an Asc I site in the above example). It is provided that, in addition to the other sequences mentioned, the experimentalist can incorporate one or more N,N,G/T triplets into a serviceable primer in order to subject a working polynucleotide to saturation mutagenesis. Summarily, use of a second and/or subsequent set of primers can achieve dual goals of introducing a topoisomerase I site and of generating mutations in a progeny polynucleotide.

Thus, according to one use provided, a serviceable end-selection marker is an enzyme recognition site that allows an enzyme to cleave (including nick) a polynucleotide at a specified site, to produce a ligation-compatible end upon denaturation of a generated single stranded oligo. Ligation of the produced polynucleotide end can then be accomplished by the same enzyme (e.g. in the case of vaccinia virus topoisomerase I), or alternatively with the use of a different enzyme. According to one aspect of this invention, any serviceable end-selection markers, whether like (e.g. two vaccinia virus topoisomerase I recognition sites) or unlike (e.g. a class II restriction enzyme recognition site and a vaccinia virus topoisomerase I recognition site) can be used in combination to select a polynucleotide. Each selectable polynucleotide can thus have one or more end-selection markers, and they can be like or unlike end-selection markers. In a particular aspect, a plurality of end-selection markers can be located on one end of a polynucleotide and can have overlapping sequences with each other.

It is important to emphasize that any number of enzymes, whether currently in existence or to be developed, can be serviceable in end-selection according to this invention. For example, in a particular aspect of this invention, a nicking enzyme (e.g. N. BstNB I, which cleaves only one strand at 5' . . . GAGTCNNNN/N . . . 3') can be used in conjunction with a source of polynucleotide-ligating activity in order to achieve end-selection. According to this embodiment, a recognition site for N. BstNB I—instead of a recognition site for topoisomerase I—should be incorporated into an end-selectable polynucleotide (whether end-selection is used for selection of a mutagenized progeny molecule or whether end-selection is used apart from any mutagenesis procedure).

It is appreciated that the instantly disclosed end-selection approach using topoisomerase-based nicking and ligation has several advantages over previously available selection methods. In sum, this approach allows one to achieve direction cloning (including expression cloning). Specifically, this approach can be used for the achievement of: direct ligation (i.e. without subjection to a classic restriction-purification-ligation reaction, that is susceptible to a multitude of potential problems from an initial restriction reaction to a ligation reaction dependent on the use of T4 DNA ligase); separation of progeny molecules from original template molecules (e.g. original template molecules lack topoisomerase I sites that not introduced until after mutagenesis), obviation of the need for size separation steps (e.g. by gel chromatography or by other electrophoretic means or by the use of size-exclusion membranes), preservation of internal sequences (even when topoisomerase I sites are present), obviation of concerns about unsuccessful ligation reactions (e.g. dependent on the use of T4 DNA ligase, particularly in the presence of unwanted residual restriction enzyme activity), and facilitated expression cloning (including obviation of frame shift concerns). Concerns about unwanted restriction enzyme-based cleavages—especially at internal restriction sites (or even at often unpredictable sites of unwanted star activity) in a working polynucleotide—that are potential sites of destruction of a working polynucleotide can also be obviated by the instantly disclosed end-selection approach using topoisomerase-based nicking and ligation.

In addition to modifying the monomeric polypeptide by modifying the nucleic acid encoding the polypeptide, the monomeric polypeptide of the present invention may be modified using one or methods described below.

Modifications to Improve Protease Resistance of the Monomeric Polypeptide

One of the objectives of improving the protease resistance of the monomeric polypeptide is to increase the time available for drug targeting and drug release at the target site when the polymer containing the monomeric polypeptide is used in a nanoscale drug delivery vehicle or a drug capsule. Improvements in protease resistance may be achieved by several methods. These methods include conventional mutagenesis to remove susceptible cleavage sites, the modification by glycosylation to protect the amino acid backbone of the monomeric polypeptide, and the introduction of poly(ethylene glycol), PEG, to produce a PEGylated monomeric polypeptide that is shielded from proteolysis. The attachment of PEG to the monomeric polypeptide may be achieved through the introduction of surface exposed cysteines that may be used for specific PEG coupling. The modification of the glycosylation pattern and the degree of PEGylation may also depend on other considerations because both modifications have additional benefits as discussed below.

Modifications to Reduce the Immunogenicity of the Monomeric Polypeptide

One goal of these modifications is to reduce or mask antigenic determinants on the monomeric polypeptide to minimize potential allergic responses. The method of modifying the monomeric polypeptide involves: analyzing potential antigenic domains, and identifying cysteine insertion sites for possible use in PEGylation masking strategies (see Kozlowski, Harris, *Improvements in protein PEGylation: PEGylated interferons for treatment of hepatitis C* J. Controlled Release: v. 72, pp.217-224 (2001)). The method may also involves: computer modeling to identify potential amino acid domains on the monomeric polypeptide surface that are likely to be antigenic followed by modifying these sites through the mutagenesis method described in the present invention. In addition, glycosylation patterns of the monomeric polypeptide may be modified to produce a molecule that is less likely to be recognized as foreign.

Modifications to Attach Targeting Vectors on the Monomeric Polypeptide

In order to better direct the nanoscale drug delivery vehicle or polymer of the present invention to a particular desired location in an animal body, a targeting vector may be attached to the polymer or the monomeric polypeptide of the present invention. The targeting vector useful in the present invention includes antibodies, oligosaccharides, and Morphatides™. All of these targeting vectors may be readily attached to the monomeric polypeptide surface using conventional chemistries. Antibodies are the most common targeting vectors but oligosaccharides have also been shown to function as effective targeting moieties (see Wu, *Evidence for targeted gene delivery to HepG2 hepatoma cells in vitro*, V: 27, no. 3, pp. 887-892 (1988); Hashida, Akamatsu, Nishikawa, Fumiyoshi, Takakura, *Design of polymeric prodrugs of prostaglandin $E_1$ having galactose residue for hepatocyte targeting*, J. Controlled Release: v. 62, pp. 253-262 (1999)). The presence of a plurality of potential N-linked glycosylation sites in the monomeric polypeptide makes glycosylation-based targeting an attractive approach. In addition, Morphatides™ may be attached to the monomeric polypeptide using common synthetic methods. Morphatides™ is a derivatized nucleotide complex that may be optimized through iterative in vitro evolution to bind specific antigens.

Morphatides™ are evolvable, synthetic molecules that consist of a polynucleotide scaffold in association with reversible modifiers that contribute to molecular selectivity and binding. Morphatides™ possesses both the selective evolvability of aptamers (see Osborne, Ellington, *Nucleic Acid Selection and the Challenge of Combinatorial Chemistry*. Chemical reviews, v. 97, pp. 349-370 (1997)) and the considerable binding properties of proteins such as demonstrated by antibodies. Morphatides™ are evolvable by repeated cycles of selection against a target molecule. The evolvability of Morphatides™ is made possible in part because the molecular modifications of the polynucleotide scaffold are reversible. This reversibility is an element of their design, because between rounds of affinity selection against a chosen target, the polynucleotide scaffold is subjected to amplification by PCR. An additional feature of the amplified scaffolds in Morphatides™ is their "memory" of which sites were modified so that they may be re-modified for the next round of selection/maturation. Repeated cycles of modification, selection against a chosen target, de-modification and PCR amplification of the selected molecules can thus lead to the enrichment of molecules effectively bred to tightly bind selected targets. Once a Morphatide™ has been successfully evolved against a chosen target, a final Morphatide™ with the desired properties may be produced without the need for reversible chemistry. The final Morphatide™ product is a stable, synthetic, cost-effective molecule with the properties of a synthetic antibody.

In another aspect, the isolated nucleic acids of the Group A nucleic acid sequences, sequences substantially identical thereto, complementary sequences, or a fragment comprising at least 10, 15, 20, 25, 30, 35, 40, 50, 75, 100, 150, 200, 300, 400, or 500 consecutive bases of one of the foregoing sequences may also be used as probes to determine whether a biological sample, such as a soil sample, contains an organism having a nucleic acid sequence of the invention or an organism from which the nucleic acid was obtained. Preferably, the isolated nucleic acids of SEQ ID NOS. 7 and 9, sequences substantially identical thereto, complementary sequences, or a fragment comprising at least 10, 15, 20, 25, 30, 35, 40, 50, 75, 100, 150, 200, 300, 400, or 500 consecutive bases of one of the foregoing sequences may also be used as probes. In such procedures, a biological sample potentially harboring the organism from which the nucleic acid was isolated is obtained and nucleic acids are obtained from the sample. The nucleic acids are contacted with the probe under conditions which permit the probe to specifically hybridize to any complementary sequences which are present therein.

Where necessary, conditions which permit the probe to specifically hybridize to complementary sequences may be determined by placing the probe in contact with complementary sequences from samples known to contain the complementary sequence as well as control sequences which do not contain the complementary sequence. Hybridization conditions, such as the salt concentration of the hybridization buffer, the formamide concentration of the hybridization buffer, or the hybridization temperature, may be varied to identify conditions which allow the probe to hybridize specifically to complementary nucleic acids.

If the sample contains the organism from which the nucleic acid was isolated, specific hybridization of the probe is then detected. Hybridization may be detected by labeling the probe with a detectable agent such as a radioactive isotope, a fluorescent dye or an enzyme capable of catalyzing the formation of a detectable product.

Many methods for using the labeled probes to detect the presence of complementary nucleic acids in a sample are familiar to those skilled in the art. These include Southern Blots, Northern Blots, colony hybridization procedures, and dot blots. Protocols for each of these procedures are provided in Ausubel et al. Current Protocols in Molecular Biology, John Wiley & Sons, Inc. (1997) and Sambrook et al., Molecular Cloning: A Laboratory Manual 2d Ed., Cold Spring Harbor Laboratory Press, (1989), the entire disclosures of which are incorporated herein by reference.

Alternatively, more than one probe (at least one of which is capable of specifically hybridizing to any complementary sequences which are present in the nucleic acid sample), may be used in an amplification reaction to determine whether the sample contains an organism containing a nucleic acid sequence of the invention (e.g., an organism from which the nucleic acid was isolated). Typically, the probes comprise oligonucleotides. In one embodiment, the amplification reaction may comprise a PCR reaction. PCR protocols are described in Ausubel and Sambrook, supra. Alternatively, the amplification reaction may comprise a ligase chain reaction, 3SR, or strand displacement reaction. (See Barany, *The Ligase Chain Reaction in a PCR World*, PCR Methods and Applications 1:5-16, (1991); Fahy, *Self-sustained Sequence Replication (3SR): An Isothermal Transcription-based Amplification System Alternative to PCR*, PCR Methods and Applications 1:25-33, (1991); and Walker et al, *Strand Displacement Amplification-an Isothermal in vitro DNA Amplification Technique*, Nucleic Acid Research 20:1691-1696, (1992), the disclosures of which are incorporated herein by reference in their entireties). In such procedures, the nucleic acids in the sample are contacted with the probes, the amplification reaction is performed, and any resulting amplification product is detected. The amplification product may be detected by performing gel electrophoresis on the reaction products and staining the gel with an intercalator such as ethidium bromide. Alternatively, one or more of the probes may be labeled with a radioactive isotope and the presence of a radioactive amplification product may be detected by autoradiography after gel electrophoresis.

Probes derived from sequences near the ends of a sequence as set forth in Group A nucleic acid sequences, and sequences substantially identical thereto, may also be used in chromosome walking procedures to identify clones containing genomic sequences located adjacent to the nucleic acid sequences as set forth above. Such methods allow the isolation of genes which encode additional proteins from the host organism.

An isolated nucleic acid sequence as set forth in the Group A nucleic acid sequences, sequences substantially identical thereto, sequences complementary thereto, or a fragment comprising at least 10, 15, 20, 25, 30, 35, 40, 50, 75, 100, 150, 200, 300, 400, or 500 consecutive bases of one of the foregoing sequences may be used as probes to identify and isolate related nucleic acids. In some embodiments, the related nucleic acids may be cDNAs or genomic DNAs from organisms other than the one from which the nucleic acid was isolated. For example, the other organisms may be related organisms. In such procedures, a nucleic acid sample is contacted with the probe under conditions which permit the probe to specifically hybridize to related sequences. Hybridization of the probe to nucleic acids from the related organism is then detected using any of the methods described above.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

Hybridization may be carried out under conditions of low stringency, moderate stringency or high stringency. As an example of nucleic acid hybridization, a polymer membrane containing immobilized denatured nucleic acids is first prehybridized for 30 minutes at 45° C. in a solution consisting of 0.9 M NaCl, 50 mM $NaH_2PO_4$, pH 7.0, 5.0 mM $Na_2EDTA$, 0.5% SDS, 10× Denhardt's, and 0.5 mg/ml polyriboadenylic acid. Approximately $2 \times 10^7$ cpm (specific activity $4-9 \times 10^8$ cpm/μg) of $^{32}P$ end-labeled oligonucleotide probe are then added to the solution. After 12-16 hours of incubation, the membrane is washed for 30 minutes at room temperature in 1× SET (150 mM NaCl, 20 mM Tris hydrochloride, pH 7.8, 1 mM $Na_2EDTA$) containing 0.5% SDS, followed by a 30 minute wash in fresh 1× SET at Tm−10° C. for the oligonucleotide probe. The membrane is then exposed to auto-radiographic film for detection of hybridization signals.

By varying the stringency of the hybridization conditions used to identify nucleic acids, such as cDNAs or genomic DNAs, which hybridize to the detectable probe, nucleic acids having different levels of homology to the probe can be identified and isolated. Stringency may be varied by conducting the hybridization at varying temperatures below the melting temperatures of the probes. The melting temperature, Tm, is the temperature (under defined ionic strength and pH) at which 50% of the target sequence hybridizes to a perfectly complementary probe. Very stringent conditions are selected to be equal to or about 5° C. lower than the Tm for a particular probe. The melting temperature of the probe may be calculated using the following formulas:

For probes between 14 and 70 nucleotides in length the melting temperature (Tm) is calculated using the formula: $Tm=81.5+16.6(\log [Na^+])+0.41(\text{fraction } G+C)-(600/N)$ where N is the length of the probe.

If the hybridization is carried out in a solution containing formamide, the melting temperature may be calculated using the equation: $Tm=81.5+16.6(\log [Na^+])+0.41 (\text{fraction } G+C)-(0.63\% \text{ formamide})-(600/N)$ where N is the length of the probe.

Prehybridization may be carried out in 6×SSC, 5× Denhardt's reagent, 0.5% SDS, 100 µg denatured fragmented salmon sperm DNA or 6×SSC, 5× Denhardt's reagent, 0.5% SDS, 100 µg denatured fragmented salmon sperm DNA, 50% formamide. The formulas for SSC and Denhardt's solutions are listed in Sambrook et al., supra.

Hybridization is conducted by adding the detectable probe to the prehybridization solutions listed above. Where the probe comprises double stranded DNA, it is denatured before addition to the hybridization solution. The filter is contacted with the hybridization solution for a sufficient period of time to allow the probe to hybridize to cDNAs or genomic DNAs containing sequences complementary thereto or homologous thereto. For probes over 200 nucleotides in length, the hybridization may be carried out at 15-25° C. below the Tm. For shorter probes, such as oligonucleotide probes, the hybridization may be conducted at 5-10° C. below the Tm. Typically, for hybridizations in 6×SSC, the hybridization is conducted at approximately 68° C. Usually, for hybridizations in 50% formamide containing solutions, the hybridization is conducted at approximately 42° C.

All of the foregoing hybridizations would be considered to be under conditions of high stringency.

Following hybridization, the filter is washed to remove any non-specifically bound detectable probe. The stringency used to wash the filters can also be varied depending on the nature of the nucleic acids being hybridized, the length of the nucleic acids being hybridized, the degree of complementarity, the nucleotide sequence composition (e.g., GC v. AT content), and the nucleic acid type (e.g., RNA v. DNA). Examples of progressively higher stringency condition washes are as follows: 2×SSC, 0.1% SDS at room temperature for 15 minutes (low stringency); 0.1×SSC, 0.5% SDS at room temperature for 30 minutes to 1 hour (moderate stringency); 0.1×SSC, 0.5% SDS for 15 to 30 minutes at between the hybridization temperature and 68° C. (high stringency); and 0.15M NaCl for 15 minutes at 72° C. (very high stringency). A final low stringency wash can be conducted in 0.1×SSC at room temperature. The examples above are merely illustrative of one set of conditions that can be used to wash filters. One of skill in the art would know that there are numerous recipes for different stringency washes. Some other examples are given below.

Nucleic acids which have hybridized to the probe are identified by autoradiography or other conventional techniques.

The above procedure may be modified to identify nucleic acids having decreasing levels of homology to the probe sequence. For example, to obtain nucleic acids of decreasing homology to the detectable probe, less stringent conditions may be used. For example, the hybridization temperature may be decreased in increments of 5° C. from 68° C. to 42° C. in a hybridization buffer having a $Na^+$ concentration of approximately 1M. Following hybridization, the filter may be washed with 2×SSC, 0.5% SDS at the temperature of hybridization. These conditions are considered to be "moderate" conditions above 50° C. and "low" conditions below 50° C. A specific example of "moderate" hybridization conditions is when the above hybridization is conducted at 55° C. A specific example of "low stringency" hybridization conditions is when the above hybridization is conducted at 45° C.

Alternatively, the hybridization may be carried out in buffers, such as 6×SSC, containing formamide at a temperature of 42° C. In this case, the concentration of formamide in the hybridization buffer may be reduced in 5% increments from 50% to 0% to identify clones having decreasing levels of homology to the probe. Following hybridization, the filter may be washed with 6×SSC, 0.5% SDS at 50° C. These conditions are considered to be "moderate" conditions above 25% formamide and "low" conditions below 25% formamide. A specific example of "moderate" hybridization conditions is when the above hybridization is conducted at 30% formamide. A specific example of "low stringency" hybridization conditions is when the above hybridization is conducted at 10% formamide.

For example, the preceding methods may be used to isolate nucleic acids having a sequence with at least about 97%, at least 95%, at least 90%, at least 85%, at least 80%, at least 75%, at least 70%, at least 65%, at least 60%, at least 55% or at least 50% homology to a nucleic acid sequence as set forth in Group A nucleic acid sequences, sequences substantially identical thereto, or fragments comprising at least about 10, 15, 20, 25, 30, 35, 40, 50, 75, 100, 150, 200, 300, 400, or 500 consecutive bases thereof, and the sequences complementary to any of the foregoing sequences. Homology may be measured using an alignment algorithm. For example, the homologous polynucleotides may have a coding sequence which is a naturally occurring allelic variant of one of the coding sequences described herein. Such allelic variants may have a substitution, deletion or addition of one or more nucleotides when compared to a nucleic acid sequence as set forth in Group A nucleic acid sequences, or sequences complementary thereto.

Additionally, the above procedures may be used to isolate nucleic acids which encode polypeptides having at least about 99%, at least 95%, at least 90%, at least 85%, at least 80%, at least 75%, at least 70%, at least 65%, at least 60%, at least 55% or at least 50% homology to a polypeptide having a sequence as set forth in Group B amino acid sequences, sequences substantially identical thereto, or fragments comprising at least 5, 10, 15, 20, 25, 30, 35, 40, 50, 75, 100, or 150 consecutive amino acids thereof as determined using a sequence alignment algorithm (e.g., such as the FASTA version 3.0t78 algorithm with the default parameters).

Modification to Increase Hydrophobicity of the Interior-Facing Amino Acid Side Chains of the Monomeric Polypeptide One objective of this modification is to enhance the solubility of encapsulated small molecule drugs that are poorly water-soluble when the monomeric polypeptide polymerizes to form a nanoscale drug capsule or delivery vehicle. Poor water solubility is a frequent drawback for many small molecule drugs (see Müller, Jacobs, Kayser, *Nanosuspensions as particulate drug formulations in therapy: Rationale for development and what we can expect for the future*, Adv. Drug Delivery Reviews: v. 47, pp. 3-19 (2001)). The monomeric polypeptide may be modified to produce a nanoscale drug encapsulation device that easily transits in an aqueous environment due to its hydrophilic outer surface while maintaining a favorable environment for hydrophobic small drug molecules on its inner surface.

Modification to Vary Drug-Binding Affinity

A charge environment of a nanoscale drug capsule containing a plurality of the monomeric polypeptide units may affect the rate of drug release. The charge environment may be modified to manipulate the affinity of interactions between the nanoscale drug capsule interior and the encapsulated drug. Changes to the interior that increase the drug affinity of the monomeric polypeptide may lead to slower rates of diffusion and consequently slower rates of drug release. Conversely, changes to the interior that decrease the drug affinity of the monomeric polypeptide may lead to increased rates of drug release.

Modification to Include Antigenic Domains

A polynucleotide sequence selected from SEQ ID NOS. 1, 3, 5, 7, and 9 and sequences substantially identical or complementary thereto, and fragments thereof may be further modified by incorporating one or more sequences encoding one or more antigens therein using a suitable gene modification method such as recombinant DNA or a method described above. In this method, the one or more sequences encoding one or more antigens are inserted into the polynucleotide sequence so that when the polynucleotide sequence is expressed to produce a polypeptide, the antigen or antigenic domain is exposed on the surface of the expressed polypeptide. In a more preferred embodiment, when expressed polypeptide is assembled or self-assembled into a polymer of the present invention, the antigen or antigenic domain is exposed on the surface of the polymer.

These modifications to the monomeric polypeptide may provide an improved drug delivery vehicle with a prolonged circulation lifespan, capable of controlled release of its contents at specific target sites.

In another aspect, the present invention provides a method of producing a polymer including a plurality of the monomeric polypeptide units of the present invention. In the method of producing the polymer of the present invention, a plurality of the monomeric polypeptide units are polymerized under suitable conditions to form the polymer. Preferably, the monomeric polypeptide units are polymerized in the presence of a template molecule. More preferably, the monomeric polypeptide units are polymerized through a self-assembly process in the presence of at least one divalent cation. In a preferred embodiment, the at least one divalent cation may be selected from the group consisting of $Ca^{2+}$, $Mg^{2+}$, $Cu^{2+}$, $Zn^{2-}$, $Sr^{2+}$, $Ni^{2+}$, Mn2+and $Fe^{2+}$. In a more preferred embodiment, the at least one divalent cation includes $Ca^{2+}$. In a most preferred embodiment, the at least one divalent cation includes both $Ca^{2+}$ and $Mg^{2+}$. Most preferably, the method of producing the polymer involves: dissolving the monomeric polypeptides in an aqueous solution, adding the aqueous solution containing the monomeric polypeptides to a container having at least one template molecule and adding $Ca^{2+}$ and $Mg^{2+}$ solutions to the container to polymerize the monomeric polypeptides to form the polymer.

The template molecule used in the present invention may be selected based on the desired properties of the polymer. In a preferred embodiment, the template molecule is prepared by French Press-shearing of a suspension of the polymer of the present invention.

In a preferred embodiment, the polymer of the present invention includes a plurality of monomeric polypeptides having a sequence selected from the group consisting of sequences as set forth in the Group B amino acid sequences and sequences substantially identical thereto. In a more preferred embodiment, the polymer of the present invention includes a plurality of monomeric polypeptides having a sequence selected from the group consisting of SEQ ID NO. 2 and sequences substantially identical thereto. In the most preferred embodiment, the polymer of the present invention includes a monomeric polypeptides having a sequence selected from the group consisting of SEQ ID NO. 2 and sequences substantially identical thereto and a monomeric polypeptide having a sequence selected from the group consisting of SEQ ID NOS 4, 6, 8, and 10 and sequences substantially identical thereto.

In one embodiment, the polymer of the present invention is a hollow tube having approximately a 25 nm outer diameter and a 20 nm inner diameter. The polymer of the present invention preferably has a bending modulus of 5±2 Gpa. At suitable conditions, polymers of the present invention may interact with each other by pairing, bundling, entangling (excluded volume interaction) and electrostatic cross-linking (bridging by divalent cations) to form structures varying from a pair of rods to an interconnected network. A transmission electron micrograph of one embodiment of the polymer (SEQ ID NO:2) of the present invention is illustrated in FIG. 1.

In a further aspect, the present invention relates to a method of delivering a drug molecule to a particular location of a human or animal body. According to the present invention, the method of delivering a drug to a particular location of a human or animal body involves: encapsulating the drug molecule with a polymer of the present invention and administering the encapsulated drug molecule to the human or animal body.

In this method, the encapsulating step may be implemented by forming the polymer in the presence of the drug molecule. Alternatively, the encapsulating step may be implemented by adding the drug molecule to a partially formed polymer and then capping the partially formed polymer using a suitable capping unit such as another monomeric polypeptide unit of the present invention. In another embodiment, the encapsulating step may be carried out by mixing the polymer and the drug molecule together in a solution so that the drug molecule may permeate inside the polymer. In addition, a targeting molecule or vector may be attached to the drug loaded polymer or nanotube during the encapsulation process or after the completion of the encapsulation process. FIG. 2 shows an illustrative diagram of this process. In FIG. 2(A), drug molecules 40 and monomeric polypeptides 42 are dissolved in a solution. In FIG. 2(B), the monomeric polypeptides 40 self-assemble to form a nanoscale polymer 44 encapsulating the drug molecules 40 therein. In FIG. 2(C), targeting vectors 46 are attached to the nanoscale polymer 44.

In another embodiment of encapsulating one or more drugs, in addition to the monomeric polypeptide units, lipids or lipid molecules are used to encapsulate a drug molecule. In this embodiment, liposomes are induced to form from lipids in the presence of both the drug molecules and the monomeric polypeptide units, preferably in a solution, in the presence of a divalent cation such as millimolar calcium and magnesium as described in Akasji et al, *Formation of giant lipsomes promoted by divalent cations: critical role of electrostatic repulsion*, Biophys. J. v. 74, pp. 2973-2982. The formed liposomes encapsulate one or more drug molecules and monomeric polypeptide units therein. After the formation of the liposomes, the condition of the mixture or solution containing the liposomes is changed to, for example, a higher temperature to induce the assembly of the monomeric polypeptide units into polymers or nanotubes to produce a complex wherein the one or more drug molecules are encapsulated in the polymer or nanotube with a lipid coating.

Figure 3A:
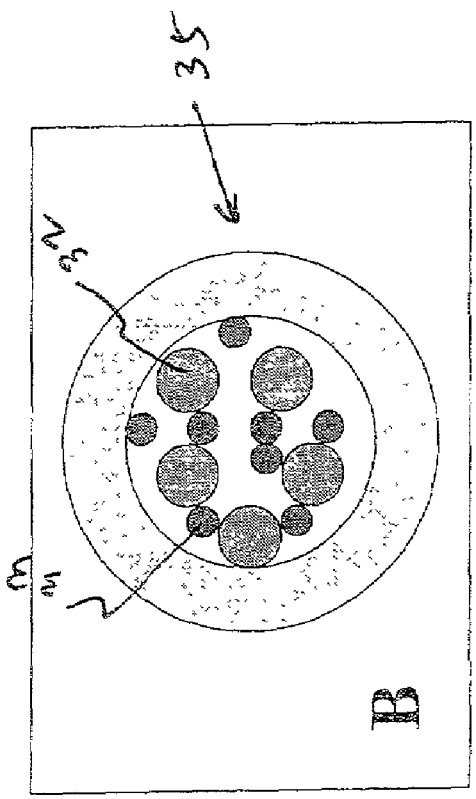
FIG. 3A diagrammatically illustrates a solution containing lipids, monomeric polypeptide units and drug molecules according to the present invention.
Figure 3B:
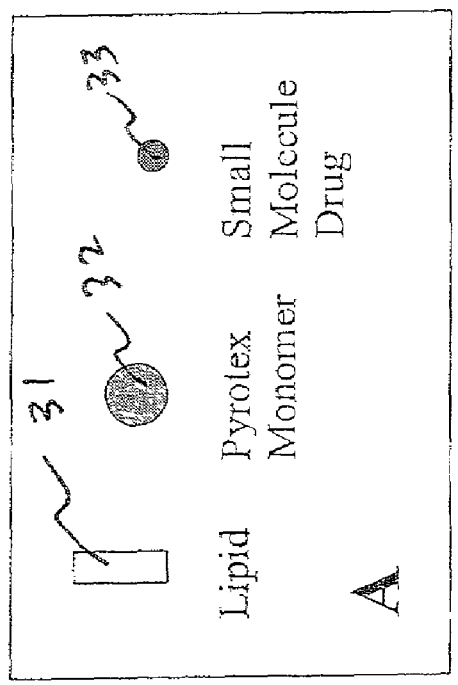
FIG. 3B diagrammatically illustrates a formed liposome encapsulating monomeric polypeptide units and drug molecules according to the present invention.
Figure 3C:
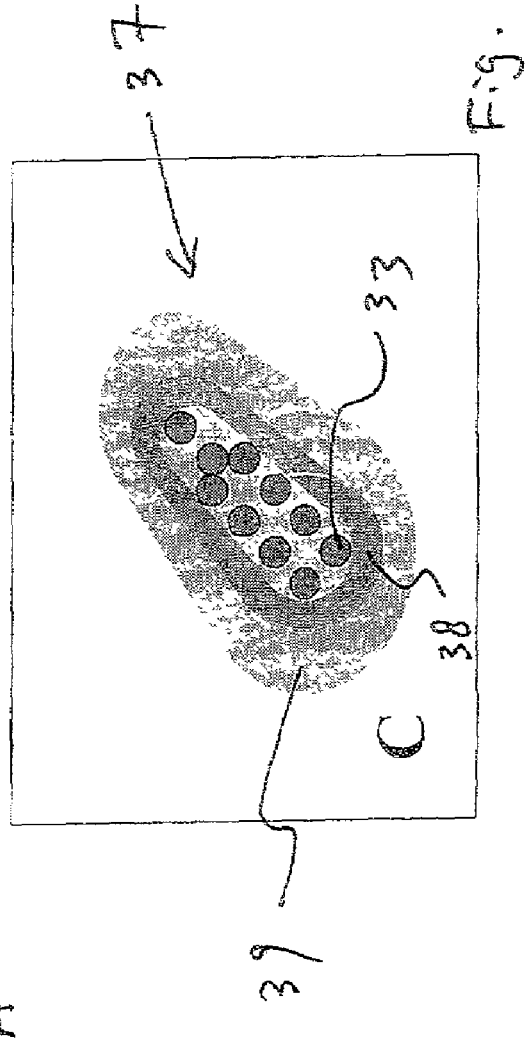
FIG. 3C diagrammatically illustrates an encapsulated drug composition according to present invention.

FIGS. 3A, 3B and 3C further illustrate this process. FIG. 3A illustrates a mixture which may contain a plurality of lipids 31, monomeric polypeptide units 32 and drug molecules 33 (only one lipid, monomeric polypeptide unit and drug molecule is actually shown). The mixture forms a complex 35 as shown in FIG. 3B after a suitable period. Complex 35 contains monomeric polypeptide units 32 and drug molecules 33. The complex 35 in FIG. 3B is further converted to an encapsulated drug composition 37 as shown in FIG. 3C after being incubated for a suitable period of time. Encapsulated drug composition 37 contains drug molecules 33, a polymer 38 made from monomeric polypeptide units 32 and a lipid coating 39.

The encapsulated drug molecule may be administered to a human or animal orally, parenterally, by inhalation or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

The drug molecule may be selected from the currently existing drugs and potential future drugs. Preferably, the drug molecule may be selected from those that are harmful to some organs of the body and, therefore, would preferably be delivered only a particular location in the body. The particular location may be a location where an illness is rooted, an infected location, a tumor location, a damaged location, combinations thereof or equivalents thereof.

After the encapsulated drug molecule has been administered, the encapsulated drug molecule within the polymer may travel to the particular location inside the body because of the body fluid circulation, digestion and similar physiological actions. The movement of the encapsulated drug molecule may be further controlled or targeted by one or more targeting vector existed on the surface of the nanoscale polymer or the polymer of the present invention. The movement may be further regulated by one or more external means such as by irradiating the location, or by planting or injecting a receptor. After reaching the desired location, the drug molecule may be released from the polymer based on a condition of the particular location or on an interaction between the polymer and an element of the particular location. The drug release from the polymer may be controlled by a controlling vector on the polymer responsive to an element of the particular location or an external stimulation such as radiation.

According to the present invention, there may be a multitude of applications for the polymer that combines the possibilities of a nanotube with the physical and chemical manipulability of a simple protein structure. The modulus, length, branching, core diameter, core volume, core and surface polarity, thermo- and solvent stability of the polymer may all be varied by means of mutagenesis and directed protein evolution. Furthermore, the amino acid sidechains facing the core and the external solvent may be utilized as reactive groups for controlled addition of chemical substituents. In addition, arrays of photo- or redox-active groups adopting the underlying spiral symmetry provided by the polymer may be light and electron conductive.

The polymer of the present invention may also be used in various so-called biochip applications. The polymer may be arrayed, on its end, on silicon or aluminum wafers for use as a scaffold to anchor proteins in a high-density, three-dimensional format for protein-protein interaction screening applications. Such an arrayed polymer may be valuable in research to identify and validate novel drug target molecules. Some biochip applications using known probes have been disclosed in U.S. Pat. Nos. 6,174,683 and 6,242,246, which are incorporated by reference hereby in their entirety.

In a preferred embodiment, in order to provide a three-dimensional gel matrix useful in producing a biochip, the polymer chosen to form the gel matrix must have a number of desirable properties. These properties include, for example: 1) adequate pore size and high water content to permit diffusion of molecules in and out of the matrix; 2) the ability to bind to the surface of a substrate, such as glass; 3) sufficient transparency, in its fully polymerized state, to reduce optical interference with fluorescent tags; and 4) sufficient structural integrity, when fully polymerized, to withstand the forces encountered during use. Furthermore, the selected gel is preferably easy to produce and use.

Hydrogels are a class of polymers that meet with these criteria. Hydrogels are hydrophilic network polymers, which are glassy in the dehydrated state and swollen in the presence of water to form an elastic gel. The polyacrylamide gel matrices described in Ershov, et al., are hydrogels having a water content, at equilibrium, of about 95% to 97%, providing favorable diffuseability for target molecules such as DNA's. See for example, U.S. Pat. Nos. 5,741,700, 5,770,721 and 5,756,050, issued to Ershov, et al., on Apr. 21, 1998, Jun. 23, 1998 and May 26, 1998, respectively and U.S. Pat. No. 5,552,270, issued to Khrapko, et al., issued Sep. 3, 1996, each of which patents is hereby incorporated by reference, in its entirety.

In addition to the polyacrylamide gel system of Ershov, et al., polyurethane-based hydrogel polymers are well known and have been used extensively in the production of absorbent materials such as surgical dressings, diapers, bed pads, catamenials, and the like. The polyurethane-based hydrogels used in these materials advantageously absorb large quantities of liquid quickly and in a relatively uniform manner such that the basic overall shape of the gel material is maintained. Further, the moisture absorbed by these materials is retained in the absorbent material even under an applied pressure. Such polyurethane-based hydrogels are described, for example, in U.S. Pat. Nos. 3,939,123, issued to Mathews, et al., Feb. 17, 1976 and 4,110,286, issued to Vandegaer, et al., Aug. 29, 1978, which patents are hereby incorporated by reference, in their entirety.

In a preferred embodiment, the biochip of the present invention uses a hydrogel based on a self-assembling polymer in accordance with the present invention. Alternatively, a the hydrogel may be based on a prepolymer of polyethyleneoxide, or a copolymer of polyethyleneoxide and polypropyleneoxide, capped with water-active diisocyanates and lightly cross-linked with polyols such that the quantity of isocyanates present is predictable for example is at most about 0.8 meq/g. Frequently used diisocyanates include aromatic-based diisocyanates, such as toluene diisocyanate or methylene diphenyl-isocyanate, as well as aliphatic diisocyanates, such as isophorone diisocyanate. The polymerization of the prepolymer, which may be preformulated in water-miscible organic solvent, takes place simply by the addition of water. One advantage of the water-activated polymerization and/or the self-assembly polymerization methods of the present invention is that they allow for derivatization of the prepolymer with an appropriate biomolecular probe prior to or simultaneously with polymerization.

In another embodiment, the self-assembled polymer of the present invention may be attached to the hydrogel to provide, for example, a three-dimensional structural network for the biochip. Attachment to the hydrogel may also be used for other purposes such as self-assembly of complex components of the chip, to provide structural integrity, etc.

In another embodiment, prior to polymerization, the hydrogel is derivatized with a biomolecule such as a probe of the present invention as described above, in an organic solvent using a simple two to three-minute reaction between the probe, preferably peptides or nucleic acids which have been previously derivatized with amine, and the isocyanates of the prepolymer. In order to prevent premature polymerization of the hydrogel in the present embodiment, the derivatization reaction is carried out in aprotic water-miscible organic solvent such as, for example, dimethylformamide (DMF), N-methyl-2-pyrrolidinone (NMP), acetone, acetonitrile or others. Thus, prior to swelling of the hydrogel or dispensing of the hydrogel onto the substrate, biomolecular probes are covalently bound to the polyurethane-based prepolymer gel. Following such derivatization, the addition of water initiates polymerization, resulting in biomolecular-derivatized hydrogels, for example, PNA-derivatized hydrogels.

In this embodiment, the use and presence of aprotic solvent in the derivatization of the hydrogel serves at least four purposes. First, it helps generate a homogeneous solution of the prepolymer in water. Second, it serves to separate the derivatization step from the polymerization step, whereby almost quantitative yield of biomolecule derivatization to the hydrogel can be achieved. Third, it serves to slow down the generation of carbon dioxide during the polymerization step and effervesce carbon dioxide efficiently by lowering the viscosity of the polymerizing mixture. In the polymerization of the polyurethane-based hydrogels preferred herein, carbon dioxide is generated by the reaction of water with the isocyanate groups of the hydrogel prepolymer. Controlling the generation of carbon dioxide and its escape from the gel are critical to providing an effective, useful biochip. If the polymerization occurs too quickly and in a highly viscous mixture, the carbon dioxide generated thereby is not able to escape and becomes trapped within the gel resulting in a discrete foam matrix. While such is not a problem when polyurethane-based hydrogels are used in diapers, bed pads or similar known uses, continuum of the gel matrix is critical in its use in biochips in order to permit accurate and efficient detection of fluorescence indicative of successful hybridization.

A fourth and final advantage to the use of an aprotic solvent to derivatize the hydrogel in the present embodiment is that its presence enhances the optical transparency of the hydrogel by reducing precipitation of the prepolymer. The ratio of aprotic solvent to water must be higher than about 0.25 to allow sufficiently slow polymerization of the gel and, therefore, slow generation of $CO_2$, to result in a continuous and transparent gel matrix, in accordance with the present invention. The total time required for derivatization and polymerization of the hydrogel is most preferably about thirty minutes. This is in stark contrast to the twenty-four to forty-eight hours required for preparation of polyacrylamide based biochips. Furthermore, the quantity of biomolecule such as the probe, for example bound to the prepolymer may easily be adjusted by simply varying the amount of biomolecule added to the reaction (for example, where probe is the biomolecule to be bound to the gel, from about 10 fmol up to about 1 pmol of probes may be used), thereby permitting greater control over the concentration of capture probes within each hydrogel microdroplet.

In this preferred embodiment, the hydrogel is derivatized with the probe then deposited onto the solid substrate, after initiation and before completion of polymerization thereof. This may be accomplished by any convenient method, for example by use of a microspotting machine. The gel is preferably deposited to form an array of microdroplets. It will be appreciated by those of skill in the art that the substrate surface will generally have to be derivatized prior to addition of the hydrogel, for example, in preferred embodiments, where glass is used as the substrate, the glass is derivatized with amine prior to deposit of the polymerizing hydrogel onto its surface. Thus, the polymerizing hydrogel, derivatized with a biomolecular capture probes such as DNAs, is able to bind to the substrate as it is deposited onto the derivatized glass substrate, via reaction of active isocyanate groups within the prepolymer with the amines located on the surface of the glass thereby providing covalent attachment of the hydrogel to the substrate. Most advantageously, all reactions involved in this system, namely (1) the derivatization of hydrogel prepolymer with the biomolecular probe, (2) the polymerization of hydrogel and (3) the binding of derivatized hydrogel to the substrate surface, involve the formation of strong urea bonds. These provide mechanical integrity to the microdroplet array, and significantly increase the half-life of the biochip as compared with the polyacrylamide-based biochip described in the prior art.

In preferred embodiments described herein, the hydrogel droplets, once polymerized on the substrate, are at least about 30 μm thick, more preferably at least about 50 μm thick and most preferably between about 50 μm and 100 μm thick. Furthermore, the droplets will be generally elliptical in shape, as opposed to the square gel cells previously known. It will be readily appreciated that the larger size of the gel droplets (or cells) of the present invention permit a significant increase in the quantity of biomolecular probe immobilized therein, thereby increasing the sensitivity of the biochip and facilitating its use.

In alternative embodiments contemplated herein, water soluble biomolecules, such as the probe of the present invention, DNA or other oligonucleotides, are bound to the hydrogel instead of the organic soluble biomolecules previously described. In these embodiments, it is not possible to first derivatize the hydrogel prepolymer and then initiate polymerization. However, the polyurethane-based hydrogels may be derivatized and polymerized in a single reaction and that such reaction may be adequately controlled to provide a derivatized hydrogel having a relatively predictable quantity of water soluble biomolecular probe attached thereto. In particular, in these embodiments, the hydrogel prepolymer is first dissolved in an organic solvent. The DNA or other water-soluble biomolecule, in aqueous buffer solution, is then added to the prepolymer in a quantity and under appropriate conditions such that the hydrogel is both derivatized with the biomolecular probe and is polymerized. As the hydrogel is polymerizing and before the polymerization is complete, it may be microspotted onto a suitable substrate, as previously described.

Alternatively, the polymer of the present invention may be arrayed in a similar manner as described above, but for the purpose of acting as a molecular sieve. In this embodiment, the arrayed polymer may be used to separate nucleic acid samples as the nucleic acid samples pass through a matrix of the arrayed polymers. Such arrayed polymers may be used in high throughput DNA sequencing or SNP analyses.

The polymer of the present invention may be used as molecular machine components such as shafts or gears, for nanorobots for a wide variety of applications, including biomedical applications. Additionally, the polymer of the present invention may be used as support struts for various structures, or as nanoscopic screws for attachment of tissues during highly intricate surgical procedures. For example, the size of the polymer of the present invention may be controlled through the polymerization conditions and, therefore, the length of the polymer rod may be properly controlled to achieve a desired length. The end units of the polymer (rod) may be varied through using different end capping units. Such a custom designed polymer may be then used as a component in molecular machine or nanomachine.

Attaching one or more enzymes, which catalyze synthesis in a pathway, to one or more of the monomeric polypeptide units in the polymer of the present invention may provide a high-density immobilized, stable, economical biocatalyst for high value chemicals and pharmaceuticals. This type of immobilized biocatalyst may be removed and recycled or destroyed in a controlled way using simple chemical or enzymatic proteolysis.

In addition, the polymer may be used as a universal chiral separating agent based upon the principle of differential interaction of D- and L-isomers with the underlying, L-chiral monomeric polypeptide units contained in the polymer. For example, the polymer of the present invention may be packed or co-packed with a filler into an HPLC column to be used as a chiral HPLC column. Alternatively, the polymer may be immobilized on a substrate such as a cross-linked polystyrene substrate so that the immobilized polymer may be used a chiral separation medium. Depending on the degree of polymerization and the resulting molecular size of the polymer, DNA/RNA/Protein purification resins with different filtration properties may be produced. In a preferred embodiment, the polymer may be used as a separating agent for high value pharmaceutical compounds, which often require not only high chemical purity but also high enantiomatic purity, e.g. containing predominantly one of the enantiomers.

In one preferred embodiment of the method of using the polymer as a separation agent according to the present invention, the polymer may modified by introducing an unsaturated side chain such as a styrene moiety using common synthetic methods such glycosylation using a styrene substituted glycoside. Thereafter, the modified polymer may be copolymerized with styrene and divinylbenzene using emulsion or suspension polymerization methods to form a universal chiral separation resin with the polymer covalently attached to the resin. Alternatively, the styrene and divinylbenzene may be copolymerized in the presence of an unmodified polymer of the present invention to form a resin with the polymer being non-covalently attached. The resin is then packed into an HPLC column and the packed column is installed in a HPLC system to be used to separate pharmaceutical compounds.

Furthermore, the polymer of the present invention may be used a lubricant due to its high thermal stability. For example, the polymer of the present invention may be used as a lubricant either alone or mixed with another known lubricant. This type of lubricant may achieve an improved lubrication efficiency and a wider operating temperature range. Typical lubricants have a relatively narrow operating temperature range because at high temperatures, the viscosity of the typical lubricant tends to be too low to achieve a good lubrication efficiency. On the other hand, at a low temperatures, the typical lubricant may be too viscous to achieve a good lubrication efficiency. However, the polymer of the present invention has a unique molecular shape (rod like), therefore its viscosity vs. temperature profile is much flatter than the typical hydrocarbon lubricant. In a preferred embodiment, the polymer of the present invention may be dissolved in water or other suitable solvent form a lubricant. The concentration of the polymer may be optimized based on the desired operating temperature and molecular weight of the polymer.

The polymer of the present invention may also be used in uniform coating of paint due to its consistent structure. Normally, the conventional coating requires a filler such as $TiO_2$ for both cosmetic and durability purposes. Recently, coatings have been formulated with plastic fillers. However, fillers tend to have one common problem, which is their irregular shape, which makes it difficult to control the rheology of the formulated coating. In contrast, the polymer of the present invention may have a well defined and controlled shape and size. Therefore, the polymer of the present invention may be used as a filler in coating formulations. In addition, the polymer of the present invention may be produced using a biotechnology process such as fermentation. In a preferred embodiment, the coating composition of the present invention may include a uniform blend of one or more polymeric binders dispersed in a liquid medium, which liquid medium consists essentially of at least one component selected from the group consisting of water and organic solvents and a filler, wherein the filler comprises a polymer made by self-assembly of a plurality of polypeptides, wherein each of the plurality of polypeptides has at least 50% homology to a polypeptide having a sequence selected from the group consisting of SEQ ID NOS: 2, 4, 6, 8 and 10.

In another aspect, the polymer of the present invention may be used in place of conventional polymers produced from petrochemicals to produce fibers, plastics and resins. The polymer of the present invention has many advantages over such polymers. For example, the polymer of the present invention has a regular structure. Therefore, one can tailor the properties of the final product of the polymer by controlling the regular structure. Furthermore, the polymer of the present invention may be made from renewable resources. In addition, because of its regular structure, the polymer of the present invention may have some properties such as forming liquid crystals, which allow the strength of the polymer may be increased dramatically.

By incorporating a charged group at one end of the polymer of the present invention, the polymer may align to an electric field. Such aligned polymers would polarize light. By alternating the field applied to the aligned polymers, an optical switch may be produced. There are many applications for such optical switches such as Spatial Light Modulators, "Liquid Crystal" type displays, and optical switches for communications. The methods of forming liquid crystals using the polymer of the present invention are known to a skilled person in the art. In addition, the polymer of the present invention may be used in an optical waveguide. An optical waveguide for processing a beam of light of the present invention includes an elongated body of a light transmitting medium containing one or more liquid crystals therein, the body having first and second sides and entry and exit end faces that extend between the first and second sides, the beam of light entering the body through the entry end face and exiting the body through the exit end face after traveling through the body along a path between the entry and exit end faces; and a first electrode and a second electrode on the first and second sides of the body respectively for establishing an electric field between the first and second sides of the body, wherein said one or more liquid crystals comprises a polymer of the present invention made by self-assembly of a plurality of polypeptides, wherein each of the plurality of polypeptides has a sequence selected from Group B amino acid sequences and sequences substantially identical thereto.

Figure 4:
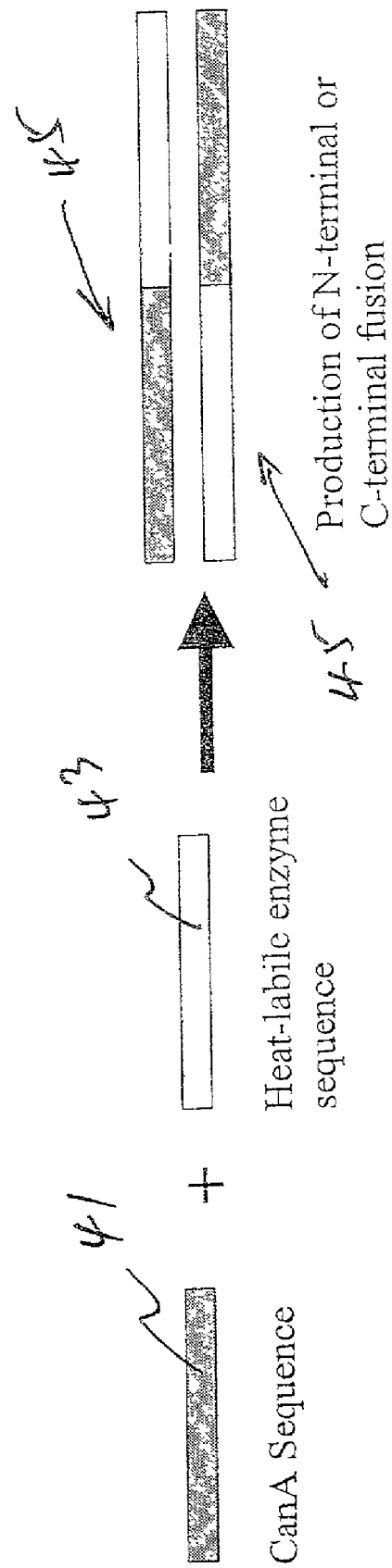
FIG. 4 diagrammatically illustrates a process of fusing a heat stable polypeptide of the present invention with an enzyme to form a heat stable enzyme according to the present invention.

In another aspect, the present invention provides a method of producing a heat stable enzyme. In the method, a first known enzyme may be fused or connected with a second amino acid sequence selected from Group B amino acid sequences and sequences substantially identical thereto to form a third protein or polypeptide having an improved thermal stability in comparison with the first known enzyme by itself. The formed third protein or polypeptide generally contains both the amino acid sequence of the first known enzyme and the second amino acid sequence selected from Group B amino acid sequences and sequences substantially identical thereto and may at least partially retain the enzymatic activities of the first known enzyme. The formed third protein or polypeptide may be further polymerized to form a polymer containing a plurality of the formed third proteins or polypeptides and still at least partially retaining the enzymatic activities of the first known enzyme. The fusion or connecting of the first known enzyme with the second amino acid sequence may be carried out using a chemical method such as reacting the N-terminal of one molecule with the C-terminal of another molecule. Preferably, the fusion may be carried out by fusing a first gene encoding the first enzyme and a second gene encoding the second amino acid sequence together to form a third gene encoding both using standard molecular cloning techniques. The third gene is then cloned into an appropriate over-expression vector and is expressed in suitable host cells or organisms to produce the third protein or polypeptide. Once expressed, the third protein or polypeptide may be purified from the host cells, organisms or proteins by heat treatment to denature the heat-labile host proteins contained in the host cells. Exemplary denaturing conditions are 80° C.-100° C. for 2-20 minutes. The heat-stable third protein or polypeptide is further purified from other contaminating proteins by conventional ion exchange chromatography. The purified third protein or polypeptide may be further polymerized into a polymer by heating a solution containing the third proteins or polypeptides to 80° C. in the presence of millimolar calcium and magnesium cations. The formed polymer may be isolated by centrifugation at 30,000 g for 30 minutes. This process is further illustrated in FIG. 4. Amino acid sequence 41 is a sequence selected from Group B amino acid sequences and sequences substantially identical thereto. Enzyme 43 is an enzyme having a particular enzymatic activity and may be heat labile. Amino acid sequence 41 and enzyme 43 are fused together using a suitable method to form a protein 45, which not only retains at least some of the particular enzymatic activity but also is more thermally stable than enzyme 43.

These fused enzymes or proteins are generally more thermally stable than typical conventional enzymes and, therefore, can be used in applications requiring high operating temperatures. These fused enzymes or proteins, and polymers self-assembled therefrom, may retain one or more of the enzymatic activities of the original unfused enzymes.

The invention will be further described with reference to the following examples; however, it is to be understood that the invention is not limited to such examples.

TABLE 3

Chemicals Used In The Following Examples

| Substance | Source |
| --- | --- |
| α-$^{33}$P-dCTP | NEN, Dreieich |
| α-$^{35}$S-dATP | NEN, Dreieich |
| Acrylamide (reinst) | Serva, Heidelberg |
| Agar (England) | Oxoid, Basingstoke |
| Agarose | Roth, Karlsruhe |
| Agarose low melt | Roth, Karlsruhe |
| Agarose Seakem | Biozym, Hess. Odendorf |
| Ammonium sulfate | Sigma, Deisenhofen |
| Ampicillin | USB, Braunschweig |
| BCIP | Boehringer, Mannheim |
| 2-mercapto-ethanol | Roth, Karlsruhe |

TABLE 3-continued

Chemicals Used In The Following Examples

| Substance | Source |
| --- | --- |
| Bis-Tris | USB, Braunschweig |
| Blocking reagents | Boehringer, Mannheim |
| Bromophenol blue | Serva, Heidelberg |
| Caps | Sigma, Deisenhofen |
| Cesium chloride | Roth, Mannheim |
| CDP-Star ™ chemiluminescence substrate | Boehringer, Mannheim |
| Chloramphenicol | USB, Braunschweig |
| Coomassie brilliant blue R250 | Serva, Heidelberg |
| DEPC | Serva, Heidelberg |
| DIG DNA labeling mixture (10×) | Boehringer, Mannheim |
| DIG Easy Hyb | Boehringer, Mannheim |
| DIG-11-dUTP | Boehringer, Mannheim |
| Didesoxy nucleotides | Boehringer, Mannheim |
| DTT | Serva, Heidelberg |
| EDTA | Serva, Heidelberg |
| Ethanol (97%-99%) | Roth, Karlsruhe |
| Ethidium bromide | Sigma, Deisenhofen |
| Gases and gaseous mixtures | Linde, Munich |
| Glutathione (ox.) | Sigma, Deisenhofen |
| Guanidine hydrochloride | ICN, Eschwege |
| Guanidinium thiocyanate | Sigma, Deisenhofen |
| Yeast extract | Difco, Detroit (USA) |
| IPTG | Boehringer, Mannheim |
| Isoamyl alcohol (3-methyl-1-butanol) | Fluka, Neu-Ulm |
| Iodacetamide | Sigma, Deisenhofen |
| Binding matrix | Sigma, Deisenhofen |
| L-arginine | Aldrich, Steinheim |
| Lauroyl sarcosine | Sigma, Deisenhofen |
| L-cystine | Sigma, Deisenhofen |
| Malachite green hydrochloride | Sigma, Deisenhofen |
| MES | USB, Braunschweig |
| Sodium thiosulfate | Riedel-de-Haën, Seelze |
| NBT | Boehringer, Mannheim |
| N,N-methylene bisacrylamide (2×) | Serva, Heidelberg |
| Nonidet NP 40 | Sigma, Deisenhofen |
| Okadaic acid | ICN, Eschwege |
| Phenol (buffer saturated, Tris (pH 8.0) | Appligene, Heidelberg |
| $^{32}$P$_1$ | Amersham, Braunschweig |
| Ponceau S | Serva, Heidelberg |
| Resazurin | Serva, Heidelberg |
| Rubidium chloride | Sigma, Deisenhofen |
| SDS | Serva, Heidelberg |
| Silicone solution | Serva, Heidelberg |
| Spermidine | Serva, Heidelberg |
| TEMED | Sigma, Deisenhofen |
| Trichloroacetic acid | Riedel-de-Haën, Seelze |
| Tricine | Sigma, Deisenhofen |
| Tris | USB, Braunschweig |
| Triton X-100 | Sigma, Deisenhofen |
| Trypton | Difco, Detroit (USA) |
| Tween 20 | Sigma, Deisenhofen |
| X-gal | AGS, Heidelberg |

All other chemicals were obtained from Merck, Darmstadt.

Unless stated otherwise, all substances were of purity grade p.A.

TABLE 4

Enzymes Used In the Following Examples

| Enzyme | Company |
| --- | --- |
| β-agarase (1 U/μl) | New England Biolabs, Schwalbach |
| Alkaline phosphatase (calf intestine) (5 U/μl) | Promega, Heidelberg |
| Ampli-Taq-DNA polymerase (5 U/μl) | Perkin Elmer, Norwalk (USA) |
| Klenow fragment (2 U/μl) | Boehringer, Mannheim |
| Pfu-DNA polymerase | Stratagene, Heidelberg |

TABLE 4-continued

Enzymes Used In the Following Examples

| Enzyme | Company |
| --- | --- |
| (2.5 U/µl) | |
| Proteinase K | Boehringer, Mannheim |
| Restriction enzymes | Boehringer, Mannheim, and New England Biolabs, Schwalbach |
| RNase, DNase-free (0.5 mg/ml) | Boehringer, Mannheim |
| RNasin ® (40 U/µl) | Promega, Mannheim |
| Subtilisin | Boehringer, Mannheim |
| T4-DNA ligase (1 U/µl) | Boehringer, Mannheim |

TABLE 5

Organisms Used In The Following Examples

| Organism | Reference |
| --- | --- |
| *Pyrodictium abyssi* isolate TAG11 | Deininger W., 1994 |
| *Hyperthermus butylicus* | Zillig et al, 1990; DSMZ 5456 |
| *E. coli* DH5α | Woodcock et al., 1989; [Stratagene, Heidelberg] |
| *E. coli* Y1090 | Young and Davis, 1983; [Stratagene, Heidelberg] |
| *E. coli* BL 21 (DE3) | Phillips et al., 1984; [Stratagene, Heidelberg] |

Other representatives of archaea, which were used for the study of genetic propagation of the cannulae genes, originate from the culture collection of the Regensburg Archaeal Center.

TABLE 6

Oligonucleotides Used In The Following Examples

| Label | Sequence (5' -> 3') | Position (canA) |
| --- | --- | --- |
| M13 forward | GCCAGGGTTTTCCCAGTCACGA | — |
| M13 reverse | AGCGGATAACAATTTCACACAGG | — |
| T3 promoter | ATTAACCCTCACTAAAG | — |
| T7 promoter | TAATACGACTCACTATAGGGG | — |
| T7 terminator | CTAGTTATTGCTCAGCGG | — |
| TUB-F2 | CAGAGCCCC/GCTCAA | 82-95 |
| PAL-F1 | GCAGCTAAAGCCCTACTTCA | 276-295 |
| V.F1 | CAGCTTCTACGCCACCGG | 96-113 |
| TA-EX-F1 | TGTGAAGTACACAACCCTAGC | −1-20 |
| R29-REV1 | GCGCCGGCTGCGGGGG | 185-170 |
| V.R1 | CTGTGCTGTACCGGTGGCG | 123-105 |
| Pal-R1 | AGCATACCCTCCTTAGCCTC | 572-553 |

In addition, a nucleic acid sequence with SEQ ID NO. 1 and an amino acid sequence with SEQ ID NO. 2 are also called CanA, since both sequences encode a protein called Cannule A. For the same reason, SEQ IDS NOS. 3 and 4 are called CanB; SEQ ID NOS. 5 and 6 are called CanC; SEQ ID NOS. 7 and 8 are called CanD; and SEQ ID NOS. 9 and 10 are called CanE.

TABLE 7

Plasmids Used In The Following Examples

| Plasmid | Size | Property | Reference |
| --- | --- | --- | --- |
| PBluescript ® II phagemid KS(-) | 2.96 kb | AmpR; MCS flanked by T3 and T7 promoter; replication vector | Alting-Mees et al., 1989; [Stratagene, Heidelberg] |
| pET17b | 3.31 kb | AmpR; MCS flanked by T7 promoter and T7 terminator; expression vector | Studier et al., 1990; [AGS, Heidelberg] |

EXAMPLE 1

Media and Cultivation of Organisms a) Anaerobic Cultivation of Hyperthermophilic Organisms in Serum Flasks i. Preparation of Synthetic Sea Water (also called "SME"): NaCl (27.70 g); $MgSO_4 \times 7\ H_2O$ (7.00 g); $MgCl_2 \times 6\ H_2O$ (5.50 g); KCl (0.65 g); NaBr (0.10 g); $H_3BO_3$ (0.03 g); $CaCl_2 \times 2\ H_2O$ (0.75 g); $SrCl_2 \times 6\ H_2O$ (15.00 mg); and KJ (0.50 mg) were added a Schott flask. To the Schott flask, $H_2O_{bidist}$ was added until the total volume of the mixture in the Schott flask reaches 1,000 ml. After the complete dissolution of the chemicals, the mixture was gassed with nitrogen for 20 min. (max. 1 bar, color change of the nitrogen indicator resazurin from bluish purple to red). For the reduction, 20 ml of 2.5% (w/v) anaerobic $Na_2S$ solution was injected per liter medium. After complete decoloration of the medium, the pH value was set, as desired, with 25% (v/v) anaerobic $H_2SO_4$.

Serum flasks (glass type III; Bormioli, Italy) were flushed twice with $H_2O_{bidist}$ and dried at 100° C. for 2 hours. Then each flask was filled with 20 ml above medium in an anaerobic chamber (Coy-Lab Products; Ann Arbor, Mich., USA) under $N_2/H_2$ atmosphere (95/5; v/v), plugged with rubber stoppers and the rubber stopper were sealed with aluminum caps ("aluminum seal stoppers"; Belco Glass; New Jersey, USA). Prior to use, the rubber stoppers were boiled once in 0.2% HCl and twice in $H_2O_{bidist}$ for one hour each. After autoclaving (thiosulfate in the medium; 20 min., 121° C., 2 bar) or vaporizing (sulfur in the medium; 1 hour, 100° C.), each of the serum flasks was evacuated three times alternatingly at a gas station and gassed aseptically with $H_2/CO_2$ (80/20, v/v, 2 bar).

ii. Medium for *Pyrodictium abyssi* (pH 5.5-6.0)

The medium contained SME (500.00 ml); $KH_2PO_4$ (0.50 g); Yeast extract (0.50 g); $Na_2S_2O_3$ (1.00 g); Resazurin (1%) (0.30 ml); and enough $H_2O_{bidist}$ so that the total volume of the medium was 1,000 ml. The medium was autoclaved. The cultivation temperature was 102° C. The incubation of *Pyrodictium abyssi* was carried out while standing.

iii. Medium for *Hyperthermus* (pH 7.0)

The medium contained SME (500.00 ml); $KH_2PO_4$ (0.50 g); $NH_4Cl$ (0.50 g); Sulfur (5.00 g); KJ (2.50 mg); $NiSO_4 \times 6\ H_2O$ (2.00 mg); Resazurin (1%) (0.30 ml); and enough $H_2O_{bidist}$ so that the total volume of the medium was 1,000 ml. The medium was vaporized. Prior to inoculation, 6 g trypton per liter were added in the form of an autoclaved stock solution (10%, w/v). The cultivation temperature was 100° C. The incubation of Hyperthermus was carried out while standing.

b) Media and Conditions for *Escherichia coli*

The diverse *E. coli* strains were routinely cultivated aerobically on $LB_0$ medium (see below) at 37° C. with intensive shaking (250 rpm). Plasmid-carrying strains with resistance to antibiotics were cultivated in the presence of the corresponding antibiotic (100 μg/ml) ampicillin, 34 μg/ml chloramphenicol).

i. $LB_0$ Medium for *E. coli* DN5α and BL 21 (DE3), (pH 7.0)

The medium contained Trypton (10.00 g); Yeast extract (5.00 g); NaCl (10.00 g); and enough $H_2O_{bidist}$ so that the total volume of the medium was 1,000 ml.

ii. $LB_0$ Medium for *E. coli* Y1090 (pH 7.0)

The medium contained Trypton (10.00 g); Yeast extract (10.00 g); NaCl (5.00 g); and enough $H_2O_{bidist}$ so that the total volume of the medium was 1,000 ml.

iii. NZYM Medium for *E. coli* Y1090 (pH 7.0)

The medium contained NZ amines (10.00 g); NaCl (5.00 g); Yeast extract (5.00 g); $MgSO_4 \times 7\ H_2O$ (2.00 g); and enough $H_2O_{bidist}$ so that the total volume of the medium was 1,000 ml.

For the preparation of plates, 15 g agar per liter medium was used. 7.5 g agarose per liter medium was added to the Top Agar.

EXAMPLE 2

Preparation of Competent Cells

DH5α and BL 21 (DE3) cells were made competent with rubidium chloride for the uptake of plasmid DNA from the medium. The materials used as listed as following:

| SOB: | |
| --- | --- |
| Trypton | 5.00 g |
| Yeast extract | 1.25 g |
| 5 M NaCl | 0.50 ml |
| 3 M KCl | 0.21 ml |
| $H_2O_{bidist}$ | up to 250.00 ml |
| Glucose Solution (50 ×): | |
| Glucose | 3.96 g |
| $MgSO_4 \times 7\ H_2O$ | 2.46 g |
| $MgCl_2 \times 6\ H_2O$ | 2.03 g |
| $H_2O_{bidist}$ | up to 20.00 ml |

SOC Medium: 98 ml SOB + 2 ml 50 × glucose solution

| Transformation buffer: | TF I | TF II |
| --- | --- | --- |
| RbCl | 1.20 g | 36.00 mg |
| $MnCl_2 \times 4\ H_2O$ | 0.99 g | — |
| $CaCl_2 \times 2\ H_2O$ | 0.15 g | 0.33 g |
| 87% glycerol | 15.00 g | 4.50 g |
| 1 M potassium acetate (pH 7.5) | 3.00 ml | — |
| 0.5 M MOPS | — | 0.60 ml |
| $H_2O_{bidist}$ | up to 100.00 ml | up to 30.00 ml |
| pH | 5.8 | 6.8 |

For TF I, the pH value was adjusted with acetic acid (15%). For TF II, the PH value was adjusted with a sodium hydroxide solution (5 M). The transformation buffer and the glucose solution were sterilized by filtration. The SOB medium was autoclaved.

First, 10 ml SOC medium was inoculated with a single colony of the desired *E. coli* strain and shaken at 37° C. overnight. 1 ml of this overnight culture was used as the inoculum for 100 ml SOC medium and incubated with shaking at 37° C. At an $OD_{600}$ of 0.4, the culture was distributed over three pre-cooled centrifuge beakers (JA 20 rotor). After standing for 15 minutes on ice, the cells were harvested (JA 20 rotor, 5 min. 7,000 rpm, 4° C.). The cell pellet of each beaker was absorbed in 11.4 ml ice cold TF I, put on ice for 15 min. and collected by centrifugation again (JA 20 rotor, 5 min, 7,000 rpm, 4° C.). Then each pellet was carefully resuspended in 2.9 ml ice cold TF II, proportioned (50 μl) and shock frozen in liquid nitrogen. The competent cells were stored at −80° C.

EXAMPLE 3

Cell Lysis Buffer (pH 8.0)

| The cell lysis buffer contained: | |
| --- | --- |
| Tris | 0.20 M |
| NaCl | 0.10 M |
| Na citrate | 1.00 mM |
| EDTA | 1.00 mM |

EXAMPLE 4

Mechanical Cell Lysis

This cell lysis method was applied to *Methanopyrus kandleri, Methanothermus fervidus* and *Pyrobaculum aerophilum*.

In a precooled mortar approximately 0.5 g frozen cells were ground to a fine powder under liquid nitrogen. Following addition of 1-2 ml lysis buffer (see example 8) and thawing to room temperature, the suspension was introduced into an Eppendorf reaction vessel. Then the same procedure as described in example 10 was followed.

EXAMPLE 5

Cell Lysis with Subtilisin

With the exception of the aforementioned organisms in Example 9, all organisms for DNA isolation were lyzed as follows: 0.05-0.1 g cells were suspended with 500 μl lysis buffer (see example 8). Together with subtilisin (final concentration: 40 ng/μl) and 2 μl RNase, DNase-free, the suspension was incubated in the water bath at 37° C. for 30 minutes. Then the same procedure as described in Example 11 was followed.

EXAMPLE 6

Phenol/Chloroform Extraction

This method of DNA cleaning was chosen for all organisms, whose DNAs were used for studying the propagation of cannulae genes. DNA solutions were pipetted with cut off pipette tips in order to largely avoid shear forces.

500 μl cell lysis (Examples 9 and 10) was treated with 500 μl buffer-saturated phenol and carefully mixed in an Eppendorf Reaction Vessel (ERV). For phase separation, the mixture was centrifuged in an Eppendorf centrifuge for 5 minutes at 13,000 rpm. After centrifugation, the DNA-containing solution (top layer) was transferred into a clean ERV, and treated with 205 μl phenol. Following careful swirling, 250 μl chloroform/isoamyl alcohol (24/1) were added, and the phases were mixed again. Following phase separation, the last step was repeated until there was no longer a white layer of proteins between the two phases. Finally the DNA suspension was treated with 500 µl chloroform/isoamyl alcohol (24/1, v/v), centrifuged for the last time, and the aqueous phase was transferred into a clean ERV.

To remove the phenol groups and to concentrate, the DNA was precipitated with ethanol. At the same time 1/10 volume 3M sodium acetate and 2.5 volume ethanol$_{absolute}$ (−20° C.) were added; the DNA was precipitated at −80° C. for 30 min. and collected by centrifugation in a table centrifuge (30 min., 12,000 rpm, 4° C.). The pellet was washed with 200 µl 70% ethanol (−20° C.), centrifuged at 4° C. for 15 min., and dried in the desiccator for 15 min. Then the DNA was absorbed in 100 µl distilled water, treated with RNase, DNase-free (2 µl), and incubated for 30 min at 37° C. Then the DNA solution was stored at 4° C.

EXAMPLE 7

CsCl Gradient Equilibrium Centrifugation

The DNA of the Pyrodictium abyssi isolate TAG11 was cleaned in the CsCl gradient by equilibrium centrifugation. One exception was the test for the genetic propagation of the cannulae genes. The same protocol was followed as described above. The DNA of 0.5 g *Pyrodictium* cells was resuspended in 1 ml H2O$_{bidist}$.

EXAMPLE 8

Isolation of Plasmid DNA from *E. Coli* a). Buffer and Solutions Used in this Example

| S1 buffer: | Tris/HCl (pH 8.0) | 50 mM |
| --- | --- | --- |
| | EDTA | 10 mM |
| S2 buffer: | NaOH | 200 mM |
| | SDS | 1% |
| S3 buffer: | KAc/HAc (pH 5.2) | 2.6 M |
| N2 buffer: | Tris/H$_3$PO$_4$ (pH 6.3) | 100 mM |
| | KCl | 900 mM |
| | EtOH | 15% |
| N3 buffer: | Tris/H$_3$PO$_4$ (pH 6.3) | 100M mM |
| | KCl | 1150 mM |
| | EtOH | 15% |
| N5 buffer: | Tris/H$_3$PO$_4$ (pH 8.5) | 100 mM |
| | KCl | 1000 mM |
| | EtOH | 15% |
| Binding solution: | guanidinium thiocyanate | 4 M |
| | Tris/HCl (pH 7.5) | 50 mM |
| | EDTA | 20 mM |
| | binding matrix | 10 mg/ml |
| Wash buffer: | NaCl | 200 mM |
| | Tris/HCl (pH 7.5) | 20 mM |
| | Na$_2$EDTA | 5 mM |

Prior to use, the wash buffer was diluted 1:1 with EtOH$_{absolute}$.

b). Preparation on the Mini Scale

Of the 10 ml *E. coli* overnight culture in LB$_0$ medium, 4 ml were collected by centrifugation in an ERV (table centrifuge, 3 min., 12,000 rpm). The pellet was resuspended in 100 µl S1 buffer and treated with 1 µl RNase, DNase-free, (0.5 mg/ml). Lysis took place by adding 200 µl S2 buffer at RT for 5 min. After neutralization with 200 µl S3 buffer, the batches were put on ice for 5 to 10 min. Then the chromosomal DNA, cell groups and precipitated DKS were pelletized (table centrifuge, 5 min., 12,000 rpm). The supernatant was mixed with 1 ml binding solution and incubated at RT for least 20 min. In the interim the sedimented binding matrix was agitated several times. Then collection by centrifugation followed (table centrifuge, 2 min., 12,000 rpm); and the supernatant was discarded. After washing twice in 1.5 ml wash buffer each, the pellet was dried in the desiccator for 15 min. and resuspended in 120 µl H$_2$O$_{bidist}$. For quantitative elution of the DNA, the suspension was incubated at 60° C. for 10 min. After slowly cooling, the binding matrix was sedimented (table centrifuge, 5 min., 12,000 rpm) and the plasmid-containing supernatant was transferred into a new ERV.

EXAMPLE 9

Analysis and Cleaning of DNA a) Concentration Measurement
  i. Photometric Determination The concentration of dissolved DNA was determined by measuring the optical density (OD) at 260 nm. A 1:20 dilution of the DNA solution was used. From the measured value, the concentration of the undiluted DNA solution was then determined:

OD$_{260\ nm}$ of the 1:20 dilution≈µg/µl [DNA$_{undiluted}$]

ii. Ethidium Bromide Plates

If there were only very low concentrations or absolute quantities of DNA, then they were estimated by comparing with the standard concentrations.

| Plates: | |
| --- | --- |
| agarose | 5.0 g |
| 1 M Tris/HCl (pH 7.5) | 5 ml |
| 0.5 M EDTA (pH 8.0) | 1 ml |
| ethidium bromide (10 mg/ml) | 0.25 ml |
| H$_2$O$_{bidist}$ | up to 500 ml |

The agarose was dissolved in water by boiling. After cooling to approx. 60° C., the remaining components were added. The solution was poured into Petri dishes (Sarstedt, Ulm). Following solidification, 1 µl each of the DNA solution of unknown concentration was pipetted to the plates in parallel with DNA standards (10-100 ng/µl). After approx. 5 minutes, the fluorescent intensity of the standard and of the sample in UV light was compared and thus the unknown concentration was estimated.

The finished plates can be stored under light protection for several weeks at 4° C.

b) Agarose Gel Electrophoresis
  i. Buffer and Solutions

| TAE running buffer (10 ×): | |
| --- | --- |
| Tris/acetate pH (8.35) | 400 mM |
| Na$_4$ EDTA | 10 mM |
| Application buffer: | |
| EDTA | 50 mM |
| saccharose | 40% |
| bromophenol blue | 0.1% |
| xylene cyanol | 0.1% | ii. Protocol

For the analysis of PCR products, plasmids, and genomic DNA, 0.8-2.5% agarose gels were used. In the subsequent elution from the gel (see example 14.b), a low melting agarose was used. Sea-Kem agarose was used, when the DNA was blotted on a membrane following electrophoretic separation (see example 19.d).

The agarose was dissolved in $H_2O$ by boiling. After cooling under flowing water and addition of 1/10 volume 10×TAE and 1/10,000 volume ethidium bromide (10 mg/ml), the gel solution was poured into a horizontal gel chamber (30 ml: 7×10 cm or 200 ml: 20×22 cm). The samples were treated with 1/5 volume application buffer prior to application. The gel run took place in 1×TAE at 80-120 V for 30-90 minutes. The separation was controlled on a UV fluorescent screen and evaluated and documented with an EASY image analysis system (Herolab, Heidelberg).

c) Isolation of DNA from Agarose Gels

To isolate single restriction fragments, the batches were separated using an agarose gel (1%) with a special, low melting agarose. The desired bands were cut out under UV light and the agar blocks were weighed (1 mg≈1 µl).

After being filled with $H2O_{bidist}$ up to 9/10 reaction volume, and being added with 1/10 volume 10×agarase buffer, the agar block was melted with frequent, intensive shaking at 65° C. for 10 min. After 5 min. pre-incubation at 40° C., 1 µl β-agarase (1 unit) was added to the melted agar block to form a mixture. The mixture was incubated for another hour at 40° C., during which period there was frequent mixing. The mixture was put on ice for 10 min. and then collected by centrifugation in a table centrifuge at 12,000 rpm at RT for 10 min. The DNA was precipitated from the supernatant with ethanol (see example 11).

EXAMPLE 10

Polymerase Chain Reaction (PCR)

The reaction was conducted in 0.2 ml reaction vessels (Stratagene, Heidelberg). Upon the start of the reaction, the reaction was kept on ice and the DNA polymerase was always added last. The batches were coated with the same volume of Chill-out 14™ liquid wax (MJ Research, Inc., Nalgene) in order to check the evaporation during the reaction. (After setting up the Thermo-Cycler with a heatable cover, this coating was no longer necessary.) The amplification took place in a Robocycler (gradient 96, Stratagene). The PCR products were cleaned with the High Pure PCR Purification kit from Boehringer (Mannheim) and analyzed by agarose gel electrophoresis (see example 14.b).

a) Standard PCR

To amplify specific segments of the chromosomal DNA and to estimate the size and orientation of the insert for plasmids, cleaned DNA was used as the matrix.

| Reaction batch: | |
|---|---|
| Taq PCR buffer (10×) | 2.5 µl |
| dNTP (per 2.5 mM) | 2.0 µl |
| primer A (20 pMol/µl) | 0.5 µl |
| primer B (20 pMol/µl) | 0.5 µl |
| plasmid DNA (5 ng/µl) | 2.0 µl |
| Taq DNA polymerase (5 U/µl) | 0.13 µl |
| $H_2O_{bidist}$ | 17.37 µl |
| Taq PCR buffer (10 ×): | |
| Tris/HCl (pH 8.3) | 100 mM |
| KCl | 500 mM |
| $MgCl_2$ | 15 mM |

Program: 3 min 95° C., 32 × (1 min. 95° C., 1 min. 55° C., 1.5 min. 72° C.), 10 min 72° C.

For PCR products that were more than 1,500 bp long, the polymerization time (72° C.) per 1,000 bp was increased by 1 minute.

With the addition of chromosomal DNA, 50 ng were used as the matrix.

b) PCR Screening

This method was used to check the insert size of diverse clones by means of PCR. Used was the primer pair M13 lac Z (reverse and forward, Perkin Elmer), which bind to the flanking regions of the multiple cloning site of the KS(−) vector. Either 5-10 ng cleaned plasmid DNA or whole plasmid-containing cells were added as the matrix (to this end, the colonies were picked from the $LB_0$ plate with sterilized toothpicks).

Program: 5 min 95° C., 32×(1 min. 95° C., 1 min. 55° C., 2-5 min. 72° C.), 10 min 72° C.

c) Introduction of Restriction Sites with PCR

To construct expression plasmids, DNA fragments had to be inserted into the expression vector (pET17b) in a precisely defined reading frame. Therefore, it was necessary to insert new restriction sites at the 5' and 3' end of the protein-coding DNA segment. For this reason, the gene was amplified with two primers, which contained the respective restriction sites at the corresponding places. At translation start (ATG), a NdeI site (CATATG) was inserted; after the translation stop (TAA) a NotI site (CGCCGGCG) was inserted. The resulting PCR product could then be inserted into the expression vector by means of the newly created restriction sequences. To guarantee the minimum probability of error in the DNA synthesis, Pfu-DNA polymerase was used here. It contains a 3'->5' exonuclease activity (proofreading), which enables the splitting off of the nucleotides that have been incorrectly incorporated at the 3' end of the synthesized DNA strand.

| Batch: | |
|---|---|
| pfu-PCR buffer (10×) | 2.5 µl |
| dNTP (per 2.5 mM) | 2.0 µl |
| primer * EX-F * (20 pMol/µl) | 0.5 µl |
| primer * EX-R * (20 pMol/µl) | 0.5 µl |
| plasmid DNA (5 ng/µl) | 1.0 µl |
| Pfu-DNA polymerase (2.5 U/µl) | 0.26 µl |
| $H_2O_{bidist}$ | 18.24 µl |
| Program: | |
| CanA: | 3 min 95° C., 32 × (1 min. 95° C., 1 min. 20 s 65° C., 1 min. 15 s 72° C.), 10 min 72° C. |
| CanB: | 3 min 95° C., 32 × (1 min. 95° C., 1 min. 20 s 63° C., 1 min. 15 s 72° C.), 10 min 72° C. |
| CanC: | 3 min 95° C., 32 × (1 min. 95° C., 1 min. 20 s 55° C., 1 min. 15 s 72° C.), 10 min 72° C. |

-continued

Expression primer:

| | |
|---|---|
| CAN-EX-FA/B: | 5'-TAGCAGGCCATATGACCACCCAGAGCCCCC-3' |
| CAN-EX-FC: | 5'-CTAGCAGGCCATATGACGACCCAGAGCC-3' |
| CAN-EX-RA: | 5'-GGAGGACTGGCGGCCGCTGTTAGCCTAC-3' |
| CAN-EX-RB: | 5'-AGTAGCTAGCGGCCGCTTTAGCTGACGC-3' |
| CAN-EX-RC: | 5'-GGCCGTGGCGGCCGCTGCTTCACC-3' |

The inserted restriction sites are underlined.

d) RT PCR

RT PCR is one of the most sensitive methods to determine the presence or absence of specific RNA molecules or to quantify the strength of the gene expression. In contrast to a normal PCR, in a RT PCR process, RNA is used as the matrix, which can be translated back into DNA by reverse transcriptase (RT). The next step of the RT PCR process is a "normal" PCR, where the newly synthesized DNA is used as a template and is amplified.

In the present study, a Titan™ One Tube RT PCR system (Boehringer, Mannheim) was used. In the first step of the RT PCR process, AMV reverse transcriptase was used for the first strand synthesis. An Expand™ High Fidelity Enzyme Mix (Taq DNA polymerase and Pwo DNA polymerase) is used for the "normal" PCR step of the RT PCR process. The following batch was made according to the standard:

Master mix 1: 4 µl dNTP (per 2.5 mM), 4 µl primer 1 (5 pM/µl), 4 µl primer 2 (5 pM/µl), 2.5 µl DTT (100 mM), 6 µl RNase inhibitor (1 U/µl), 1 µl mRNA (1 pg-1 µg), up to 25 µl DEPC-$H_2O$ Master mix 2: 10 µl 5×RT buffer with $Mg^{2+}$, 1 µl enzyme mix, up to 25 µl DEPC-$H_2O$ The two master mixes were combined, mixed, centrifuged and put into the preheated (60° C.) block of the thermocycler.

Program: 30 min. 60° C., 2 min. 94° C., 10×(1 min. 94° C., 1 min. 55° C., 1 min. 15 s 68° C.), 20×(1 min. 94° C., 1 min. 55° C., 1 min. 35 s 68° C.), 5 min 72° C.

EXAMPLE 11

Cloning of DNA Fragments a) Restriction Hydrolysis

The double stranded DNA was cleaved with restriction enzymes for at least two hours at 37° C. in the water bath.

b) Dephosphorylation of DNA Fragments

To suppress the religation of linearized vectors, the sites at the 5' end were dephosphorylated with alkaline calf intestine phosphatase (CIP). To this end, the restriction batches were filled, according to the standard, up to 45 µl with $H_2O$ following phenol/chloroform treatment and DNA precipitation (see example 11). 5 µl 10×phosphatase buffer (0.5 M Tris/HCl (pH 9.10), 10 mM $MgCl_2$, 1 mM $ZnCl_2$, 10 mM spermidine) and 1 µl CIP (1 U/µl) were added and incubated at 37° C. for one hour. After a second addition of CIP (1 µl), the incubation was continued for another hour. Then the batches were phenol-extracted and precipitated with ethanol (see example 11).

c) Filling up of Overhanging Ends

The ends of the PCR products or restriction fragments were filled in with T7 polymerase. For example, 50 µl cleaned restriction batch were treated with 5 µl $H_2O$, 7 µl restriction buffer (Boehringer, Mannheim), 6 µl dNTP (per 2.5 mM), and 2 µl T7 polymerase and incubated in the water bath at 37° C. for one hour. After inactivation of the polymerase (20 min, 65° C.), the batch was cleaned with the High Pure PCR Purification kit from Boehringer (Mannheim).

d) Production of a T Vector

To clone the PCR products, a so-called T vector was produced. For example, the vector pBluescript KS(−) was linearized with EcoRV (see example 16 a)) and then incubated in the presence of 2 mM dTTP with Taq polymerase (1 U/µg vector) at 70° C. for 2 hours. The reaction took place under standard buffer conditions (50 mM KCl, 10 mM Tris (pH 8.3), 1.5 mM $MgCl_2$ and 200 µg/ml BSA). The reaction volume was 20 µl. Following phenolation and ethanol precipitation (see example 11), the T vector was resuspended in TE buffer (10 mM Tris/HCl (pH 8.0), 1 mM EDTA); and a concentration of 60 ng/µl was set.

e) Ligation of DNA Fragments $100\text{-}120\times10^{-15}$ mole fragment and $30\text{-}40\times10^{-15}$ mole digested vector DNA were transferred into a 10 µl vessel. The bonding took place in a buffer, provided by the manufacturer, with 1 U T4 DNA ligase overnight at 16° C.

f) Transformation

50 µl competent cells were thawed on ice, 2 µl 0.5 M 2-mercapto ethanol and 3 µl ligation batch (see example 16.e) were added to the competent cells and carefully stirred with the pipette tip. Then the mixture was incubated on ice for 30 min. After 30 s at 42° C., the mixture was put on ice again for 1-2 minutes. After addition of 450 µl fresh sterile SOC medium (see example 7), the mixture was temperature controlled at 37° C. in the water bath for 1-2 minutes for fast temperature conformation. The transformation mixture was shaken at 37° C. for 60 min. and then plated out repeatedly 200 µl per $LB_0$ plate (treated with 100 µl ampicillin (10 mg/ml), 100 µl X-gal (20 mg/ml in formamide) and 10 µl IPTG (0.1 M)). The plates were incubated at 37° C. overnight. The pretreatment with X-gal and IPTG allowed a blue/white screening of the transformants. Colonies of transformants with an insert in the incorporated vector appeared white; without the insert, blue.

g) Glycerol Cultures

Long-term cultures, also called glycerol cultures, were prepared from the transformed E. coli strains. For example, 2 ml overnight culture pellet were collected by centrifugation; the pellet was resuspended in 140 µl fresh $LB_0$ (see example 6.b), thoroughly mixed with 200 µl sterile glycerol (87%) and deep frozen at −80° C.

EXAMPLE 12

Sequencing a) Plasmids

The sequencing reaction was conducted with the sequenase Quick Denature™ Plasmid Sequencing kit from USB. In contrast to the manufacturer's recommended termination reaction temperature, the termination reactions were conducted at 45° C. (thermoblock). The radioactive marking was done with $^{35}$S-dATP.

b) PCR Products

The sequencing reactions were conducted with the Ampli-Cycle™ Sequencing kit from PERKIN ELMER in a thermocycler. The radioactive marking was done with $^{33}$P-dCTP.

| Annealing mix: | |
| --- | --- |
| PCT product (cleaned) | 100 ng |
| primer | 10 pMol |
| H$_2$O | up to 15 µl |
| Cycling master mix: | |
| H$_2$O | 10.75 µl |
| α-$^{33}$P-dCTP (10 µCi) | 0.25 µl |
| cycling mix | 4.00 µl |

2 µl of each of the termination mixes was transferred into a 0.2 ml PCR tube on ice. The annealing mix and cycling master mix were combined and mixed to form a mixture. 6 µl of this mixture was pipetted (on ice) to each of the termination mixes in the PCR tubes. The PCR tubes were then transferred to the preheated thermocyclers and the program was started. At the end of the program, 4 µl stop solution was added and the samples in the PCR tubes were frozen until gel application. Program: 2 min 94° C., 32×(1 min 94° C., 75 s 55-65° C., 65 s 72° C.), 5 min 72° C. The annealing temperature varied as a function of the oligonucleotide that was used.

c) Phage DNA

To sequence phage DNA, the same protocol as described in example 17.b was followed. However, instead of 100 ng PCR product, 1 µg phage DNA was added to the annealing mix. Program: 2 min 94° C., 32×(1 min 94° C., 75 s 50° C.,65 s 72° C.), 5 min 72° C.

d) Polyacrylamide Urea Gel Electrophoresis

The electrophoretic separation of the single strand DNA after sequencing reactions was done under denaturing conditions over 6% polyacrylamide urea gels. The exact composition and procedure has already been described by Mai B. in "Genetic Characterization and Expression of the Large Thermosome Subunit from Pyrodictium Occultum in *E. Coli* and Molecular Biological Studies on the Extracellular Network form *Pyrodictium abyssi* Isolate TAG11," Thesis from the Department of Microbiology at the University of Regensburg (1995).

EXAMPLE 13

Bacteriophages: Lysates and DNA Preparation a) Titer Determination of Phage Lysates To determine the number of phages per ml lysate (plaque forming units, pfu), dilution series ($10^{-2}$ to $10^{-8}$) in SM buffer (50 mM Tris/HCl (pH 7.5), 100 mM NaCl, 10 mM MgSO$_4$) were prepared from the lysate. 100 µl at a time were plated out as follows. The dilution was mixed with 100 µl host cell culture (*E. coli* Y1090, OD$_{600}$=1.0 in 10 mM MgSO$_4$), incubated at 37° C. for 30 minutes and the entire batch was added to 3 ml NZY Top agar (see example 6, melted at 100° C. and cooled to 48° C.). Following fast mixing, the Top agar was poured immediately and uniformly on preheated NZY plates. Bacteria races and plaques developed overnight at 37° C. The phage titer in the lysate could be determined by counting out and by taking dilution factors into consideration.

b) Isolation of Phage Plaques

To separate the bacteriophages with the desired DNA sequence from others, they were first isolated by plating out (10.1) 200-400 pfu per NZY plate (diameter 9 cm). The desired plaques were picked out with a sterile glass pasteur pipette and transferred into 100-200 µl phage buffer (20 mM Tris/HCl (pH 7.4), 100 mM NaCl, 20 mM MgSO$_4$). The phages were diffused from the agar either in one hour at 37° C. or overnight at 4° C. For longer storage at 4° C., a drop of chloroform was added to keep it sterile.

c) Preparation of λ Phages (Liquid Culture Method)

500 µl fresh overnight culture from the host strain *E. coli* (single colony in 10 ml LB$_o$ with 0.2% maltose and 10 mM MgSO$_4$) were quickly and thoroughly mixed with 20 µl phage solution (10.2≈$10^5$ pfu) and incubated in the water bath at 37° C. for 20 minutes.

Then the mixture with the infected cells (the host strain *E. Coli* with phages) was added to 100 ml preheated LB$_0$ (37° C. with 1 mM MgSO$_4$ and 10 mg ampicillin) and intensively shaken at 37° C. Five to seven hours later, the cell lysis had taken place. It had taken place with regular measurements of OD$_{600}$ during incubation. To clarify the culture (=cell lysis), 500 µl chloroform were added and shaken for another 15 minutes. The cell fragments were removed by centrifugation (JA 10 rotor, 7,000 rpm, 10 min); and the phage-containing supernatant was transferred into sterile vessels and stored at 4° C.

d) Isolation of the Phage DNA

The phase DNA was isolated from 10 ml lysate (10.3) with the Wizard™ Lambda Preps DNA Purification system (Promega, Mannheim).

EXAMPLE 14

Identification of Desired DNA Sequences a) Preparation of DIG-Marked Probes

DIG-11-dUTP (digoxygenin or DIG) is a substrate for the *E. coli* DNA polymerase, T4 DNA polymerase, Taq DNA polymerase and reverse transcriptase. It may be used in the "nick translation" reaction and the "random primed DNA labeling" method in place of dTTP for DNA marking (DIG-11-dUTP:dTTP=35%:65%). The DIG-marked DNA can then be identified using the following procedure.

i. DIG-11-dUTP Incorporation into PCR Products

During a standard PCR (see Example 15) 2 µl DIG-11-dUTP (1 mM) were added to the batch.

ii. "Random Primed DNA Labeling" Reaction

The finished PCR product was marked according to the instructions provided by Boehringer, Mannheim. For example, starting from random primers, different sizes of segments of a DNA are synthesized using Klenow polymerase, whereby DIG-11-dUTP is incorporated. The size of the DIG-marked DNA fragments, which are obtained in the "random primed" DNA marking process, depends on the quantity and the length of the matrices-DNA. Every 20th to 25th nucleotide of the freshly synthesized DNA is a DIG-11-dUTP.

15 µl cleaned PCR product (1.5 µg; made in example 15) were boiled in the water bath for 10 min. and then quickly cooled on an ice NaCl mixture, since a complete denaturing turned out to be especially important for effective marking. 2 µl hexanucleotide mixture (10×), 2 µl DIG DNA Labeling Mix (10×) and 1 µl Klenow enzyme (2U) were added; and the mixture was incubated at 37° C. for two hours. Then the reaction was stopped by adding 2 µl 0.2 M EDTA (pH 8.0) and 2.5 µl 4 M LiCl$_2$. The marked DNA was precipitated with ethanol and dissolved in 50 µl TE buffer (10 mM Tris/HCl (pH 8.0), 1 mM EDTA) at 37° C. (30 min.).

b) Detection in *E. coli* Transformants i. Colony Transfer ("Colony Lift")

To detect positive colonies following transformation (see example 16.f), up to 100 transformants were inoculated on two identical $LB_0$ scanning plates with suitable antibiotic addition and incubated at 37° C. overnight. A dry nylon membrane (Hybond™ –$N^+$, Amersham, Braunschweig) was laid on the grown colony at RT for 3 minutes, after the plates had been stored at 4° C. for four hours. Then the membrane was laid on a NaOH-saturated (0.5 M) Whatman 3 MM paper with the colony side up for 5 min., then 2 minutes on dry and once again 5 min on a NaOH-saturated Whatman 3 MM paper. Finally the alkaline denaturated DNA was fixed on the membrane (120° C., 45 min.). Through hybridizing the membrane with a DNA probe (see example 19.a) and detecting DIG with chemiluminescence (see example 19.f), the transformants with the desired DNA sequence could be identified on the scanning plate and inoculated from the second plate.

ii. Plasmids and Phage DNA

Isolated plasmid and phage DNA were checked as follows. DNAs with predetermined concentrations (1 pg up to 100 ng plasmid, 1 ng up to 10 μg phage DNA) were dapped on a dry nylon membrane (Boehringer, Mannheim). For comparison purposes, the appropriate controls (e.g. vector without insert) were always carried out at the same time. As described in example 19.b.i), the applied DNA was denatured with alkaline and fixed. Then the DNA on the membrane was hybridized with the appropriate probe overnight (see example 19.e) and the DIG-marked DNA was detected (see example 19.f).

c) Identification in Bacteriophages i. Phage Mixtures ("Plaque Lift")

If the desired DNA sequence was identified in lysates with different phages (e.g. in the gene bank), then 200 to 400 pfu in NZY Topagar was plated out on NZY plates (see example 6). As described for the bacteria colony (example 19.b.i), the phages were then transferred onto a nylon membrane; the DNA was released with NaOH, denatured and then heat fixed. The DIG identification was directly conducted colorimetrically (see example 19.f) on the membrane in order to facilitate the allocation of signal and plaque. Then the identified plaques could be isolated from the plate (see example 18.b).

ii. Mini Lysates

9 μl lysate was treated with 1 μl 2 M NaOH and 2 mM EDTA and incubated at RT for 10 minutes. Then 2 μl per batch was pipetted on a dry nylon membrane (Boehringer, Mannheim). After 30 minutes at 120° C., the membrane was hybridized with the corresponding probe. The DIG was identified with chemiluminescence (see example 19.f).

d) Identification in Restriction-Digested DNA (Southern Blot)

| | |
|---|---|
| TAE running buffer: | 40 mM Tris/acetic acid (pH 8.4), 10 mM EDTA |
| Denaturing buffer: | 0.5 NaOH, 1.5 M NaCl |
| Neutralizing buffer: | 1 M Tris/HCl (pH 7.5), 1.5 M NaCl |
| 10 × SSC: | 1.5 M NaCl, 0.15 M Na citrate, (pH 7.0) |

First, the restriction-digested DNA (see example 16.a) was separated on a 1% SeaKem agarose gel in TAE buffer (see example 16.b) and photographed (together with a ruler as the scale). The gel was incubated for 8 min in 0.25 M HCl, then 20 min in denaturing buffer and finally incubated in neutralizing buffer for 20 minutes. In the interim a nylon membrane (Boehringer, Mannheim) and two Whatman filters (3 MM), which had been soaked in 10×SSC for 1 minute just before use, were cut to fit the size of the gel.

The DNA fragments were then transferred to a positively loaded nylon membrane with a Posi Blot 10-30 (Strategene, Heidelberg). A moist Whatman paper and the wetted membrane were laid on the rough side of the blot apparatus. Over this was laid a plastic template, whose edges were approximately 0.5 cm smaller than the gel. The pretreated gel was placed on the template in such a manner that the application wells rested on the plastic and the opening of the template was completely covered. Another Whatman paper was put on the gel. Finally a wet sponge (10×SSC) was put on the top. Excess pressure (70-80 mm Hg) was applied on the sponge for one hour.

Then gel traces and start line were marked on the membrane and the transferred DNA was fixed at 120° C. for 30 minutes. Following hybridization (see example 19.e) and DIG detection (see example 19.f), the fragments with the desired DNA sequence could be clearly identified (at split plasmids or phage DNAs) or at least assigned to a specific size range (for digestion of chromosomal DNA).

e) Hybridization with DIG Probes

In a hybridization buffer DIG Easy Hyb (Boehringer, Mannheim), a probe concentration of 20 ng/ml was set. A DIG-marked probe was denatured at 100° C. for 5 minutes and cooled on ice. The hybridization solution was used multiple times. Between the individual hybridizations it was stored at −10° C. and denatured at 68° C. for 15 minutes prior to be reused. DIG Easy Hyb contains no formamide. However, the hybridization temperature was analogously calculated to the formamide-containing hybridization solution (50%). Typically, a hybridization temperature ranging from 43-50° C. was determined for the *Pyrodictium* probes. To detect homologous genes with the probes, the hybridization temperature was decreased (*Pyrodictium* DNA: 42° C.; DNA of other organisms: 34° C.). After 30 minutes pre-hybridization (without probe) the batch was hybridized overnight, then washed 2×5 min in 2×SSC with 0.1% SDS (w/v) at room temperature. Finally the membrane was shaken for 2×15 min. longer in 0.1×SSC with 0.1% SDS (w/v) at 68° C. (*Pyrodictium* DNA) or 60° C. (DNA of other organisms).

f) Detection of DIG-Marked DNA

| | |
|---|---|
| Buffer 1: | 0.1 M maleic acid/NaOH (pH 7.5), 0.15 M NaCl |
| Wash buffer: | 0.3% (v/v) Tween 20 in buffer 1 |
| Buffer 2: | 1% (w/v) blocking reagent in buffer 1 |
| Buffer 3: | 0.1 M Tris/HCl (pH 9.5), 0.1 M NaCl, 50 mM $MgCl_2$ |
| NBT solution: | 75 mg NBT in 1 ml 70% dimethylformamide |
| BCIB solution: | 50 mg BCIP in 1 ml dimethylformamide |

The membrane was first shaken in the wash buffer for 2-5 minutes. Then the free binding sites on the membrane were saturated with buffer 2 for 30 minutes. Thereafter, the anti-DIG alkaline phosphatase conjugate was diluted in buffer 2 (1:10,000). The membrane was then incubated in the diluted anti-DIG alkaline phosphatase conjugate for 30 minutes. Unbound antibody conjugates were removed by 2×15 min. shaking in the wash buffer. Then the membrane was equilibrated in buffer 3 for 3 minutes.

Colorimetric Detection:

90 μl NBT and 70 μl BCIP solution were added to 20 ml buffer 3 to form a mixture. The membrane was coated with the mixture and left standing in the dark to incubate (30-120 min). The reaction (violet-brownish coloration) was terminated by placing the membrane in water.

Chemiluminescence Detection:

CDP-Star™ chemiluminescence substrate was diluted 1:10 in buffer 3 and inserted together with the membrane into a plastic sheet. The DIG-marked DNA was made visible with an x-ray film (Biomax MR1, Kodak, applied for 3 min-12 hours).

EXAMPLE 15

Expression of Recombinant Proteins in E. Coli a) Expression System that Was Used To express foreign proteins in the *E. coli* strain BL21 (DE3), the vector pET17b was used. The expression strain BL21 (DE3) pLysS accommodates the lysogenic phage DE3, which exhibits in turn the T7 RNA polymerase gene under the control of the lacUV5 promoter. The induction of this promoter with IPTG results in the synthesis of the T7 RNA polymerase, which, starting from the T7 promoter on pET17b, causes at this stage the transcription of the incorporated genes. The plasmid pLysS, which is also contained in the expression strain, carries not only a chloramphenicol resistance gene but also the gene for T7 lysozyme, an inhibitor of T7 RNA polymerase. Of course, the lysozyme gene is expressed only weakly, thus inhibiting the polymerase, formed in small quantities, in non-induced cells. This inhibiting effect can be easily overcome through induction of the polymerase. Thus, pLysS does, in fact, suppress the basal expression of foreign genes, but does not have a negative effect on the expression after induction.

b) Protocol

First of all, the vector pET17b was linearized with NdeI and NotI (see example 16.a) and dephosphorylated with CIP (see example 16.b). Then the NdeI and NotI sites were attached to the genes to be expressed by PCR (see example 15.c). The formed PCR products were cleaved with NdeI and NotI (see example 16.a), separated on an agarose gel and isolated (see example 14.c). The fragments (vector and insert) prepared thus were ligated (see example 16.e) and transformed in DH5α cells (see example 16.f). The transformants were checked for their insert size (see example 15.b). The resulting plasmid such as pEX-CAN-A was prepared from suitable transformants (see example 13); and for the control the transition sites from the vector to the insert were sequenced (see example 17.a). Then the transformation in BL21 (DE3) took place (see example 16.f).

To express the cannulae genes such CanA, CanB, CanC, CanD, CanE or sequences substantially identical thereof, the following procedure was followed:

A transformant pre-culture (2.5 ml $LB_0$ with ampicillin) was shaken up to an $OD_{600}=1.0$ at 37° C. and stored at 4° C. overnight. The next day this pre-culture was removed by centrifugation at 12,000 rpm in an ERV for 30 s. The pellet was resuspended in 2 ml fresh $LB_0$. Thus 50 ml $LB_0$ medium (+ampicillin) was inoculated. This medium was incubated with shaking at 37° C. The growth was monitored by routine OD measurement. At $OD_{600}=0.6$, 80 µl were removed. Then with the addition of IPTG (final concentration 0.3 mM) the T7 RNA polymerase was induced. Every 30-45 min. the $OD_{600}$ was measured; and 40 µl samples were removed. The cell samples were removed by centrifugation, resuspended in 10 µl application buffer (see example 22.a.i), and stored at −20° C. until the application on an SDS polyacrylamide gel (see example 23.a). As the control, a parallel batch with BL 21 (DE3) was inoculated with pET17b (without the insert) and prepared similarly. The cell harvest (JA 20 rotor, 9,000 rpm, 10 min, 4° C.) took place 3.5 hours after induction.

EXAMPLE 16

Isolating Recombinant Proteins from E. Coli

| | |
|---|---|
| Low salt buffer: | 80 mM NaCl, 50 mM Tris/ HCl (pH 7.5), 9% glycerol |
| High salt buffer: | 1.2 M NaCl, 50 mM Tris/ HCl (pH 7.5), 9% glycerol | a) CanA and CanB

One gram of recombinant *E. coli* with a particular sequence such as CanA or CanB expressed was absorbed in 4 ml low salt buffer. Cell lysis was conducted with a French press (2× at 20,000 psi, American Instrument Co., Silver Spring, USA). After pelletizing the cell fragments (Eppendorf centrifuge, 13,000 rpm, 5 min., RT), the protein solution was incubated at 80° C. for 20 min. Then the denatured proteins were removed by centrifugation (as above). The supernatant was passed at 1 ml/min through a Q sepharose column (1×12 cm=9.4 ml, Pharmacia, Freiburg). The eluent containing CanA or CanB was collected. The collected eluant was treated with leupeptin (1 µg/µl) and concentrated by a factor of 3-4 (based on the volume) in 4-8 hours in the Macrosep™ centrifuge concentrators (Pall Filtron, Dreieich) with an exclusion limit of 5 kDA. After determining the protein concentration with the BCA test (see example 22.b.i), the purified protein was shock frozen in liquid nitrogen in 100-200 µl aliquots and stored at −80° C. In each working step, a sample was taken and analyzed on an SDS polyacrylamide gel (see example 22.a).

b) CanC

The first step of isolating CanC is same as that of CanA and CanB (see example 21.a). However, during the second step, CanC was retained on the Q sepharose. After flushing the column with low salt buffer, CanC was eluted from the column with a salt gradient (80-750 mM, in 60 ml) and collected by fractionation (1 ml each). Following analysis of the individual fractions on an SDS polyacrylamide gel (see example 22.a), the CanC-containing fractions were combined and dialyzed against the low salt buffer at 4° C. overnight. Finally the protein solution was eluded at 1 ml/min through a 1 ml ResourceQ column (Pharmacia, Freiburg). Then a salt gradient (80-750 mM, in 60 ml) was applied and 0.5 ml fractions were collected. After analysis of the same on an SDS polyacrylamide gel (see example 22.a), the CanC-containing fractions were combined again and dialyzed against low salt buffer overnight. Following addition of leupeptin (1 µg/µl), the solution was concentrated by a factor of 7 (based on the volume) in 6 hours in the Microsep™ centrifuge concentrators (Pall Filtron, Dreieich) with an exclusion limit of 5 kDa. The rest of the protocol is same as those described in example 21.a.

EXAMPLE 17

Analysis of Protein Solutions a) SDS Polyacrylamide Gel Electrophoresis (Laemmli, 1970)
  i. Solutions that Were Used

| Running buffer (5x): | Tris | 25 mM |
| --- | --- | --- |
|  | glycine | 250 mM |
|  | SDS | 0.1% |
| Application buffer (1x): | Tris/HCl (pH 6.8) | 50 mM |
|  | SDS | 2% |
|  | 2-mercapto ethanol | 5% |
|  | glycerol | 10% |
|  | bromophenol blue | 0.1% |

Gel solutions (volume in μl):

|  | Gel Seal | 3% Collection Gel | 5% Separation Gel | 25% Separation Gel |
| --- | --- | --- | --- | --- |
| 1 M Tris (pH 8.8) | 250 | — | 1250 | 1250 |
| 1 M Tris (pH 6.8) | — | 1250 | — | — |
| H₂O bidist | 285 | 7500 | 2900 | — |
| 60% acrylamide | 330 | 500 | 420 | 2100 |
| 2.5% bisacrylamide | 85 | 610 | 400 | 1200 |
| 10% SDS | 10 | 100 | 50 | 50 |
| 85% glycerol + BPB | — | — | — | 400 |
| TEMED | 1 | 10 | 1 | 0.5 |
| 30% APS | 10 | 70 | 5 | 5 | ii. Protocol

To separate denatured proteins according to their size, SDS polyacrylamide gels were used. Separating gels (8.5 cm×6.5 cm, thickness 0.75 mm) having a linear acrylamide gradient ranging from 5 to 25% were poured. Following polymerization for one hour, a 3% collection gel was layered over the separating gel; and a comb with 10 application wells was inserted. The samples were absorbed in 10 μl application buffer, heated in the boiling water bath for 4 min. and applied with an extended pipette tip.

Electrophoresis was conducted at a constant current strength of 20 mA/gel (Mighty Small SE 250; Hoefer, San Francisco, USA). As soon as the bromophenol blue front had reached the bottom gel edge, the gel run was terminated.

b) Coomassie Staining of SDS Gels

| Staining solution: | coomassie R 250 | 0.1% |
| --- | --- | --- |
|  | methanol | 30% |
|  | glacial acetic acid | 10% |
| Destainer: | methanol | 30% |
|  | glacial acetic acid | 10% |

The gel was coated with a staining solution, stained at 50° C. for 30 min. with gentle shaking, and then destained under the same conditions. The destainer was changed several times. (The destainer can be regenerated by filtration over activated charcoal). When the desired decoloration was reached, the gel was rinsed with water, photographed (CCD video camera with "Easy" evaluation program and Thermoprinter, Herolab) and vacuum dried between two sheets (deti, Meckesheim) at 80° C.

c) Protein Concentration Determination
  i. Photometric Determination

The protein concentration of the purified protein was determined as described (Stoscheck C. M., 1990) at $OD_{280}$ nm. In this respect the following formula holds:

$$\text{protein concentration (mg/ml)} = OD_{280} \times MW/\epsilon_M,$$

where MW stands for the molecular weight; and $\epsilon_M$, the molar extinction coefficient. For the proteins researched in this study, the protein-dependent multiplication factor $$P = MW/\epsilon_M$$

amounts to:

| CanA | = 19930.38/22900 | = 0.87 |
| --- | --- | --- |
| CanB | = 15606.44/7680 | = 2.03 |
| CanC | = 16699.81/15990 | = 1.04 | ii. Bicinchonic Acid Test (BCA)

The test was conducted according to the manufacturer's guide (Sigma, Deisenhofen). To this end, aliquots of protein samples (CanA, B, C) and of known BSA dilutions were mixed with 50 times the volume of a fresh $BCA/CuSO_4$ (50:1) solution, incubated at 60° C. for 30 min. and measured in the spectrometer at 562 nm after cooling to RT. The protein concentrations were measured with the BSA calibration line.

iii. Amido Black Test (Heil and Zillig, 1970)

1-5 μl protein solution (Py-PP1) and 0.5-10 μg standard (BSA) were transferred to a cellulose acetate sheet (CA 251/0, Schleicher & Schuell, Dassel). After drying, the sheet was stained in 0.25% (w/v) amido black, 45% (v/v) methanol, 10% (v/v) glacial acetic acid for 10 minutes followed by being destained in 45% (v/v) methanol and 10% (v/v) glacial acetic acid. The sheet was dried again, protein spots were punched out and dissolved in 800 μl 10% (w/v) TCA, 80% (v/v) formic acid, 10% (v/v) glacial acetic acid respectively. Finally the $OD_{623}$ was measured; and the quantity of protein in the samples was determined by comparing with the BSA calibration line.

EXAMPLE 18

Evaluation of DNA and Protein Sequences

The analysis of the obtained DNA and protein sequences, homology calculations and the search for related sequences in the gene banks were performed with the program package from the University of Wisconsin Genetics Computer Group (UWGCG). To search for homologous DNA or protein sequences, the database of EBI, Hinxton Hall, UK was used. For example, the search programs "Fasta3," "Blast2"and "Blitz" were used.

EXAMPLE 19

Reconstitution Experiments a) Protocol

The reconstitution experiments with the purified recombinant cannulae subunits were conducted in a 1.5 ml ERV. The batch volume was 50 μl. Aliquots of a newly thawed, purified protein (CanA: 1.3 mg/ml; CanB: 1.1 mg/ml; CanC: 2.0 mg/ml) were used. The different salt concentrations were adjusted by adding 1 M stock solutions of the appropriate chloride salts. Usually, 20 mM salt was added. The respective pH value was adjusted with HCl or NaOH. Then the pH value was estimated with pH indicator rods from Merck (Darmstadt).

Experiments under various temperatures between 4° C. and 100° C. were carried out. To prevent the batches from evaporating prematurely, they were coated with mineral oil.

The reconstitution batches were incubated between 2 hours and 14 days and routinely checked for recombinant cannulae with the electron microscope. The standard incubation period was two days.

| Standard batch at 30° C. (pH 6.0): | |
|---|---|
| protein solution | 47 µl |
| CaCl$_2$/MgCl$_2$ (per 1 M) | 1 µl |
| HCl (2.5%) | 1 µl |
| NaN$_3$ (0.1 M) | 1 µl | b) Evaluation

8 µl of each of the reconstitution batches were pipetted onto a mica-coated copper net (Plasma Cleaner PDC-3XG, Harrick Sci. Co., Ossinining, N.Y., USA) with carbon sheet (400 mesh, Taab, Berkshire, UK). After an absorption period of 15 seconds, the suspension was drawn off with filter paper from the bottom. After washed with a drop of H$_2$O$_{bidist}$, the grid was coated with a drop of 3% uranyl acetate solution. Then after waiting for 45 seconds, the contrast agent uranyl acetate was stripped away with filter paper. Then the preparation was analyzed with a Philips CM 12 transmission electron microscope (Philips, Eindhoven, NL) (FIG. 1).

c) Stability Experiments

The polymerized cannulae from CanA were checked for thermostability under different conditions. The stability experiments of the recombinant cannulae were conducted either in SME 1/2 or in standard polymerization buffer. To study the pressure dependence, excess pressure of 5 bar was adjusted, where stated, with N2 at room temperature. The batches were immersed either in the glycerol bath (F6-B5 model, Haake, Karlsruhe), or incubated in the hot air incubator (Heraeus, Hanau).

Buffers that Were Used:

The following solutions were established for the experiments after the polymerization of recombinant subunits.

standard polymerization buffer:

50 mM Tris/HCl (pH 6.0), 80 mM NaCl, 9% glycerol, 20 mM CaCl$_2$, 20 mM MgCl$_2$ SME ½*: SME medium (see Example 6) 1:100 diluted with standard polymerization buffer Following incubation, the diluted batches were collected by centrifugation at 20,000 rpm (JA 21 rotor) for 15 minutes. The pellet was absorbed in 10 µl standard polymerization buffer, with which the copper net was coated (see Example 24.b).

Incubation Vessels:

1.5 ml Eppendorf screw-cap reaction vessels with packing ring, during incubation without pressure.

Glass vessel with rounded edge, plugged with a rubber stopper and sealed with aluminum caps, during incubation with pressure (RT: 5 bar N$_2$)

The batches in the ERV were submerged directly into hot (100-130° C.) glycerol (60 min) and then cooled on ice. The batches in the vessels with rounded edge were put directly into the hot air incubator (90-140° C.) (75 or 95 min.). In the case of immersion in hot glycerol (60 min), they were pre-incubated (in glycerol) at 100° C. for 1 minute.

EXAMPLE 20

Production of the Polymer of the Present Invention.

a) 300L Fermentor Culture of Recombinant *E. Coli*.

A 300 L culture of recombinant *E. coli* BL21 (DE3) harboring expression plasmid pEX-CAN-A (produced by attaching sequence substantially identical to SEQ ID NO. 1 to a vector pET 17b using a procedure described in Example 15) was grown in a HTE-Fermentor (Bioengineering, Wald, Switzerland) at 37° C. under aeration (165 L air/min.) and stirring (400 rpm) with a doubling time of about 40 min. At an O.D. (600 nm) of 0.80, production of Can A protein was induced by addition of 30 grams of IPTG. Cells were harvested 3 hours after the induction and after being cooled down to 4° C. Cell yield: 1,610 grams (wet weight).

b) Production of the Polymer.

i. French Press.

250 g frozen cell mass of recombinant *E.coli* (stored at −60° C.) were suspended in 600 ml buffer (Tris-HCL 50 mM, pH 7.5, containing 80 mM NaCl and 9% (v/v) glycerol). Final volume: 900 ml. Cells were broken down by a French Press (Aminco; 1×20,000 PSI). The viscosity of the solution was lowered by shearing the DNA using an Ultraturrax blender and by adding additional 400 ml buffer.

ii. Centrifugation.

Particles were removed by centrifugation (Sorvall SS34 rotor; 19,000 rpm, 15 min.) and a clear supernatant (called "crude extract") was obtained.

iii. Heat Precipitation.

To precipitate the heat-sensitive protein, the crude extract was heated to 100° C. for 1 min. For example, the crude extract (1,200 ml) was pumped through a 75 cm long plastic hose (inner diameter, 5 mm; 4.75 ml/min) immersed in a 100° C. hot water-glycerol-bath (water:glycerol=1:1). The outlet end of the plastic hose was passed through an ice bath to cool down the solution in the hose before solution was finally collected using an Erlenmeyer flask.

iv. Centrifugation.

The heat-treated crude extract was centrifuged for 25 min. at 9,000 rpm in Sorvall rotor GSA. The clear supernatant was collected.

v. Ammonium Sulfate Precipitation.

To the clear supernatant (840 ml), a 100% saturated ammonium sulfate solution (452 ml) was added at 4° C. (final ammonium sulfate concentration: 35% saturation). After 2 hours at 4° C., the precipitate was collected by centrifugation (1 hour; 13,000 rpm; Sowall rotor GSA). The precipitate was then solubilized in a buffer solution (final volume 171 ml; 12.35 mg protein/ml; 2,112 mg total protein) to form a protein solution. Finally, the protein solution was dialyzed by Rapid Dialysis against another buffer solution until its conductivity was the same as that of the buffer (3 hours).

vi. Polymerization.

The dialyzed protein solution was diluted by addition of buffer to a final protein concentration of 6.5 mg/ml (final volume 325 ml). Then, under shaking in a 1 L Erlenmeyer flask at 100° C. (in a water bath), the diluted protein solution was rapidly heated to 80° C. and then immediately transferred into a 500 ml screw-capped storage bottle. The storage bottle contained 3.32 ml (21.58 mg protein) of "Polymer Primers" (the "Polymer Primers" had been prepared before by 4 times French Press-shearing of a prefabricated Polymer suspension). Then, CaCl and MgCl (each at 20 mM final concentration) were added to the mixture and the closed bottle was stored in an 60° C. water bath. After addition of these salts, the solution became immediately turbid, indicating rapid polymerization of the protein units. After 10 min polymerization, the formed Polymer fibers were sheared by ultraturraxing the solution for 20 seconds in order to create additional polymer primers to speed up polymerization. Traces of silicone antifoam may be added before the ultraturraxing to reduce foaming. Typically, after 10 min. polymerization at 80° C., Polymer or polymer fibers could be observed under an electron microscope. After 1 to 2 hours of polymerization, protein polymers could be completely removed from the solution by centrifugation (15 min., 20,000 rpm, Sorvall rotor SS34), indicating complete polymerization.

Yield of polymer: 2.1 grams (protein) from 250 grams (wet weight) of *E.coli* (about 1 g Polymer (dry weight)/119 g *E.coli*).

vii. Storage.

Wet: At 4° C. in a buffer containing 10 mM Na-Azide.

Dry: Freeze-drying the polymer after the polymer being washed with an 1/10 diluted buffer followed by centrifugation.

c) Properties of Polymer Fiber

The polymer may have a shape of a short fiber, and therefore is also called "polymer fiber." The polymer fiber is made from monomeric protein units (e.g. Can A: 182 amino acids: MW=19,830 Daltons, having a sequence of SED ID NO. 2). The secondary structure of the protein may be mainly β-sheets.

The protein subunits in the polymer are arranged in a right-handed or left-handed, two-stranded helix. Occasionally, the polymer fibers made up of a three-handed helix may be observed. The periodicity (the distance of one helix turn to the next) of the polymer is 4.4 nm. The polymer has a unique quaternary structure. There is no similar protein complex known today among prokaryotes and eukaryotes. The polymer fiber has an outer diameter of 25 nm and inner diameter, 21 nm (in suspension). Under an electronic microscope, the dry negatively stained polymer fibres exhibit an outer diameter of 32 nm due to collapsing. Length of the polymer fiber is mostly between 3 and 5 micrometers. Some of the polymer fibers may reach a length from 10 to 25 micrometers.

The polymer fibers may form bundles of tens and hundreds of Polymer fibers with an overall diameter of 100 to 500 nm. Occasionally the bundle may reach an overall diameter of 4,000 nm. The polymer fiber is at least stable up to 128° C.

EXAMPLE 21

Preparation of Lipid Coated Drug Delivery Complexes

To a solution containing 3 mg/ml monomeric protein units (e.g. Can A: 182 amino acids: MW=19,830 Daltons, having a sequence of SED ID NO. 2), a desired amount of drug molecules, and a sufficient amount of electrically neutral lipids, millimolar calcium and magnesium cations are added to form a mixture. The mixture is kept at ambient condition for a sufficient amount time until liposomes form. Thereafter, gel filtration chromatography is carried out on the mixture and the liposomes contained in the mixture are size fractionated. The desired fractions of the liposomes are then heated to 50° C. in the presence of millimolar amounts of calcium and magnesium cations to initiate the polymerization of the monomeric polypeptide units within each liposome. The polymerization results in the extreme deformation of the liposomes and produces sealed lipid tubules containing the drug molecules.

The foregoing examples have been presented for the purpose of illustration and description only and are not to be construed as limiting the invention in any way. The scope of the invention is to be determined from the claims appended hereto.

We claim:

1. A method of producing a polypeptide polymer comprising the steps of:
   (a) providing a plurality of monomeric polypeptides and at least one divalent cation or at least one template molecule, wherein the monomer polypeptides are capable of self assembly in the presence of a divalent cation or at least one template molecule; and
   (b) (i) polymerizing the monomeric polypeptides through a self assembly process in the presence of the at least one divalent cation, or, (ii) polymerizing the monomeric polypeptides in the presence of the at least one template molecule, under conditions wherein the monomeric polypeptides self assemble, thereby producing a polypeptide polymer,
   wherein each monomeric polypeptide of the plurality of monomeric polypeptides have either (a) an amino acid sequence as set forth in SEQ ID NO:2, SEQ ID NO:4, SEQ ID NO:6, SEQ ID NO:8, or SEQ ID NO:10, or, (b) an amino acid sequence as set forth in SEQ ID NO:2, SEQ ID NO:4, SEQ ID NO:6, SEQ ID NO:8, or SEQ ID NO:10, and having at least one conservative substitution,
   and at least one monomeric polypeptide of the plurality of monomeric polypeptides includes a modification comprising attachment of a polypeptide.

2. The method of claim 1, wherein at least one of the plurality of monomeric polypeptides is made by a method comprising the steps of:
   preparing a vector comprising a nucleic acid, wherein the nucleic acid encodes the monomeric polypeptide;
   inserting the vector into a host cell;
   growing the host cell in a suitable culture to express the nucleic acid to form the polypeptide; and isolating the formed monomeric polypeptide from the host cell.

3. The method of claim 1, wherein the step of polymerizing the monomeric polypeptides further comprises the steps of:
   dissolving the plurality of monomeric polypeptides in a solution; and
   adding a template molecule and an alkaline earth metal ion to the solution.

4. The method of claim 2, wherein the host is selected from the group consisting of prokaryotes, eukaryotes, funguses, yeasts, plants and metabolically rich hosts.

5. The method of claim 1, wherein the monomeric polypeptides polymerize to form a hollow tube, a tubule, a micelle or a molecular sieve.

6. The method of claim 5, wherein the hollow tube has approximately a 25 nm outer diameter and a 20 nm inner diameter.

7. The method of claim 1, wherein the plurality of monomeric polypeptides are polymerized in the presence of at least one divalent cation selected from the group consisting of $Ca^{2+}$, $Mg^{2+}$, $Cu^{2+}$, $Zn^{2+}$, $Sr^{2+}$, $Ni^{2+}$, $Mn^{2+}$ and $Fe^{2+}$.

8. The method of claim 1, wherein the plurality of monomeric polypeptides are polymerized in the presence of $Ca^{2+}$ and $Mg^{2+}$.

9. The method of claim 1, wherein the step of polymerizing the monomeric polypeptides further comprises the step of dissolving the monomeric polypeptides in an aqueous solution.

10. The method of claim 1, wherein the template molecule is prepared by fragmenting or shearing of a suspension of a polymer.

11. The method of claim 1, wherein the monomeric polypeptides interact with each other by pairing, bundling, entangling or electrostatic cross linking, thereby generating paired polymers, bundled polymers, entangled polymers, cross linked polymers or an interconnected network of polymers.

12. The method of claim 1, further comprising providing a therapeutic agent or a drug molecule and adding the therapeutic agent or drug molecule to the polymerization step, thereby generating a therapeutic agent or drug molecule encapsulated by the polymers.

13. The method of claim 12, wherein the therapeutic agent or drug molecule is added to the polymerization step.

14. The method of claim 13, further comprising capping the partially formed polymer using a capping unit.

15. The method of claim 14, wherein the capping unit comprises a polypeptide monomer.

16. The method of claim 13, wherein the therapeutic agent or drug encapsulating step is carried out by mixing the polymer and the therapeutic agent or drug molecule together in a solution such that the therapeutic agent or drug molecule can permeate inside the polymer.

17. The method of claim 12, further comprising attaching a targeting molecule, or an additional targeting molecule if a targeting molecule is already present, or a vector, or an additional vector if a vector is already present, to the therapeutic agent or drug-loaded polymer during the encapsulation process or after the completion of the encapsulation process.

18. The method of claim 12, further comprising using lipids or lipid molecules during the encapsulation process.

19. The method of claim 1, further comprising attaching the polymer to a hydrogel.

20. The method of claim 19, wherein the hydrogel comprises a three dimensional structural network for a biochip.

21. The method of claim 1, wherein the monomeric polypeptide has an amino acid sequence as set forth in SEQ ID NO:2.

22. The method of claim 1, wherein the conservative amino acid substitution comprises substituting one amino acid for another of the same class.

23. The method of claim 22, wherein the conservative amino acid substitution comprises substitution of one hydrophobic amino acid for another, or substitution of one polar amino acid for another.

24. The method of claim 23, wherein the conservative amino acid substitution comprises substitution of isoleucine, valine, leucine or methionine, for another hydrophobic amino acid.

25. The method of claim 23, wherein the conservative amino acid substitution comprises substitution of arginine for lysine, glutamic acid for aspartic acid or glutamine for asparagine.

26. The method of claim 1, wherein the polypeptide polymer is a nanoscale drug delivery vehicle.

27. The method of claim 1, wherein the polymer or at least one monomeric polypeptide further comprises an enzyme.

28. The method of claim 1, wherein the attached polypeptide is an enzyme, an antibody or a targeting molecule, or the polymer polypeptide further comprises a modification comprising an enzyme, an antibody or a targeting molecule.

29. The method of claim 1, wherein the attached polypeptide comprises a charged group.

30. The method of claim 1, wherein the attached polypeptide is attached to a monomeric protein as a recombinant fusion protein.

31. The method of claim 1, wherein an attached polypeptide is attached to one monomeric protein.

32. The method of claim 1, wherein a plurality of polypeptides are attached to a plurality of the monomeric polypeptides.

* * * * *

SEQUENCE LISTING

```
<160> NUMBER OF SEQ ID NOS: 10

<210> SEQ ID NO 1
<211> LENGTH: 624
<212> TYPE: DNA
<213> ORGANISM: Pyrodictium abyssi

<400> SEQUENCE: 1
gtgaagtaca caaccctagc tatagcgggt attattgcct cggctgccgc cctcgccctc      60
ctagcaggct tcgccaccac ccagagcccc ctcaacagct tctacgccac cggtacagca     120
caggcagtaa gcgagccaat agacgtagaa agccacctcg gcagcataac ccccgcagcc     180
ggcgcacagg gcagtgacga cataggttac gcaatagtgt ggataaagga ccaggtcaat     240
gatgtaaagc tgaaggtgac cctgcgtaac gctgagcagc taaagcccta cttcaagtac     300
ctacagatac agataacaag cggctatgag acgaacagca cagctctagg caacttcagc     360
gagaccaagg ctgtgataag cctcgacaac cccagcgccg tgatagtact agacaaggag     420
gatatagcag tgctctatcc ggacaagacc ggttacacaa acacttcgat atgggtaccc     480
ggtgaacctg acaagataat tgtctacaac gagacaaagc cagtagctat actgaacttc     540
aaggccttct acgaggctaa ggagggtatg ctattcgaca gcctgccagt gatattcaac     600
ttccaggtgc tacaagtagg ctaa                                            624
```

<210> SEQ ID NO 2
<211> LENGTH: 207
<212> TYPE: PRT
<213> ORGANISM: Pyrodictium abyssi

<400> SEQUENCE: 2

```
Val Lys Tyr Thr Thr Leu Ala Ile Ala Gly Ile Ile Ala Ser Ala Ala
 1               5                  10                  15

Ala Leu Ala Leu Leu Ala Gly Phe Ala Thr Thr Gln Ser Pro Leu Asn
            20                  25                  30

Ser Phe Tyr Ala Thr Gly Thr Ala Gln Ala Val Ser Glu Pro Ile Asp
        35                  40                  45

Val Glu Ser His Leu Gly Ser Ile Thr Pro Ala Gly Ala Gln Gly
    50                  55                  60

Ser Asp Asp Ile Gly Tyr Ala Ile Val Trp Ile Lys Asp Gln Val Asn
65                  70                  75                  80

Asp Val Lys Leu Lys Val Thr Leu Arg Asn Ala Glu Gln Leu Lys Pro
                85                  90                  95

Tyr Phe Lys Tyr Leu Gln Ile Gln Ile Thr Ser Gly Tyr Glu Thr Asn
            100                 105                 110

Ser Thr Ala Leu Gly Asn Phe Ser Glu Thr Lys Ala Val Ile Ser Leu
        115                 120                 125

Asp Asn Pro Ser Ala Val Ile Val Leu Asp Lys Glu Asp Ile Ala Val
130                 135                 140

Leu Tyr Pro Asp Lys Thr Gly Tyr Thr Asn Thr Ser Ile Trp Val Pro
145                 150                 155                 160

Gly Glu Pro Asp Lys Ile Ile Val Tyr Asn Glu Thr Lys Pro Val Ala
                165                 170                 175

Ile Leu Asn Phe Lys Ala Phe Tyr Glu Ala Lys Glu Gly Met Leu Phe
            180                 185                 190

Asp Ser Leu Pro Val Ile Phe Asn Phe Gln Val Leu Gln Val Gly
        195                 200                 205
```

<210> SEQ ID NO 3
<211> LENGTH: 513
<212> TYPE: DNA
<213> ORGANISM: Pyrodictium abyssi

<400> SEQUENCE: 3

```
gtgaagccta cggctctagc cctggctggt atcattgcct cggctgccga cctcgccctg      60
ctagcaggct tcgccaccac ccagagcccg ctcaacagct tctacgccac cggcacagca     120
gccgcaacaa gcgagccaat agacgtagag agccacctca gcagcatagc ccctgctgct     180
ggcgcacagg gcagccagga cataggctac ttcaacgtga ccgccaagga tcaagtgaac     240
gtgacaaaga taaggtgac cctggctaac gctgagcagc taaagcccta cttcaagtac     300
ctacagatag tgctaaagag cgaggtagct gacgagatca aggccgtaat aagcatagac     360
aagcctagcg ccgtcataat actagacagc caggacttcg acagcaacaa cagagcaaag     420
ataagcgcca ctgcctacta cgaggctaag gagggcatgc tattcgacag cctaccgcta     480
atattcaaca tacaggtgct aagcgtcagc taa                                  513
```

<210> SEQ ID NO 4
<211> LENGTH: 170
<212> TYPE: PRT
<213> ORGANISM: Pyrodictium abyssi

<400> SEQUENCE: 4

| | | | | | | | | | | | | | | | |
|---|---|---|---|---|---|---|---|---|---|---|---|---|---|---|---|
| Val | Lys | Pro | Thr | Ala | Leu | Ala | Leu | Ala | Gly | Ile | Ile | Ala | Ser | Ala | Ala |
| 1 | | | | 5 | | | | | 10 | | | | | 15 | |
| Asp | Leu | Ala | Leu | Leu | Ala | Gly | Phe | Ala | Thr | Thr | Gln | Ser | Pro | Leu | Asn |
| | | | 20 | | | | | 25 | | | | | 30 | | |
| Ser | Phe | Tyr | Ala | Thr | Gly | Thr | Ala | Ala | Ala | Thr | Ser | Glu | Pro | Ile | Asp |
| | | 35 | | | | | 40 | | | | | 45 | | | |
| Val | Glu | Ser | His | Leu | Ser | Ser | Ile | Ala | Pro | Ala | Ala | Gly | Ala | Gln | Gly |
| | 50 | | | | | 55 | | | | | 60 | | | | |
| Ser | Gln | Asp | Ile | Gly | Tyr | Phe | Asn | Val | Thr | Ala | Lys | Asp | Gln | Val | Asn |
| 65 | | | | | 70 | | | | | 75 | | | | | 80 |
| Val | Thr | Lys | Ile | Lys | Val | Thr | Leu | Ala | Asn | Ala | Glu | Gln | Leu | Lys | Pro |
| | | | | 85 | | | | | 90 | | | | | 95 | |
| Tyr | Phe | Lys | Tyr | Leu | Gln | Ile | Val | Leu | Lys | Ser | Glu | Val | Ala | Asp | Glu |
| | | | | 100 | | | | | 105 | | | | | 110 | |
| Ile | Lys | Ala | Val | Ile | Ser | Ile | Asp | Lys | Pro | Ser | Ala | Val | Ile | Ile | Leu |
| | | | 115 | | | | | 120 | | | | | 125 | | |
| Asp | Ser | Gln | Asp | Phe | Asp | Ser | Asn | Asn | Arg | Ala | Lys | Ile | Ser | Ala | Thr |
| | | | 130 | | | | | 135 | | | | | 140 | | |
| Ala | Tyr | Tyr | Glu | Ala | Lys | Glu | Gly | Met | Leu | Phe | Asp | Ser | Leu | Pro | Leu |
| 145 | | | | | 150 | | | | | 155 | | | | | 160 |
| Ile | Phe | Asn | Ile | Gln | Val | Leu | Ser | Val | Ser | | | | | | |
| | | | | 165 | | | | | 170 | | | | | | |

<210> SEQ ID NO 5
<211> LENGTH: 537
<212> TYPE: DNA
<213> ORGANISM: Pyrodictium abyssi

<400> SEQUENCE: 5

```
atgaggtaca cgaccctagc tctggccggc atagtggcct cggctgccgc cctcgccctg    60
ctagcaggct tcgccacgac ccagagcccg ctaagcagct tctacgccac cggcacagca   120
caagcagtaa gcgagccaat agacgtagag agccacctag acaacaccat agcccctgct   180
gccggtgcac agggctacaa ggacatgggc tacattaaga taactaacca gtcaaaagtt   240
aatgtaataa agctgaaggt gactctcgct aacgccgagc agctaaagcc ctacttcgac   300
tacctacagc tagtactcac aagcaacgcc actggcaccg acatggttaa ggctgtgcta   360
agcctcgaga gcctagcgc agtcataata ctagacaacg atgactacga tagcactaac   420
aagatacagc taaaggtaga agcctactat gaggctaagg agggcatgct attcgacagc   480
ctaccagtaa tactgaactt ccaggtactg agcgccgctt gcagtccctt gtggtga      537
```

<210> SEQ ID NO 6
<211> LENGTH: 178
<212> TYPE: PRT
<213> ORGANISM: Pyrodictium abyssi

<400> SEQUENCE: 6

| | | | | | | | | | | | | | | | |
|---|---|---|---|---|---|---|---|---|---|---|---|---|---|---|---|
| Met | Arg | Tyr | Thr | Thr | Leu | Ala | Leu | Ala | Gly | Ile | Val | Ala | Ser | Ala | Ala |
| 1 | | | | 5 | | | | | 10 | | | | | 15 | |
| Ala | Leu | Ala | Leu | Leu | Ala | Gly | Phe | Ala | Thr | Thr | Gln | Ser | Pro | Leu | Ser |
| | | | 20 | | | | | 25 | | | | | 30 | | |
| Ser | Phe | Tyr | Ala | Thr | Gly | Thr | Ala | Gln | Ala | Val | Ser | Glu | Pro | Ile | Asp |
| | | 35 | | | | | 40 | | | | | 45 | | | |

Val Glu Ser His Leu Asp Asn Thr Ile Ala Pro Ala Ala Gly Ala Gln
 50                  55                  60

Gly Tyr Lys Asp Met Gly Tyr Ile Lys Ile Thr Asn Gln Ser Lys Val
 65                  70                  75                  80

Asn Val Ile Lys Leu Lys Val Thr Leu Ala Asn Ala Glu Gln Leu Lys
                 85                  90                  95

Pro Tyr Phe Asp Tyr Leu Gln Leu Val Leu Thr Ser Asn Ala Thr Gly
            100                 105                 110

Thr Asp Met Val Lys Ala Val Leu Ser Leu Glu Lys Pro Ser Ala Val
            115                 120                 125

Ile Ile Leu Asp Asn Asp Asp Tyr Asp Ser Thr Asn Lys Ile Gln Leu
        130                 135                 140

Lys Val Glu Ala Tyr Tyr Glu Ala Lys Glu Gly Met Leu Phe Asp Ser
145                 150                 155                 160

Leu Pro Val Ile Leu Asn Phe Gln Val Leu Ser Ala Ala Cys Ser Pro
                165                 170                 175

Leu Trp

<210> SEQ ID NO 7
<211> LENGTH: 311
<212> TYPE: DNA
<213> ORGANISM: Pyrodictium abyssi

<400> SEQUENCE: 7
agcttctacg ccaccggcac agcacaggca gtaagcgagc caatagacgt ggtaagcagc      60
ctcggtacgc taaatactgc cgctggtgca cagggtaagc agacgctagg agacataaca     120
atatatgcgc acaatgacgt gaacataaca aagctaaagg tcacgcttgc taacgctgca     180
cagctaagac catacttcaa gtacctgata ataaagctag taagcctgga cagcaacggc     240
aacgagtccg aggaaaaggg catgataact ctatggaagc cttacgccgt gataatacta     300
gaccatgaag a                                                         311

<210> SEQ ID NO 8
<211> LENGTH: 130
<212> TYPE: PRT
<213> ORGANISM: Pyrodictium abyssi

<400> SEQUENCE: 8

Ser Phe Tyr Ala Thr Gly Thr Ala Gln Ala Val Ser Glu Pro Ile Asp
  1               5                  10                  15

Val Val Ser Ser Leu Gly Thr Leu Asn Thr Ala Ala Gly Ala Gln Gly
                 20                  25                  30

Lys Gln Thr Leu Gly Asp Ile Thr Ile Tyr Ala His Asn Asp Val Asn
             35                  40                  45

Ile Thr Lys Leu Lys Val Thr Leu Ala Asn Ala Ala Gln Leu Arg Pro
 50                  55                  60

Tyr Phe Lys Tyr Leu Ile Ile Lys Leu Val Ser Leu Asp Ser Asn Gly
 65                  70                  75                  80

Asn Glu Ser Glu Glu Lys Gly Met Ile Thr Leu Trp Lys Pro Tyr Ala
                 85                  90                  95

Val Ile Ile Leu Asp His Glu Asp Phe Asn Asn Asp Ile Asp Gly Asp
            100                 105                 110

Asn Gln Cys Gln Ile Asp Ala Thr Ala Tyr Tyr Glu Ala Lys Glu Gly
            115                 120                 125

Met Leu

-continued

```
    130

<210> SEQ ID NO 9
<211> LENGTH: 372
<212> TYPE: DNA
<213> ORGANISM: Pyrodictium abyssi

<400> SEQUENCE: 9
agcttctacg ccaccggcac agcagaggca acaagcgagc caatagacgt tgtaagcaac      60
cttaacacgg ccatagcccc tgctgccggc gcccagggca gcgtgggcat aggcagcata     120
acaatagaga acaagactga cgtgaacgtt gtgaagctga agataaccct cgccaacgct     180
gagcagctaa agccctactt cgactaccta cagatagtgc taaagagcgt tgacagcaac     240
gagatcaagg ctgtgctaag cctcgagaag cccagcgcag tcataatact ggacaacgag     300
gacttccagg gcggcgacaa ccagtgccag atagacgcca ccgcctacta cgaggctaag     360
gagggtatgc ta                                                         372

<210> SEQ ID NO 10
<211> LENGTH: 124
<212> TYPE: PRT
<213> ORGANISM: Pyrodictium abyssi

<400> SEQUENCE: 10

Ser Phe Tyr Ala Thr Gly Thr Ala Glu Ala Thr Ser Glu Pro Ile Asp
  1               5                  10                  15

Val Val Ser Asn Leu Asn Thr Ala Ile Ala Pro Ala Ala Gly Ala Gln
             20                  25                  30

Gly Ser Val Gly Ile Gly Ser Ile Thr Ile Glu Asn Lys Thr Asp Val
         35                  40                  45

Asn Val Val Lys Leu Lys Ile Thr Leu Ala Asn Ala Glu Gln Leu Lys
     50                  55                  60

Pro Tyr Phe Asp Tyr Leu Gln Ile Val Leu Lys Ser Val Asp Ser Asn
 65                  70                  75                  80

Glu Ile Lys Ala Val Leu Ser Leu Glu Lys Pro Ser Ala Val Ile Ile
                 85                  90                  95

Leu Asp Asn Glu Asp Phe Gln Gly Gly Asp Asn Gln Cys Gln Ile Asp
                100                 105                 110

Ala Thr Ala Tyr Tyr Glu Ala Lys Glu Gly Met Leu
                115                 120
```